United States Patent
Yun et al.

(10) Patent No.: US 7,363,076 B2
(45) Date of Patent: *Apr. 22, 2008

(54) TREATMENT OF CONDITIONS THROUGH MODULATION OF THE AUTONOMIC NERVOUS SYSTEM

(75) Inventors: Anthony Joonkyoo Yun, Palo Alto, CA (US); Patrick Yuarn-Bor Lee, Piedmont, CA (US)

(73) Assignee: Palo Alto Investors, Palo Alto, CA (US)

( * ) Notice: Subject to any disclaimer, the term of this patent is extended or adjusted under 35 U.S.C. 154(b) by 567 days.

This patent is subject to a terminal disclaimer.

(21) Appl. No.: 10/871,366

(22) Filed: Jun. 18, 2004

(65) Prior Publication Data

US 2005/0021092 A1  Jan. 27, 2005

Related U.S. Application Data

(63) Continuation-in-part of application No. 10/661,368, filed on Sep. 12, 2003, now Pat. No. 7,149,574.

(60) Provisional application No. 60/494,260, filed on Aug. 11, 2003, provisional application No. 60/482,593, filed on Jun. 24, 2003, provisional application No. 60/477,070, filed on Jun. 9, 2003.

(51) Int. Cl.
   *A61N 1/00* (2006.01)
(52) U.S. Cl. .......................................... 607/3
(58) Field of Classification Search .................. 607/2, 607/3
   See application file for complete search history.

(56) References Cited

U.S. PATENT DOCUMENTS

| | | |
|---|---|---|
| 5,188,104 A | 2/1993 | Wernicke et al. |
| 5,215,086 A | 6/1993 | Terry, Jr. et al. |
| 5,231,988 A | 8/1993 | Wernicke et al. |
| 5,263,480 A | 11/1993 | Wernicke et al. |
| 5,269,303 A | 12/1993 | Wernicke et al. |
| 5,330,515 A | 7/1994 | Rutecki et al. |
| 5,335,657 A | 8/1994 | Terry, Jr. et al. |
| 5,540,730 A | 7/1996 | Terry, Jr. et al. |
| 5,571,150 A | 11/1996 | Wernicke et al. |
| 5,707,400 A | 1/1998 | Terry, Jr. et al. |
| 5,978,702 A | 11/1999 | Ward et al. |
| 6,253,109 B1 | 6/2001 | Gielen |
| 6,319,241 B1 | 11/2001 | King et al. |
| 6,337,997 B1 | 1/2002 | Rise |
| 6,356,784 B1 | 3/2002 | Lozano et al. |
| 6,366,813 B1 | 4/2002 | DiLorenzo |
| 6,459,936 B2 | 10/2002 | Fischell et al. |

(Continued)

*Primary Examiner*—Scott M Getzow
(74) *Attorney, Agent, or Firm*—Bret E. Field; Bozicevic Field & Francis LLP.

(57) ABSTRACT

Methods are provided for treating a subject for a condition caused by an abnormality in the subject's autonomic nervous system. In accordance with the subject methods, at least a portion of a subject's autonomic nervous system is modulated to increase the parasympathetic activity/sympathetic activity ratio in a manner that is effective to treat the subject for the condition. Certain embodiments include modulating at least a portion of a subject's autonomic nervous system by inhibiting and/or increasing activity in at least a portion of the subject's autonomic nervous system. The subject methods find use in the treatment of a variety of different conditions, where such conditions include various disease conditions. Also provided are systems and kits for use in practicing the subject methods.

82 Claims, 3 Drawing Sheets

U.S. PATENT DOCUMENTS 6,480,743 B1 11/2002 Kirkpatrick et al.
6,484,059 B2 11/2002 Gielen
6,526,318 B1 2/2003 Ansarinia
6,609,025 B2 8/2003 Barrett et al.
7,162,303 B2 * 1/2007 Levin et al. .................. 607/44
2002/0177882 A1 11/2002 DiLorenzo
2003/0018367 A1 1/2003 DiLorenzo
2003/0144709 A1 7/2003 Zabara et al.
2004/0210261 A1 * 10/2004 King et al. .................... 607/9

* cited by examiner

Traditional View of the relationship between OSA nd conditions of inflammation such as CAD, HTN, DM New view of the relationship between OSA and conditions of inflammation such as CAD, HTN, DM

TREATMENT OF CONDITIONS THROUGH MODULATION OF THE AUTONOMIC NERVOUS SYSTEM

CROSS REFERENCE TO RELATED APPLICATIONS

The present application is a continuation-in-part application of application Ser. No. 10/661,368 filed Sep. 12, 2003, which application claims priority under 35 U.S.C. § 119(e) to U.S. provisional application No. 60/477070 filed Jun. 9, 2003, to U.S. provisional application No. 60/482593 filed Jun. 24, 2003 and to U.S. provisional application No. 60/494260 filed Aug. 11, 2003, the disclosures of which are incorporated herein by reference in their entirety.

FIELD OF THE INVENTION

The field of this invention is the treatment of conditions associated with the autonomic nervous system and more specifically the treatment of conditions through electrical modulation and/or pharmacological modulation of the autonomic nervous system.

BACKGROUND OF THE INVENTION

There are a variety of conditions that can affect an individual's health and well-being. The treatment of various conditions that affect the health and well-being of an individual has been around for centuries. Such treatments include pharmacological, surgical, and life style (dietetic, exercise, etc.) changes. In general, the armament of treatment options available to a physician to treat such conditions has increased tremendously, especially in the last century.

However, while the number of treatment options has increased, typically such options are merely palliative, i.e., are designed for the relief of symptoms of a condition rather than actually being curative of the disorder itself. In fact, treatment protocols effectively directed at the underlying cause of a condition are quite rare.

As such, there continues to be an interest in the development of new protocol options for treating conditions. Of particular interest are protocols for treating conditions that are directed at the cause of the condition rather than the symptoms thereof.

SUMMARY OF THE INVENTION

Methods are provided for treating a subject for a condition. Embodiments include electrically and/or pharmacologically modulating at least a portion of a subject's autonomic nervous system is electrically and/or pharmacologically modulated to increase the parasympathetic activity/sympathetic activity ratio in a manner that is effective to treat the subject for the condition. In certain embodiments, the condition treated is at least one of hypoxia, hypercapnia and acidosis. In certain embodiments, the condition treated is a condition having a manifestation of at least one of hypoxia, hypercapnia and acidosis.

Also provided are systems and kits for use in practicing the subject methods.

BRIEF DESCRIPTIONS OF THE DRAWINGS

DETAILED DESCRIPTION OF THE INVENTION

Figure 1:
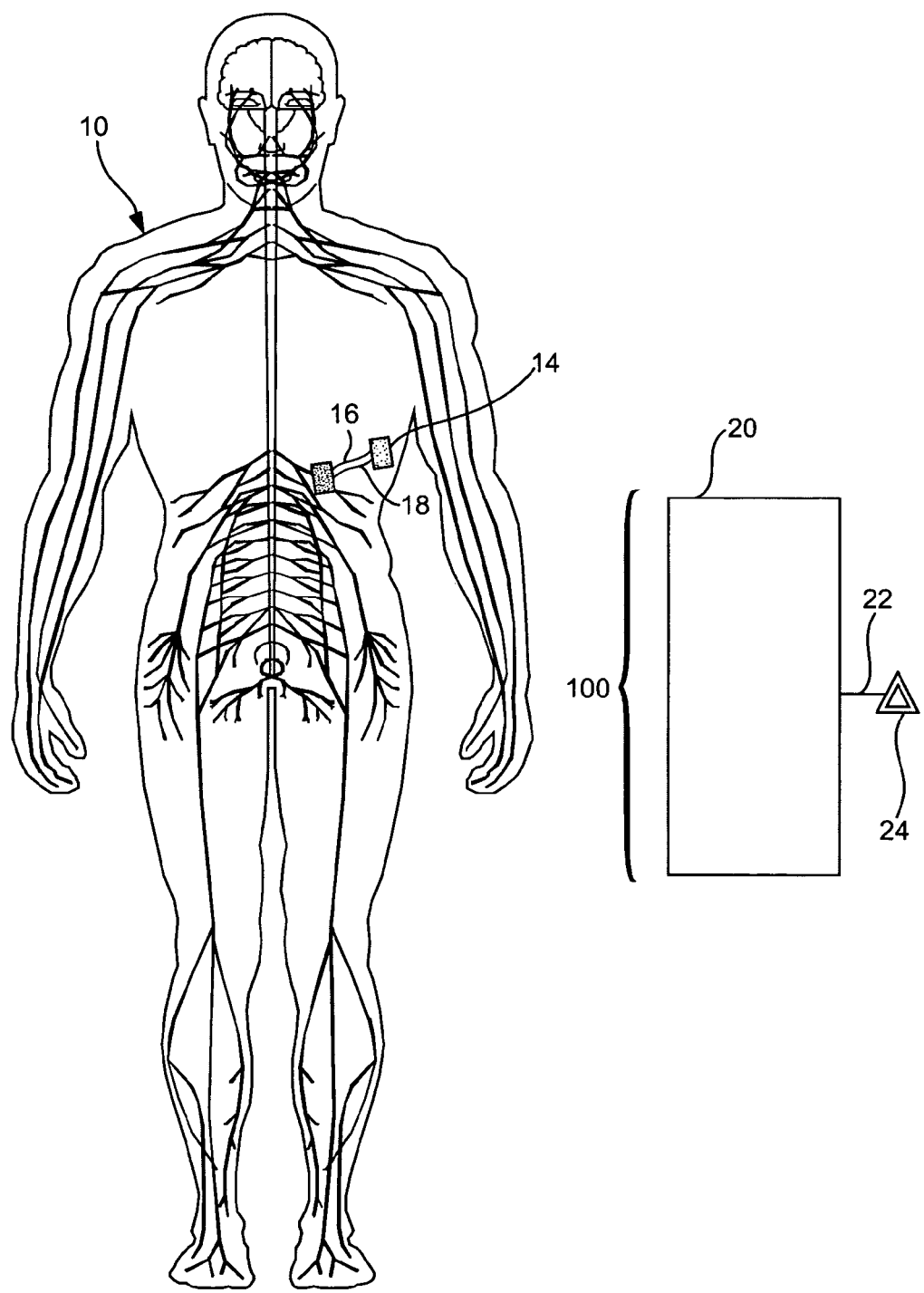
FIG. 1 shows an exemplary embodiment of an electrostimulatory device operatively positioned in a subject's body in accordance with the subject methods.

Methods are provided for treating a subject for a condition caused by an abnormality in the subject's autonomic nervous system. In accordance with the subject methods, at least a portion of a subject's autonomic nervous system is electrically modulated to increase the parasympathetic activity/sympathetic activity ratio in a manner that is effective to treat the subject for the condition. Certain embodiments include electrically modulating at least a portion of a subject's autonomic nervous system by inhibiting and/or increasing activity in at least a portion of the subject's autonomic nervous system. The subject methods find use in the treatment of a variety of different conditions, where such conditions include various disease conditions. Also provided are systems and kits for use in practicing the subject methods.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention.

The figures shown herein are not necessarily drawn to scale, with some components and features being exaggerated for clarity.

As summarized above, the subject invention provides methods for treating a subject for a condition caused by an abnormality in the subject's autonomic nervous system by electrically modulating at least a portion of the subject's autonomic nervous system to increase the parasympathetic activity/sympathetic activity ratio. In further describing the subject invention, representative embodiments of the subject methods are described first in greater detail, followed by a review of various representative applications in which the subject methods may find use. Next, a review of systems and kits for use in the subject methods is provided.

Methods

As noted above, the subject methods are methods for treating a subject for a condition caused by an abnormality in the subject's autonomic nervous system. More specifically, the subject methods are methods for treating a subject for a condition caused by an abnormality in a subject's autonomic nervous system by electrically and/or pharmacologically modulating at least a portion of the subject's autonomic nervous system to increase the parasympathetic activity/sympathetic activity ratio in a manner effective to treat the subject for the condition or decrease parasympathetic activity/sympathetic activity ratio. Accordingly, the subject invention includes electrically and/or pharmacologically modulating at least a portion of a subject's autonomic nervous system to increase the parasympathetic activity/sympathetic activity ratio, i.e., increase parasympathetic activity relative to sympathetic activity or decrease the parasympathetic activity/sympathetic activity ratio. In accordance with the subject invention, increasing the parasympathetic activity/sympathetic activity ratio may be achieved by stimulating the parasympathetic system to increase activity in at least a portion of the parasympathetic system, e.g., stimulating at least one parasympathetic nerve fiber. Alternatively or in addition to stimulating at least one parasympathetic nerve fiber to increase activity, increasing the parasympathetic activity/sympathetic activity ratio may be achieved by inhibiting activity in the sympathetic system, e.g., inhibiting activity in at least one sympathetic nerve fiber. Accordingly, embodiments of the subject methods include providing electrical stimulation to at least a portion of a subject's autonomic nervous system, where such electrical stimulation may be excitatory or inhibitory and in certain embodiments may include both excitatory and inhibitory stimulation. Specifically, embodiments of the subject invention includes electrically stimulating at least a portion of a subject's autonomic nervous system to achieve a desired parasympathetic activity/sympathetic activity ratio, i.e., a desired balance between parasympathetic activity and sympathetic activity, analogous to a parasympathetic activity/sympathetic activity ratio observed in a healthy (i.e., a subject not experiencing an abnormality in the autonomic nervous system), "like" or rather analogous subject, e.g., a healthy human subject ranging in age from about 20 years old to about 25 years old (subjects other than humans will have analogous age ranges). For example, if the subject being treated is a human subject, the parasympathetic activity/sympathetic activity ratio provided by the subject invention is analogous to the parasympathetic activity/sympathetic activity ratio observed in a healthy human ranging in age from about 20 years old to about 25 years old.

Before further describing the subject methods, a review of the autonomic nervous system is provided to provide a proper foundation for the subject invention.

Review of the Autonomic Nervous System

The nervous system is divided into the somatic nervous system and the autonomic nervous system ("ANS"). In general, the somatic nervous system controls organs under voluntary control (e.g., skeletal muscles) and the ANS controls individual organ function and homeostasis. For the most part, the ANS is not subject to voluntary control. The ANS is also commonly referred to as the visceral or automatic system.

The ANS can be viewed as a "real-time" regulator of physiological functions which extracts features from the environment and, based on that information, allocates an organisms' internal resources to perform physiological functions for the benefit of the organism, e.g., responds to environment conditions in a manner that is advantageous to the organism.

The ANS conveys sensory impulses to and from the central nervous system to various structures of the body such as organs and blood vessels, in addition to conveying sensory impulses through reflex arcs. For example, the ANS controls constriction and dilatation of blood vessels; heart rate; the force of contraction of the heart; contraction and relaxation of smooth muscle in various organs; lungs; stomach; colon; bladder; visual accommodation, secretions from exocrine and endocrine glands, etc. The ANS does this through a series of nerve fibers and more specifically through efferent and afferent nerves. The ANS acts through a balance of its two components: the sympathetic nervous system and parasympathetic nervous system, which are two anatomically and functionally distinct systems. Both of these systems include myelinated preganglionic fibers which make synaptic connections with unmyelinated postganglionic fibers, and it is these fibers which then innervate the effector structure. These synapses usually occur in clusters called ganglia. Most organs are innervated by fibers from both divisions of the ANS, and the influence is usually opposing (e.g., the vagus nerve slows the heart, while the sympathetic nerves increase its rate and contractility), although it may be parallel (e.g., as in the case of the salivary glands). Each of these is briefly reviewed below.

The Parasympathetic System

The parasympathetic nervous system is the part of the autonomic nervous system controlling a variety of autonomic functions including, but not limited to, involuntary muscular movement of blood vessels and gut and glandular secretions from eye, salivary glands, bladder, rectum and genital organs. The vagus nerve is part of the parasympathetic system. Parasympathetic nerve fibers are contained within the last five cranial nerves and the last three spinal nerves and terminate at parasympathetic ganglia near or in the organ they supply. The actions of the parasympathetic system are broadly antagonistic to those of the sympathetic system, lowering blood pressure, slowing heartbeat, stimulating the process of digestion etc. The chief neurotransmitter in the parasympathetic system is acetylcholine.

More specifically, neurons of the parasympathetic nervous system emerge from the brainstem as part of the Cranial nerves III, VII, IX and X (vagus nerve) and also from the sacral region of the spinal cord via Sacral nerves 2, 3 and 4. Because of these origins the parasympathetic nervous system is often referred to as the 'craniosacral outflow'.

In the parasympathetic nervous system both pre- and postganglionic neurons are cholinergic (i.e., they utilize the neurotransmitter acetylcholine) Unlike adrenaline and noradrenaline, which the body takes around 90 minutes to metabolize, acetylcholine is rapidly broken down after release by the enzyme cholinesterase. As a result the effects are relatively brief in comparison to the sympathetic nervous system.

Each preganglionic parasympathetic neuron synapses with just a few postganglionic neurons, which are located near—or in—the effector organ, a muscle or gland. As noted above, the primary neurotransmitter in the parasympathetic system is acetylcholine ("Ach") such that ACh is the neurotransmitter at all the pre- and many of the postganglionic neurons of the parasympathetic system. However, some of the postganglionic neurons release nitric oxide as their neurotransmitter.

The Sympathetic System

The sympathetic nervous system is the part of the autonomic nervous system comprising nerve fibers that leave the spinal cord in the thoracic and lumbar regions and supply viscera and blood vessels by way of a chain of sympathetic ganglia running on each side of the spinal column which communicate with the central nervous system via a branch to a corresponding spinal nerve. The sympathetic nervous system controls a variety of autonomic functions including, but not limited to, control of movement and secretions from viscera and monitoring their physiological state, stimulation of the sympathetic system inducing e.g. the contraction of gut sphincters, heart muscle and the muscle of artery walls, and the relaxation of gut smooth muscle and the circular muscles of the iris. The chief neurotransmitter in the sympathetic system is adrenaline which is liberated in the heart, visceral muscle, glands and internal vessels, with acetylcholine acting as a neurotransmitter at ganglionic synapses and at sympathetic terminals in skin and skeletal muscle blood vessels. The actions of the sympathetic system tend to be antagonistic to those of the parasympathetic system.

More specifically, the preganglionic motor neurons of the sympathetic system arise in the spinal cord. They pass into sympathetic ganglia which are organized into two chains that run parallel to and on either side of the spinal cord. The neurotransmitter of the preganglionic sympathetic neurons is acetylcholine ("Ach") which stimulates action potentials in the postganglionic neurons.

The neurotransmitter released by the postganglionic neurons is nonadrenaline (also called norepinephrine). The action of noradrenaline on a particular structure such as a gland or muscle is excitatory is some cases, inhibitory in others. At excitatory terminals, ATP may be released along with noradrenaline.

Activation of the sympathetic system may be characterized as general because a single preganglionic neuron usually synapses with many postganglionic neurons and the release of adrenaline from the adrenal medulla into the blood ensures that all the cells of the body will be exposed to sympathetic stimulation even if no postganglionic neurons reach them directly.

As indicated above, embodiments of the subject invention provides methods of treating a subject for a condition caused by an abnormality in the subject's autonomic nervous system by electrically modulating at least a portion of the subject's autonomic nervous system to increase the parasympathetic activity/sympathetic activity ratio or increase parasympathetic activity relative to sympathetic activity. By "electrically modulating at least a portion of a subject's autonomic nervous system" is meant altering or changing at least a portion of an autonomic nervous system by electrical means to provide a change, alteration or shift in at least one component or aspect of the autonomic nervous system, as will be described in greater detail below. The modulation of the autonomic nervous system may affect central motor output and/or nerve conduction and/or transmitter release and/or synaptic transmission and/or receptor activation, but in any event is a change that provides an increase in the parasympathetic activity/sympathetic activity ratio (as used herein, "activity" and "function" are used interchangeably). For example, at least a portion of the autonomic nervous system may be electrically modulated to alter, shift or change parasympathetic activity and/or sympathetic activity from a first state to a second state, where the second state is characterized by an increase in the parasympathetic activity/sympathetic activity ratio relative to the first state. In certain embodiments, the subject invention provides methods of increasing activity in at least one parasympathetic nerve fiber to achieve an increase in the parasympathetic activity/sympathetic activity ratio. In certain embodiments the subject invention provides methods of inhibiting activity in at least one sympathetic nerve fiber to achieve an increased parasympathetic activity relative to sympathetic activity. Still further, in certain embodiments the subject invention provides methods of both increasing activity in at least one parasympathetic nerve fiber and inhibiting activity in at least one sympathetic nerve fiber to achieve the desired result. Certain embodiments include electrically stimulating, e.g., with long-term low frequency stimulation, to inhibit or depress activity in the sympathetic nervous system.

Accordingly, a feature of embodiments of the subject methods is that the ratio of parasympathetic activity to sympathetic activity is increased. By increased ratio of parasympathetic activity to sympathetic activity is meant that this ratio is increased in at least a portion of the autonomic nervous system, where the increase is at least great enough to treat a given condition. While the ratio of parasympathetic function/sympathetic function is increased, the net result may be a parasympathetic bias (i.e., parasympathetic dominance), sympathetic bias (i.e., sympathetic dominance) or the activities of the parasympathetic system and sympathetic system may be equal (i.e., neither is dominant).

In practicing embodiments of the subject methods, at least a portion of a subject's autonomic nervous system is electrically modulated to increase parasympathetic activity relative to sympathetic activity (i.e., increase parasympathetic activity/sympathetic activity ratio). As noted above, the electrical modulation may provide an increase in function of at least a portion of the autonomic system, e.g., increase function in at least one parasympathetic nerve fiber, and/or provide a decrease in function or dampening of a portion of the autonomic system, e.g., may inhibit activity in at least one sympathetic nerve fiber or inhibit nerve pulse transmission. As the subject methods electrically modulate at least a portion of a subject's autonomic nervous system, the electrical modulation may be systemic or regional (i.e., local). In other words, the entire parasympathetic and/or sympathetic systems may be modulated or only a portion of the parasympathetic and/or sympathetic systems may be modulated, but in any event at least one parasympathetic and/or sympathetic nerve fiber is affected in a particular manner to the desired increase in parasympathetic activity relative to sympathetic activity. As will be described in greater detail below, any part of the subject methods may be performed manually or automatically.

Increasing Activity in at Least a Portion of the Parasympathetic Nervous System

As noted above, in certain embodiments activity in at least a portion of the parasympathetic system may be increased to modulate at least a portion of the autonomic nervous system. For example, any portion of the parasympathetic system, e.g., one or more nerve fibers, may be electrically stimulated to increase parasympathetic activity to provide the desired ratio of parasympathetic/sympathetic activity. In other words, activity in at least a portion of the parasympathetic nervous system may be increased by electrical stimulation such that at least a portion of the parasympathetic nervous system may be "up-regulated".

Increasing activity in, or up-regulating, at least a part of the parasympathetic system may be desired in instances where, prior to the electrical stimulation of, e.g., the at least one parasympathetic nerve fiber, sympathetic activity is higher than parasympathetic activity (i.e., there exists a relative sympathetic bias) and as such the subject methods may be employed to increase parasympathetic activity to a level above or rather to a level that is greater than sympathetic activity or may be employed to modulate the differential between the parasympathetic-sympathetic systems such that the result of increasing parasympathetic activity may be a sympathetic bias, parasympathetic bias or may be an equalization of the two systems (i.e., the activities of the two systems are approximately equal—including equal), but the difference between the parasympathetic-sympathetic systems may be modulated, e.g., reduced or minimized or increased in certain embodiments. Accordingly, the subject methods may be employed to increase parasympathetic activity above that of sympathetic activity and/or may be employed to modulate (increase or decrease) the differential between the two systems, but in any event is employed to increase the ratio of parasympathetic activity to sympathetic activity. In those instances where there exists a sympathetic bias prior to increasing parasympathetic activity, the cause of the sympathetic bias may be manifold, e.g., hyperthermia, infection, inflammation and fever are potential causes of sympathetic bias (see for example Rowell L B. Hyperthermia: a hyperadrenergic state. Hypertension 1990; 15(5):505-507). In certain embodiments, a sympathetic bias maybe the normal state, but the ratio of the two systems may be abnormal. Furthermore, increasing parasympathetic bias may also be desired in instances where, prior to the electrical stimulation of, e.g., the at least one parasympathetic nerve fiber, to increase parasympathetic activity, parasympathetic activity is higher than the sympathetic activity, but the differential between the two needs to be modulated such as increased further, e.g., the sympathetic activity is normal or above normal (i.e., abnormally high) and/or the parasympathetic activity is normal or below normal (i.e., abnormally low) or above normal (i.e., abnormally low). For example, such instances may occur where a subject has normal or above normal parasympathetic function, but also has elevated sympathetic function. Other instances include below normal parasympathetic function, but normal or elevated sympathetic function, etc. It may also be desirable to increase parasympathetic function in instances where the respective activities of the two system are analogous or approximately equal, including equal, prior to increasing activity in the parasympathetic system, but the level of one or both is abnormally high or abnormally low. The above-described examples of instances where increasing parasympathetic activity may be desired is exemplary only and is in no way intended to limit the scope of the invention and other instances where increasing parasympathetic activity to provide an increase in the parasympathetic activity/sympathetic activity ratio may be desired will be apparent to those of skill in the art.

Specifically, activity in at least a portion of the parasympathetic system, e.g., one or more nerve fibers associated with the parasympathetic system, is increased by an electrostimulatory device positioned directly on or about (i.e., adjacent) the targeted area of the parasympathetic system, as will be described in greater detail below. Accordingly, in practicing the subject methods to increase the parasympathetic activity/sympathetic activity ratio by increasing activity in at least one area of the parasympathetic system such as a nerve fiber, an electrostimulatory device is operatively positioned directly on or about the one or more parasympathetic nerve fibers to which an increase in activity is desired.

The actual area(s) of the parasympathetic nervous system that will be electrically stimulated will vary in accordance with the subject invention, and include pre- and post ganglionic nerve fibers, as well as ganglionic structures, efferent and afferent nerve fibers, synapses, etc., and combinations thereof in certain embodiments. In certain embodiments, a given nerve fiber may be electrically stimulated in more than one area of the nerve fiber. Targeted areas of the parasympathetic nervous system which may be electrically stimulated in accordance with the subject invention include, the oculomotor nerve; facial nerve; glossopharyngeal nerve; hypoglossal nerve; trigeminal nerve, vagus nerve including the recurrent laryngeal branches of the vagus nerve, the pharyngeal and superior laryngeal branches of the vagus nerve, the cardiac branches of the vagus nerve, the anterior vagal trunk and the posterior vagal trunk; ciliary ganglion; pterygophalatine ganglion; vidian nerve, pterygopalatine nerve, otic ganglion; chorda tympsubmandibular ganglion; lingual nerve; submandibular ganglion; esophageal plexus; parasympathetic branch from inferior hypogastric plexus to descending colon; rectal plexus and pelvic planchnic nerves, or a combination of two or more of the above. For example, in certain embodiments electrical stimulation to the vagus may be employed and/or to the hypoglossal nerve and/or to the trigeminal nerve.

Once an electrostimulatory device is positioned in a suitable position on or about one or more targeted parasympathetic areas such as one or more parasympathetic nerve fibers, the area(s) (e.g., the targeted nerve fiber(s)) are electrically stimulated for a period of time sufficient to provide the desired increase in parasympathetic activity. This period of time will vary depending on the area (e.g., the nerve fiber) being treated, the condition being treated, etc. Certain embodiments include simultaneously monitoring (i.e., in "real time") the parasympathetic activity (and/or sympathetic activity) such that a given nerve fiber is electrically stimulated until the desired increase in parasympathetic activity (parasympathetic activity/sympathetic activity balance) is observed. Still further, in many embodiments once the desired increase in parasympathetic activity is achieved, a given area of the parasympathetic system (e.g., a given parasympathetic nerve fiber) may be repeatedly electrically stimulated one or more times to maintain the desired state such that the subject methods may be repeated one or more times, i.e., the subject methods include chronically stimulating at least one area of the parasympathetic nervous system such as chronically stimulating one or more parasympathetic nerve fibers. For example, in certain embodiments electrical stimulation (e.g., intermittent mild electrical pulses) may be delivered to a given area of the parasympathetic nervous system, e.g., one or more nerve fibers of the parasympathetic system, twenty-four hours a day for a period of days, weeks, months, or even years in certain embodiments.

During the period of time that a given area of the parasympathetic nervous system such as a parasympathetic nervous system nerve fiber is electrically stimulated, the electrical stimulation may be substantially continuous, including continuous or intermittent (i.e., pulsed or periodic), where in many embodiments the electrical stimulation is in the form of electrical pulses. In other words, in certain embodiments a given area of the parasympathetic nervous system (e.g., a given nerve fiber) may be continuously electrically stimulated during the above-described period of time and in certain other embodiments a given area of the parasympathetic nervous system (e.g., a given nerve fiber) may be pulsed or intermittently electrically stimulated during the period of time described above.

In accordance with the subject methods to electrically stimulate at least one area of the parasympathetic nervous system such as at least one parasympathetic nerve fiber, once operatively positioned the electrostimulatory device is activated to provide an electrical signal to the targeted area such as to one or more parasympathetic nerve fiber(s) in a manner to increase the parasympathetic activity at least in the area being electrically stimulated and in certain instances in adjacent areas or in the entire parasympathetic system, e.g., systemically in certain instances. For example, many nerve fibers of the parasympathetic system are in close proximity and thus electrical stimulation to one nerve fiber may also increase activity in one or more other nerve fibers, e.g., nerve fibers in close proximity thereto.

In practicing the subject methods, activation of the electrostimulatory device directly applies the electrical output of the device, i.e., electrical impulses, to the targeted area. The exact parameters of the electrical stimulation may vary depending on the particular subject, condition being treated, etc. Usually, an electronic current wave is provided when the electrical stimulation is applied. In certain embodiments, the current wave includes current waves of high frequency, e.g., high frequency pulses, where the current wave may also include low frequency amplitude modulation. In certain embodiments, a plurality of high frequency bursts of current pulses may be applied in addition to the application of underlying low frequency continuous stimulus. Stimulation may be monopolar or multipolar.

For example, to stimulate a portion of the parasympathetic nervous system, voltage or intensity may range from about 1 millivolt to about 1 volt or more, e.g., 0.1 volt to about 50 volts, e.g., from about 0.2 volt to about 20 volts and the frequency may range from about 1 Hz to about 2500 Hz, e.g., about 1 Hz to about 1000 Hz, e.g., from about 2 Hz to about 100 Hz in certain embodiments. In certain embodiments a pure d-c voltages may be employed. The pulse width may range from about 1 microsecond to about 2000 microseconds or more, e.g., from about 10 microseconds to about 2000 microseconds, e.g., from about 15 microseconds to about 1000 microseconds, e.g., from about 25 microseconds to about 1000 microseconds. The electrical output may be applied for at least about 1 millisecond or more, e.g., about 1 second, e.g., about several seconds, where in certain embodiments the stimulation may be applied for as long as about 1 minute or more, e.g., about several minutes or more, e.g., about 30 minutes or more may be used in certain embodiments.

Certain embodiments may include providing long-term potentiation ("LTP") of at least a portion of the parasympathetic nervous system. LTP may be characterized as an enduring increase in synaptic efficacy resulting from high-frequency stimulation of an afferent (input) pathway. For example, long-term high frequency stimulation of at least a portion of the parasympathetic system may be employed to achieve parasympathetic bias. More specifically, rapid, intense electrical stimulation of presynaptic neurons associated with the parasympathetic system may be employed to evoke action potentials in one or more postsynaptic neurons such that over time these synapses become increasingly sensitive. This constant level of presynaptic stimulation eventually becomes converted into a larger postsynaptic output which may last for minutes, hours, days, even weeks or more.

In certain embodiments the subject methods may also include detecting information related to one or more aspects of the autonomic nervous system such as a physical and/or chemical aspect, e.g., activity, balance, etc., in at least a portion of the autonomic nervous system and evaluating this information to determine the state of the autonomic nervous system, e.g., the parasympathetic activity and/or sympathetic activity. Once the state of the autonomic nervous system is determined, it may be evaluated in regards to whether the autonomic nervous system is in an abnormal state or in need of modulation, e.g., whether activity in at least a portion of the parasympathetic system needs to be increased to increase the parasympathetic activity/sympathetic activity ratio such that this analysis may be employed as a "trigger" to providing electrical modulation of at least a portion of the autonomic nervous system wherein modulation is not performed unless the analysis determined such is necessary. Accordingly, collecting and evaluating this type of data and relating it to whether modulation is required may be employed as a "trigger" to electrically modulating at least a portion of the autonomic nervous system (e.g., performed prior to, during or following a stimulation protocol) such that such data may indicate whether, when, etc., electrical modulation is required—if at all. For example, in certain embodiments electrical modulation of at least a portion of a subject's autonomic nervous system is not performed unless one or more aspects of the autonomic nervous system are detected and indicate such modulation is necessary. Any suitable physical and/or chemical aspect or indicator of the autonomic nervous system may be employed, e.g., conduction, catecholamine levels, heart rate variability ("HRV"), action potentials, QT interval, etc. In certain embodiments, detection may include detecting the activity or function of a particular organ or system under the control of the autonomic nervous system such as detecting rennin levels for the digestive system, etc. Any suitable detection means may be employed to detect relevant information about the autonomic nervous system, as will be described below.

In certain embodiments, a control feedback loop is provided. For example, during or following a particular stimulation protocol, the parasympathetic activity (and/or sympathetic activity) may be monitored, e.g., by sensing conduction in at least a portion of the parasympathetic system, e.g., in a particular electrically stimulated nerve fiber, or by any suitable method. Other methods that may be employed to monitor the autonomic balance include, but are not limited to, neurography, continuous or serial measurements of circulating catecholamine levels, heart rate variability ("HRV"), post-ganglionic action potentials, QT interval, and the like (see for example Rang S, Wolf H, Montfrans G A, Karemaker J M. Non-invasive assessment of autonomic cardiovascular control in normal pregnancy and pregnancy-associated hypertensive disorders: a review. J Hypertens 2002;20(11):2111-9). For example, a sensor suitable for detecting nerve cell or axon activity that are related to the autonomic nervous system may be implanted in a portion of a subject's body. A sensor may take the form of an electrode or the like. Signals received by such a sensor may be amplified before further processing. A sensor may also take the form of a device capable of detecting nerve compound action potentials or may take the form of a transducer that includes an electrode with an ion selective coating applied which is capable of directly transducing the amount of a particular transmitter substance or its breakdown by-products. In utilizing a feedback system, if the desired increase in parasympathetic activity is not detected, e.g., prior to, during or after a particular stimulus is applied to the parasympathetic system, the same or a different stimulus protocol may be performed. For example, in those instances where a different protocol is performed, one or more of the stimulus parameters may be modified, e.g., the pulse width may be increased, or the like, in the second protocol.

Inhibiting Activity in at Least a Portion of the Sympathetic Nervous System

As noted above, in certain embodiments activity in at least a portion of the sympathetic system may be inhibited to modulate at least a portion of the autonomic nervous system. For example, activity in any portion of the sympathetic nervous system may be inhibited to increase parasympathetic activity relative to sympathetic activity to provide the desired ratio of parasympathetic/sympathetic activity, e.g., activity in one or more sympathetic nerve fibers may be inhibited. By "inhibited" is meant to include disruption, down-regulating, dampening and partial and complete blockage of nerve impulses in a particular area of the sympathetic system.

Inhibiting or "down-regulating" activity in at least a part of the parasympathetic system may be desired in instances where, prior to the inhibition of activity in, e.g., at least one sympathetic nerve fiber, the sympathetic activity is higher than desired. For example, sympathetic activity may be higher than the parasympathetic activity (i.e., there exists a sympathetic bias) or sympathetic activity may be less than or approximately equal to, including equal, to parasympathetic activity, and the subject methods may be employed to modulate the differential between the parasympathetic-sympathetic systems such that the result of decreasing sympathetic activity may be a sympathetic bias, parasympathetic bias or may be an equalization of the two systems (i.e., the activities of the two systems are approximately equal—including equal), but the difference between the parasympathetic-sympathetic systems may be modulated, e.g., increased or reduced in certain embodiments. Accordingly, the subject methods may be employed to decrease sympathetic activity below that of sympathetic activity and/or may be employed to modulate (decrease or increase) the differential between the two systems, but in any event is employed to increase the ratio of parasympathetic activity to sympathetic activity. For example, decreasing activity in at least a portion of the sympathetic system may be employed where there is a normal or an abnormally low parasympathetic function and/or abnormally high sympathetic function. Such may also be desired in instances where, prior to decreasing sympathetic function in, e.g., at least one sympathetic nerve fiber, parasympathetic activity is higher than the sympathetic activity, but the differential between the two needs to be increased further. For example, such instances may occur where a subject has normal or above normal (i.e., abnormally high) parasympathetic function, but also has elevated sympathetic function (i.e., abnormally high), e.g., a relative bias towards sympathetic function may be present. Other instances include normal or below normal (i.e., abnormally low) parasympathetic activity and/or normal or above normal (i.e., abnormally high) sympathetic activity. The above-described examples of instances where decreasing sympathetic activity may be desired is exemplary only and is in no way intended to limit the scope of the invention and other instances where decreasing sympathetic activity to provide an increase in the parasympathetic activity/sympathetic activity ratio may be desired will be apparent to those of skill in the art.

Inhibiting or down-regulating at least a portion of the sympathetic nervous system may be accomplished in a number of ways. For example, inhibition or down-regulation of activity may be achieved by surgically isolating an effector structure (i.e., the target of the sympathetic activity) from sympathetic innervation, i.e., surgically isolating an effector structure from one or more sympathetic nerve fibers associated with it. Furthermore, sympathetic nerves may be ablated, permanently or reversibly, by employing energy delivery devices or cryotherapy. Certain embodiments may employ cryoablation, thermoablation, microwave energy, focus ultrasound, magnetic fields including internal and external magnetic fields, laser energy, optical energy, radiofrequency energy, and the like. The sympathetic system may also be inhibited or down-regulated or depressed by employing pacing mechanisms such as implantable electrode-based pacing systems, external magnetic-based pacing system, and the like. Certain embodiments may include inhibiting activity in at least a portion of the sympathetic nervous system using transcutaneous electrical nerve stimulation ("TENS") or transmagentic stimulation ("TMS") (see for example George, M. Stimulating the Brain. Sci Amer 2003 September). Still further, pharmacological agents such as neurotoxins may be employed to disable sympathetic function such that the parasympathetic to sympathetic ratio is increased temporarily or permanently. In any event, activity in at least a portion of the sympathetic system, e.g., one or more nerve fibers associated with the sympathetic system, is inhibited. In many embodiments, this inhibition is achieved by employing an electrostimulatory device positioned directly on or about (i.e., adjacent) the targeted area of the sympathetic system, as will be described in greater detail below. Accordingly, in practicing the subject methods to increase parasympathetic activity relative to sympathetic activity by inhibiting activity in at least one area of the sympathetic system such as a nerve fiber, an electrostimulatory device may be operatively positioned directly on or about the one or more sympathetic nerve fibers desired to be inhibited.

The actual area(s) of the sympathetic nervous system that will be inhibited will vary, and include pre- and post ganglionic nerve fibers, ganglionic structures, efferent and afferent nerve fibers, etc. In certain embodiments, a given nerve fiber may be electrically inhibited in more than one area of the nerve fiber. Targeted areas of the sympathetic nervous system which may be inhibited or dampened in accordance with the subject invention include, internal carotid nerve and plexus, middle and superior cervical sympathetic ganglion; vertebral ganglion; cervicothoracic ganglion; sympathetic trunk; cervical cardiac nerves; cardiac plexus; thoracic aortic plexus; celiac ganglion; celiac trunk and plexus; superior mesenteric ganglion; superior mesenteric artery and plexus; intermesenteric plexus; inferior mesenteric ganglion; inferior mesenteric artery and plexus; superior hypogastric plexus; hypogastric nerves; vesical plexus; thoracic cardiac nerves; sympathetic trunk; 6th thoracic sympathetic ganglion; gray and white rami communicantes; greater, lesser and least splanchnic nerves; aorticorenal ganglion; lumbar splanchnic nerves; gray rami communicantes and sacral splanchnic nerves; or a combination of two or more of the above.

In practicing the subject methods to inhibit sympathetic activity, once an electrostimulatory device is positioned in a suitable position on or about one or more targeted sympathetic areas such as one or more sympathetic nerve fibers, an electrical output, impulse or signal is applied for a period of time sufficient to provide the desired inhibition and thus the desired ratio of parasympathetic activity to sympathetic activity. This period of time will vary depending on the area (e.g., the nerve fiber) being inhibited and the desired degree of inhibition, the condition being treated, etc.

Analogous to that described above in regards to monitoring activity in at least a portion of the parasympathetic system, certain embodiments include simultaneously monitoring (i.e., in "real time") the inhibition in the targeted area or sympathetic activity (and/or parasympathetic activity) such that an electrical output or impulse is applied to a given nerve fiber until the desired inhibition in activity (parasympathetic activity/sympathetic activity balance) is observed. Still further, in many embodiments once the desired increase in parasympathetic activity is achieved by inhibiting activity in a portion of the sympathetic nervous system, a given area of the sympathetic system (e.g., a given sympathetic nerve fiber) may be repeatedly subjected to electrical impulses one or more times to maintain the desired state such that the subject methods may be repeated one or more times, i.e., the subject methods include chronically applying electrical impulses to at least one area of the sympathetic nervous system. For example, in certain embodiments electrical impulses (e.g., intermittent mild electrical pulses) may be delivered to a given area of the sympathetic nervous system, e.g., one or more nerve fibers of the sympathetic system) twenty-four hours a day for a period of days, weeks, months, or even years in certain embodiments.

During the period of time that the activity in a given area of the sympathetic nervous system, such as a sympathetic nervous system nerve fiber, is inhibited, the electrical impulses may be applied substantially continuously, including continuously or intermittently (i.e., pulsed or periodic). In other words, in certain embodiments a given area of the sympathetic nervous system may be subjected to continuously applied electrical impulses during the above-described period of time and in certain other embodiments a given area of the sympathetic nervous system may be pulsed or intermittently electrically inhibited during the period of time described above.

In accordance with the subject methods to inhibit activity in at least one area of the sympathetic nervous system such as at least one sympathetic nerve fiber, once operatively positioned the electrostimulatory device is activated to provide an electrical impulse to the targeted area such as one or more sympathetic nerve fiber(s) in a manner to modulate the sympathetic activity in at least in the area being subjected to the electrical impulses and in certain instances in adjacent areas, e.g., systemically in certain instances.

Activation of the electrostimulatory device directly applies the electrical output, i.e., electrical impulses, of the device to the targeted area to inhibit activity. The exact parameters of the electrical impulse may vary depending on the particular subject, condition being treated, etc. In certain embodiments, a negative current wave is provided and employed to inhibit sympathetic activity. In certain embodiments, the current wave includes current waves of high frequency, e.g., high frequency pulses, where the current wave may also include low frequency amplitude modulation. In certain embodiments, a plurality of high frequency bursts of current pulses may be applied in addition to the application of underlying low frequency continuous stimulus. Monopolar or bipolar technologies may be employed.

For example, to inhibit conduction in a portion of the sympathetic nervous system, voltage or intensity may range from about 1 millivolt to about 1 volt or more, e.g., 0.1 volt to about 50 volts, e.g., from about 0.2 volt to about 20 volts and the frequency may range from about 1 Hz to about 2500 Hz, e.g., about 50 Hz to about 2500 Hz. In certain embodiments a pure d-c voltages may be employed. The pulse width may range from about 1 microseconds to about 2000 microseconds or more, e.g., from about 10 microseconds to about 2000 microseconds, e.g., from about 15 microseconds to about 1000 microseconds, e.g., from about 25 microseconds to about 1000 microseconds. The stimulation may be applied for at least about 1 millisecond or more, e.g., about 1 second, e.g., about several seconds, where in certain embodiments the electrical energy may be applied for as long as about 1 minute or more, e.g., about several minutes or more, e.g., about 30 minutes or more may be used in certain embodiments.

In certain embodiments, electrical stimulation of at least a portion of the sympathetic system may be employed to depress signal in the sympathetic system over a long period of time. For example, long-term depression ("LTD") may be achieved by applying long-term low frequency stimulation to at least a portion of the sympathetic system to provide long-term sympathetic suppression. Specifically, slow, weak stimulation may be applied to at least a portion of the sympathetic system, e.g., neurons of the sympathetic system, to bring about long-term changes in the synapses, such as a reduction in sensitivity.

As described above in regards to detecting aspects of the parasympathetic system, certain embodiments of the subject methods may also include detecting information related to one or more physical and/or chemical aspects or states of the autonomic nervous system, e.g., activity, balance, etc., in at least a portion of the autonomic nervous system and evaluating this information to determine the state of the autonomic nervous system, e.g., the parasympathetic activity and/or sympathetic activity. Once the state of the autonomic nervous system is determined, it may be evaluated in regards to whether the autonomic nervous system is in an abnormal state or in need of modulation, e.g., whether activity in at least a portion of the sympathetic needs to be inhibited to increase parasympathetic activity relative to sympathetic activity. Accordingly, analogous methods as those described above may be applied to detecting one or more aspects of the sympathetic system and determining whether inhibition in activity in at least a portion of the sympathetic system is required, e.g., prior to, during or after a given inhibition protocol has been performed.

Analogous to that described for the electrical stimulation of a portion of the parasympathetic nervous system, in certain embodiments of inhibiting sympathetic activity a control feedback loop is provided. For example, during or following a particular inhibition protocol, the amount of activity that is inhibited and/or the resultant sympathetic activity and/or parasympathetic activity may be monitored, e.g., by sensing activity in at least a portion of the sympathetic system. Other methods that may be employed to monitor the autonomic balance include, but are not limited to, neurography, continuous or serial measurements of circulating catecholamine levels, heart rate variability ("HRV"), post-ganglionic action potentials, QT interval, and the like (see for example Rang S, Wolf H, Montfrans G A, Karemaker J M. Non-invasive assessment of autonomic cardiovascular control in normal pregnancy and pregnancy-associated hypertensive disorders: a review. J Hypertens 2002;20(11):2111-9). A sensor analogous to that described above may be employed. For example, a sensor suitable for detecting nerve cell or axon activity that are related to the autonomic nervous system may be implanted in a portion of a subject's body. A sensor may take the form of an electrode. Signals received by such a sensor may be amplified before further processing. A sensor may also take the form of a device capable of detecting nerve compound action potentials or may take the form of a transducer that includes an electrode with an ion selective coating applied which is capable of directly transducing the amount of a particular transmitter substance or its breakdown by-products. In utilizing a feedback system, if the desired increase in parasympathetic activity is not achieved, the same or a different stimulus protocol may be performed. In utilizing such a feedback system, if the desired inhibition in activity or level of sympathetic activity is not achieved, the same or a different protocol for inhibiting activity may be performed. For example, in those instances where a different protocol is performed, one or more of the protocol parameters may be modified, e.g., the pulse width may be increased, or the like, in the second protocol.

Increasing Activity in at Least a Portion of the Parasympathetic Nervous System and Inhibiting Activity in at Least a Portion of the Sympathetic Nervous System As noted above, in certain embodiments activity in at least a portion of the parasympathetic system may be increased and activity-in at least a portion of the sympathetic system may be inhibited to increase the parasympathetic activity/sympathetic activity ratio. For example, as described above any portion of the parasympathetic nervous system may be electrically stimulated to increase activity and activity in any portion of the sympathetic nervous system may be inhibited to provide the desired ratio of parasympathetic activity to sympathetic activity, e.g., one or more nerve fibers of the parasympathetic system may be electrically stimulated to increase activity and/or the activity in one or more nerve fibers of the sympathetic system may be inhibited. Such a protocol may be employed, e.g., in instances where parasympathetic function is normal or abnormally low and/or sympathetic function is normal or abnormally high where normal is determined by the typical autonomic nervous system functions for a healthy subject, e.g., a healthy human subject ranging in age from about 20 years old to about 25 years old. Such embodiments may be employed to alter the dominance and/or may be employed to modulate the differential between the two systems. For example, prior to modulating the autonomic system according to the subject invention, the activity in the sympathetic system may be higher than activity in the parasympathetic system and the subject methods may be employed to increase the parasympathetic activity to a level that is greater than the sympathetic activity and/or may be employed to alter the differential or difference in activity levels of the two systems such as decreasing the difference in activity levels or increasing the difference in activity levels. In other embodiments, prior to modulating the autonomic system according to the subject invention, the activity in the parasympathetic system may be higher than activity in the sympathetic system and the subject methods may be employed to alter the differential or difference in activity levels of the two systems such as increasing the difference in activity levels. The above-described examples of instances where increasing activity in at least a portion of the parasympathetic system and decreasing activity in at least a portion of the sympathetic activity may be desired is exemplary only and is in no way intended to limit the scope of the invention and other instances where increasing activity in at least a portion of the parasympathetic system and decreasing activity in at least a portion of the sympathetic activity may be desired will be apparent to those of skill in the art.

Increasing activity in at least a portion of the parasympathetic system and decreasing activity in at least a portion of the sympathetic system may be performed simultaneously or sequentially such that at least a portion of the parasympathetic nervous system may be electrically stimulated to increase activity therein prior or subsequent to inhibiting activity in at least a portion of the sympathetic nervous system. Regardless of whether increasing activity in at least a portion of the parasympathetic system and decreasing activity in at least a portion of the sympathetic system are performed simultaneously or sequentially, the parameters for increasing activity in at least a portion of the parasympathetic system and decreasing activity in at least a portion of the sympathetic system are analogous to that described above.

Pharmacological Modulation of the Autonomous Nervous System

In certain embodiments, the subject methods include pharmacologically modulating a subject's autonomic nervous system. Such pharmacological modulation may be performed prior to and/or at the same time as and/or subsequent to electrical modulation as described above. Certain embodiments include administering an effective amount of one or more pharmacological agents to a subject in manner effective to modulate the subject's ANS to treat the subject for a condition. This may be in addition to electrical modulation or instead of electrical modulation (i.e., without any electrical modulation). As such, pharmacological modulation of a subject's ANS may be alone or in combination with one or more other treatment protocols such as electrical modulation. The pharmacological modulation may be employed to achieve results analogous to those described above for electrical modulation, e.g., an increase in the parasympathetic activity/sympathetic activity ratio in at least a portion of as subject's ANS and/or an decrease in the parasympathetic activity/sympathetic activity ratio in at least a portion of as subject's ANS. That is, in certain embodiments the subject methods may include administering an effective amount of one or more autonomic nervous system modulating pharmacological agents to a subject to modulate the subject's autonomic nervous system. By effective amount is meant a dosage sufficient to modulate at least a portion of a subject's autonomic nervous system for a given period of time. The one or more pharmacological agents may be administered prior to any electrical stimulation of at least a portion of the autonomic nervous system that may be performed and/or prior to any electrical inhibition of activity in at least a portion of the autonomic nervous system that may be performed. Furthermore, the one or more pharmacological agents may be administered simultaneously with any electrical stimulation of at least a portion of the autonomic nervous system that may be performed and/or simultaneously with any electrical inhibition of activity in at least a portion of the autonomic nervous system that may be performed. Still further, the one or more pharmacological agents may be administered subsequent to any electrical stimulation of at least a portion of the autonomic nervous system that may be performed and/or subsequent to any electrical inhibition of activity in at least a portion of the autonomic nervous system that may be performed.

Depending on the nature of the pharmacological agent, the active agent(s) may be administered to the subject using any convenient means capable of resulting in the desired modulation of the autonomic nervous system, where the desired modulation may include an increase in the parasympathetic activity/sympathetic activity ratio and/or a decrease in the parasympathetic activity/sympathetic activity ratio. In certain embodiments, ANS modulation may include increasing the parasympathetic activity/sympathetic activity ratio and decreasing the parasympathetic activity/sympathetic activity ratio, e.g., at different portions of the ANS or at different times. Thus, the pharmacological agent may be incorporated into a variety of formulations for therapeutic administration. More particularly, the agents of the present invention may be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. As such, administration of the agents can be achieved in various ways, including oral, buccal, rectal, parenteral, intraperiactivityal, intradermal, transdermal, intracheal, etc., administration.

In pharmaceutical dosage forms, the agents may be administered alone or in appropriate association, as well as in combination, with other pharmaceutically active compounds. The following methods and excipients are merely exemplary and are in no way limiting.

For oral preparations, the agents may be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents may be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents may be utilized in aerosol formulation to be administered via inhalation. The compounds of the present invention may be formulated into pressurized acceptable propellants such as dichlorodifluoromethane, propane, nitrogen and the like.

Furthermore, the agents may be made into suppositories by mixing with a variety of bases such as emulsifying bases or water-soluble bases. The compounds of the present invention may be administered rectally via a suppository. The suppository may include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of a pharmacological agent. Similarly, unit dosage forms for injection or intravenous administration may include the pharmacological agent(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of pharmacological agent(s) of the present invention calculated in an amount sufficient to produce the desired effect in association with a pharmaceutically acceptable diluent, carrier or vehicle. The specifications for the novel unit dosage forms of the present invention depend on the particular pharmacological agent(s) employed and the effect to be achieved, and the pharmacodynamics associated with each pharmacological agent(s) in the subject.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Those of skill in the art will readily appreciate that dose levels may vary as a function of the specific pharmacological agent(s), the nature of the delivery vehicle, and the like. Dosages for a given pharmacological agent(s) are readily determinable by those of skill in the art by a variety of means.

Introduction of an effective amount of a pharmacological agent(s) into a subject as described above results in a modulation of the autonomic nervous system, where the modulation may be temporary or permanent.

A wide variety of different pharmacological agents may be employed-in the practice of the subject methods, where the particular pharmacological agent(s) employed to modulate the autonomic nervous system to increase parasympathetic activity relative to sympathetic activity will depend on the subject being treated, the condition being treated, whether it is desired to increase activity in the parasympathetic system and/or decrease activity in the sympathetic system, etc. Representative pharmacological agents include, but are not limited to, magnesium and magnesium variants, e.g., magnesium sulfate; cholinergics, e.g., Bethanechol, Oxotremorine, Methacholine, Cevimeline; Acetylcholinesteriase inhibitors, e.g., Edrophonium, Neostigmine, Donepezil, Tacrine, Echothiophate, Diisopropylfluorophosphate, Demecarium, Pralidoxime, Galanthamine, Tetraethyl pyrophosphate, Parathoin, Malathion, Isoflurophate, Metrifonate, Physostigmine, Rivastigmine, Abenonium acetylchol, Carbaryl acetylchol, Propoxur acetylchol, Aldicarb acetylchol; catecholamines inhibitors; nicotine; and muscarinics, e.g., Muscarine, Pilocarpine. For example, neurotoxins such as botox and capsaicin may be employed, e.g., delivered locally, to disable sympathetic function such that the parasympathetic to sympathetic ratio is increased. Accordingly, one or more of the above mentioned pharmacological agents may be used in the practice of the subject invention.

For example, as described in greater detail below, the subject invention find use in the treatment of sleep apnea and other conditions that modulate carbon dioxide levels in circulating blood and/or decrease oxygen levels in circulating blood and/or increase acidity in bodily fluids, i.e., any condition having a manifestation of hypoxia and/or hypercarbia and/or acidosis and/or hypercarbia. Embodiments of the subject invention may include modulating (electrically and/or pharmacologically) at least a portion of the ANS to decrease $pCO_2$ concentration in circulating blood, and/or increase $pO_2$ concentration in circulating blood, and/or decrease pH in bodily fluids, and/or treat a condition having a manifestation of hypoxia and/or hypercarbia and/or acidosis, and/or hypercarbia and/or treat a condition that has resulted or is associated from any of the above (e.g., associated inflammatory conditions).

Accordingly, a wide variety of different pharmacological agents may be employed in the practice of the subject methods to modulate at least a portion of the ANS to treat, e.g., sleep apnea (or other conditions such as any other condition noted herein, but not limited only to conditions described herein), where the particular pharmacological agent or combination of pharmacological agents employed will depend on, e.g., the subject being treated, the condition being treated, duration of treatment, whether it is desired to increase activity in the parasympathetic system and/or increase activity in the sympathetic system and/or decrease activity in the sympathetic system and/or decrease activity in the parasympathetic system, etc. Representative pharmacological agents (and analogs and salts thereof) that may be employed to treat hypoxia and/or hyupercarbia, and/or hypercarbia and/or acidosis and/or a condition having a manifestation thereof or a condition resulting from hypoxia and/or hypercarbia and/or hypercapnia and/or acidosis (e.g., a resultant inflammatory condition) by modulating at least a portion of the ANS, include, but are not limited to, one of more of the following:

beta-blockers (e.g., atenolol (e.g., as sold under the brand names TENORMIN), betaxolol (e.g., as sold under the brand name KERLONE), bisoprolol (e.g., as sold under the brand name ZEBETA), carvedilol (e.g., as sold under the brand name COREG), esmolol (e.g., as sold under the brand name BREVIBLOC), labetalol (e.g., as sold under the brand name NORMODYNE), metoprolol (e.g., as sold under the brand name LOPRESSOR), nadolol (e.g., as sold under the brand name CORGARD), pindolol (e.g., as sold under the brand name VISKEN), propranolol (e.g., as sold under the brand name INDERAL), sotalol (e.g., as sold under the brand name BETAPACE), timolol (e.g., as sold under the brand name BLOCADREN), carvedilol, and the like);

aldosterone antagonists (e.g., spironolactone, eplerenone, and the like);

angiotensin II receptor blockades (e.g., candeartan (e.g., available under the brand name Altacand), eprosarten mesylate (e.g., available under the brand name Tevetan), irbesartan (e.g., available under the brand name Avapro), losartan (e.g., available under the brand name Cozaar), etelmisartin (e.g., available under the brand name Micardis), valsartan (e.g., available under the brand name Diovan), and the like);

angiotensin converting enzyme ("ACE") inhibitors (e.g., benazapril (e.g., available under the brand name Lotensin), captopril (e.g., available under the brand name Capoten) enalapril (e.g., available under the brand name Vasotec) fosinopril (e.g., available under the brand name Monopril) lisinopril (e.g., available under the brand name Prinivil) moexipril (e.g., available under the brand name Univasc) quinapril (e.g., available under the brand name AccupriL)

ramipril (e.g., available under the brand name Altace) trandolapril (e.g., available under the brand name Mavik), and the like);

statins (e.g., atorvastatin (e.g., available under the brand name Lipitor), cerivastatin (e.g., available under the brand name Baycol), fluvastatin (e.g., available under the brand name LlescoL), lovastatin (e.g., available under the brand name Mevacor), prevastatin (e.g., available under the brand name Pravachol), simvastatin (e.g., available under the brand name Zocor), and the like);

triglycerides lowering agents (e.g., fenofibrate (e.g., available under the brand name Tricor), genfibrozil (e.g., available under the brand name Lopid), and the like);

niacin;

diabetes agents (e.g., exenatide, synthetic exendin-4, acarbose (e.g., available under the brand name Precose), glimepiride (e.g., available under the brand name Amaryl), glyburide (e.g., available under the brand names Micronase, Diabeta), metformin (e.g., available under the brand name Glucophasge), miglitol (e.g., available under the brand name Glycet), pioglitazone (e.g., available under the brand name Actos), repaglinide (e.g., available under the brand name Prandin), rosiglitazone (e.g., available under the brand name Avandia), and the like);

immunomodulators (e.g., interferon beta-1B (e.g., available under the brand name Betaseron), interferon alfa-2A (e.g., available under the brand name ROFERON-A) interferon alfa-2B (e.g., available under the brand name INTRON-A), interferon alfa-2B and Ribavirin combo pack (e.g., available under the brand name REBETRON), interferon alfa-N3 (e.g., available under the brand name ALFERON N), interferon beta-1A (e.g., available under the brand name AVONEX), interferon beta-1B, interferon gamma immunoregulatory antibodies that bind to or react with one of the following antigens: CD4, gp39, B7, CD19, CD20, CD22, CD401, CD40, CD40L and CD23, rituximab (e.g., available under the brand name RITUXAN), any chemical or radiopharmaceutical linked or conjugated antibodies that bind to or react with one of the following antigens: CD4, gp39, B7, CD19, CD20, CD22, CD401, CD40, CD40L and CD23), and the like);

nicotine;

sympathomimetics (e.g., trimethaphan, clondine, reserpine, guanethidine, and the like);

antihistamines (e.g., available under the brand name Benadryl, diphenhydramine, available under the brand name Actifed, and the like);

cholinergics (e.g., bethanechol, oxotremorine, methacoline, cevimeline, and the like);

acetylcholinesterase inhibitors (e.g., edrophonium, neostigmine, donepezil, tacrine, echothiophate, diisopropylfluorophosphate, demecarium, pralidoxime, galanthamine, tetraethyl pyrophosphate, parathoin, malathion, isoflurophate, metrifonate, physostigmine, rivastigmine, abenonium acetylchol, carbaryl acetylchol, propoxur acetylchol, aldicarb acetylchol, and the like);

magnesium and magnesium sulfates;

calcium channel blockers (e.g., amlodipine besylate (e.g., available under the brand name Norvasc), diltiazem hydrochloride (e.g., available under the brand names Cardizem CD, Cardizem SR, Dilacor XR, Tiazac), felodipine plendil isradipine (e.g., available under the brand names DynaCirc, DynaCirc CR), nicardipine (e.g., available under the brand name Cardene SR), nifedipine (e.g., available under the brand names Adalat CC, Procardia XL), nisoldipine sulfur (e.g., available under the brand name Sular), verapamil hydrochloride (e.g., available under the brand names Calan SR, Covera HS, Isoptin SR, Verelan) and the like);

muscarinics (e.g., muscarine, pilocarpine, and the like);

sodium channel blockers, (e.g., moricizine, propafenone, encainide, flecainide, tocainide, mexiletine, phenytoin, lidocaine, disopyramide, quinidine, procainamide, and the like);

glucocorticoid receptor blockers (e.g., mifepristone, and the like);

peripheral andrenergic inhibitors (e.g., guanadrel (e.g., available under the brand name Hylorel), guanethidine monosulfate (e.g., available under the brand name Ismelin), reserpine (e.g., available under the brand names Serpasil, Mecamylamine, Hexemethonium), and the like);

blood vessel dilators (e.g., hydralazine hydrocholoride (e.g., available under the brand name Apresoline), minoxidil (e.g., e.g., available under the brand name Loniten), and the like);

central agonists (e.g., alpha methyldopa (e.g., available under the brand name Aldomet), clonidine hydrochloride (e.g., available under the brand name Catapres), guanabenz acetate (e.g., available under the brand name Wytensin), guanfacine hydrochloride (e.g., available under the brand name Tenex), and the like;

combined alpha and beta-blockers (e.g., carvedilol (e.g., available under the brand name Coreg), labetolol hydrochloride (e.g., available under the brand names Normodyne, Trandate), and the like);

alpha blockers (e.g., doxazosin mesylate (e.g., available under the brand name Cardura), prazosin hydrochloride (e.g., available under the brand name Minipress), terazosin hydrochloride (e.g., available under the brand name Hytrin), and the like);

combination diuretics (e.g., amiloride hydrochloride+hydrochlorothiazide (e.g., available under the brand name Moduretic), spironolactone+hydrochlorothiazide (e.g., Aldactazide), triamterene+hydrochlorothiazide (e.g., available under the brand names Dyazide, Maxzide) and the like);

adiponectin;

phenserine;

phosphodiesterase 4 inhibitor;

valproate;

dehydroepiandrostonedione;

potassium sparing diuretics (e.g., amiloride hydrochloride (e.g., available under the brand name Midamar), spironolactone (e.g., available under the brand name Aldactone), triamterene (e.g., available under the brand name Dyrenium), and the like); nitrates (e.g., L-arginine, (e.g., available under the brand names Nitroglycerin Deponit, Minitran, Nitropar, Nitrocine, Nitro-Derm, Nitro Disc, Nitro-Dur, Nitrogard, Nitroglycerin, Nitroglycerin T/R, Nitro-Time, Nitrol Ointment, Nitrolingual Spray, Nitrong, Nitro-Bid, Nitropress, Nitroprex, Nitro S.A., Nitrospan, Nitrostat, Nitro-Trans System, Nitro-Transdermal, Nitro-Time, Transderm-Nitro, Tridil. Pentaerythritol Tetranitrate Peritrate, Peritrate S.A. Erythrityl Tetranitrate Cardilate Isosorbide Dinitrate/Phenobarbital Isordil w/PB Isosorbide Mononitrate lmdur, ISMO, Isosorbide Mononitrate, Monoket Isosorbide Nitrate Dilatrate-SR, Iso-bid, Isordil, Isordil Tembids, Isordil Dinitrate, Isordil Dinitrate LA, Sorbitrate, Sorbitrate SA), and the like);

cyclic nucleotide monophosphodiesterase ("PDE") inhibitors (e.g., vardenafil (e.g., available under the brand name Levitra), sildenafil (e.g., available under the brand name Viagra) tadalafil (e.g., available under the brand name Cialis) and the like);

alcohols;

vasopressin inhibitors (e.g., atosiban (Tractocile), AVP V1a (OPC-21268, SR49059 (Relcovaptan)), V2 (OPC-31260, OPC-41061 (Tolvaptan), VPA-985 (Lixivaptan), SR121463, VP-343, FR-161282) and mixed V1a/V2 (YM-087 (Conivaptan), JTV-605, CL-385004) receptor antagonists, and the like);

oxytocin inhibitors (e.g., terbutaline, ritodrine, and the like);

glucagons like peptide 1;

relaxin hormone;

renin inhibitors (e.g., Aliskiren, and the like);

estrogen and estrogen analogues (e.g., estradiols, and the like) and metabolites;

progesterone inhibitors;

testosterone inhibitors;

gonadotropin-releasing hormone analogues (GnRH-As);

gonadotropin-releasing hormone inhibitors (e.g., Leuprolide Acetate, and the like);

vesicular monoamine transport (VMAT) inhibitors (e.g., tetrabenazine, and the like);

dipeptidyl peptidase (DP) IV inhibitors (DP4 inhibitors) (e.g., LAF237, P93/01, P32/98, valine pyrrolidide, and the like);

melatonin; and the like;

Anti-coagulants (e.g., erythropoietin (EPOGEN), filgrastim (G-CSF, NEUPOGEN), oprelevekin (Neumega), ximelagatran (EXANTA); hirulog (BIVALIR1DIN); abciximab (REOPRO); dipridamole (AGGRENOX); anagrlide (AGRILYN); clopiogrel (PLAVIX); dipridamole (PERSANTINE); eptifabatide (INTEGRILIN); ticlopidine (TICLID); tirofibam (AGGRASTAT); ardeparin (NORMIFLO); dalteparin (FRAGMIN); dnaparoid (ORGARIN); enoxaparin (LOVENOX); lepiudin (REFLUDAN); heparin; warfarin; alteplase (ACTIVASE), t-PA); reteplase (RETEVASE); streptokinase; urokinase; aminocaproic acid (AMICAR); cilostazol (PLETAL); pentoxifylline (TRENTAL); and the like).

As noted above, one or more of the above-described a pharmacological agents may be employed in the practice of the subject methods, e.g., to treat a subject for hypoxia and/or hypercapnia and/or acidosis and/or hypercarbia and/or a condition that causes hypoxia and/or hypercapnia and/or acidosis and/or a condition that results from any of the hypoxia and/or hypercapnia and/or acidosis and/or hypercarbia and/or condition that has caused such, and may be of particular use in modulating at least a portion of a subject's autonomic nervous system to increase the parasympathetic activity/sympathetic activity ratio. However, other pharmacological agents may be employed in the practice of the subject methods to treat a subject for one or more of the above described conditions. For example, one or more of the following pharmacological agents may be employed in the practice of the subject methods, where one or more of the following pharmacological agents may be of particular use in modulating at least a portion of a subject's autonomic nervous system to increase the sympathetic activity/parasympathetic activity ratio, e.g., to treat a subject for sleep apnea. Representative pharmacological agents (and analogs and salts thereof) that may be employed in the practice of the subject methods (e.g., to modulating at least a portion of a subject's autonomic nervous system to increase the parasympathetic activity/sympathetic activity ratio) include, but are not limited to, one of more of the following:

beta agonists, e.g., dobutamine, metaproterenol, terbutaline, ritodrine, albuterol;

alpha agonists, e.g., selective alpha 1-adrenergic blocking agents such as phenylephrine, metaraminol, methoxamine; prednisone and steroids, (e.g., available under the brand names CORATN, DELTASONE, LIQUID PRED, MEDICORTEN, ORASONE, PANASOL-S, PREDNICEN-M, PREDNISONE INTENSOL);

indirect agents that include norepinephrine, e.g., ephedrine, ampthetamines, phenylpropanolamines, cyclopentamines, tuaminoheptanes, naphazolines, tetrahydrozolines;

epinephrine;
norepinephrine;
acetylcholine;
sodium;
calcium;
angiotensin I;
angiotensin II;
angiotensin converting enzyme I ("ACE I");
angiotensin converting enzyme II ("ACE II");
aldosterone;
potassium channel blockers and magnesium channel blockers, e.g., valproate (sodium valproate, valproic acid), lithium;
cocaine;
amphetamines;
ephedrine;
terbutaline;
dopamine;
dobutamine;
antidiuretic hormone ("ADH") (also known as vasopressin);
oxytocin (including PITOCINE);
THC cannabinoids;
prednisone and steroids; and
progesterone, and combinations thereof.

Embodiments may include administering an effective amount of a first pharmacological agent and an effective amount of at least a second, different pharmacological agent, e.g., concurrently administered, where the two may differ in one or more of a variety of aspects, e.g., dosage, type, route of administration, etc. For example, embodiments may include administering a first type of pharmacological agent and at least one other type of pharmacological agent to provide an enhanced therapeutic effect. By "enhanced therapeutic effect" is meant that at least the initial relief of the particular condition being treated by the first pharmacological agent employed occurs more quickly with a combination of the first pharmacological agent and at least one other different pharmacological agent, as compared to the same doses of each component given alone, or that doses of one or all component(s) are below what would otherwise be a minimum effective dose (a "sub-MED").

Accordingly, embodiments of the subject invention includes treating a subject for a condition by modulating at least a portion of the subject's autonomic nervous system by administering a first pharmacological agent together with at least one other, different pharmacological agent. Such a protocol may be employed, e.g., in the treatment of sleep apnea. The pharmacological agents may be concomitantly administered as described above, i.e., they may be given in close enough temporal proximity to allow their individual therapeutic effects to overlap. For example, embodiments of the subject invention may include the co-timely administration of a first pharmacological agent and at least a second, different pharmacological agent. By "co-timely" with respect to drug administration is meant administration of a second pharmacological agent for the treatment of a condition while a first pharmacological agent is still present in a subject's system at an effective amount. It is to be understood that in some instances this will require sequential administration. Alternatively, multiple routes of administration may be employed, e.g., intravenous or subcutaneous injection of a first pharmacological agent may be combined with oral administration of a second, different pharmacological agent.

Embodiments also include pharmaceutical compositions in unit dosage forms that are useful in treating a subject for a condition by modulating at least a portion of a subject's autonomic nervous system and which contain a first pharmacological agent and at least a second, different type of pharmacological agent. In other words, a single drug administration entity or unit dosage form may include two or more pharmacological agents. For example, a single tablet, capsule, dragee, trocheem suppository, syringe, transdermal patch, and the like, combining two or more pharmacological agents would be a unit dosage form. The therapeutic agents present in a unit dosage form may be present in amounts such that, upon administration of one or more unit doses of the composition, a subject may experience a longer lasting efficacy than with the administration of either agent alone. Such compositions may be included as part of a therapeutic package in which one or more unit doses are placed in a finished pharmaceutical container. Labeling may be included to provide directions for using the composition in the treatment of a condition such as sleep apnea or other condition by modulating at least a portion of a subject's autonomic nervous system. The actual amounts of each agent in such compositions will vary according to the specific compositions being utilized, the particular compositions formulated, the mode of application, the particular route of administration, and the like. Dosages for a given subject can be determined using conventional considerations, e.g., by customary comparison of the differential activities of the subject compositions and of a known agent, or by means of an appropriate, conventional pharmacological protocol. A person of ordinary skill in the art will be able without undue experimentation, having regard to that skill and this disclosure, to determine an effective amount of a particular pharmacological agent for practice of this invention. For example, embodiments may include dosages conventionally administered for the particular pharmacological agents employed, where such dosages are known in the art.

Accordingly, in practicing embodiments of the subject methods, an effective amount of a pharmacological agent (or a plurality of different pharmacological agents) may be administered to a subject to treat a condition affecting the subject such as sleep apnea. As noted above, the particular dosage, mode of administration, treatment times, etc., will vary according to a variety of factors, but will generally fall within the ranges conventionally administered for the particular pharmacological agent employed. As noted above, the dose of pharmacological agent will be different for different subject, condition(s) treated, etc. The descriptions herein of exemplary embodiments describe average doses and may vary. Such descriptions are for exemplary purposes only and are in no way intended to limit the scope of the invention. For example, the number of capsules or tablets, teaspoonfuls of solution, and the like, administered depends at least in part on the strength of the particular pharmacological agent administered. Furthermore, the number of doses administered each day, the time allowed between doses, and the length of time a subject takes the medicine, etc., depend on the condition being treated, i.e., the condition for which a subject is taking the pharmacological agent. Exemplary treatment protocols are now provided.

Beta-Blocker

As noted above, embodiments may include administering an effective amount of a beta-blocker to treat a condition, e.g., hypoxia, hypercarbia, hypercarbia, acidosis, a condition resulting from such, a condition having a manifestation of such (e.g., sleep apnea), etc.). Such embodiments may include administering adult oral dosage forms (capsules and tablets) of acebutolol ranging from about 200 milligrams (mgs.) to about 1200 mgs., e.g., from about 200 mgs. to about 800 mgs. Such oral dosages may be administered as a single dose one time a day, two times a day, or divided into two daily doses for an adult, etc.

Embodiments may include administering atenolol to treat a condition, e.g., hypoxia, hypercarbia, hypercapnia, acidosis, a condition resulting from such, a condition having a manifestation of such (e.g., sleep apnea), etc.). Such embodiments may include administering adult oral dosage forms (e.g., tablets) of atenolol (e.g., available under the brand name TENORMIN) that range from about 25 mgs. to about 100 mgs. once a day. For example, administration may include about 50 mgs. once a day, or about 100 mgs. of atenolol once a day, or about 50 mgs. atenolol two times a day, e.g., for about six to about nine days. Embodiments that include administering atenolol in adult injection dosage forms may include about 5 mgs. given over 5 minutes, repeated ten minutes later. Atenolol may also be administered intravenously in certain embodiments.

Embodiments may include administering adult oral dosage forms (e.g., tablets) of betaxolol to treat a condition, e.g., hypoxia, hypercarbia, hypercapnia, acidosis, a condition resulting from such, a condition having a manifestation of such (e.g., sleep apnea), etc.). Such embodiments may include administering about 10 mgs. of betaxolol as an adult dosage form once a day.

Embodiments may include administering adult oral dosage forms (e.g., tablets) of bisoprolol (e.g., available under the brand name ZEBETA) to treat a condition, e.g., hypoxia, hypercarbia, hypercapnia, acidosis, a condition resulting from such, a condition having a manifestation of such (e.g., sleep apnea), etc.). Such embodiments may include administering about 5 mgs. to about 10 mgs. of bisoprolol as an adult oral dosage forms (e.g., tablets) once a day.

Embodiments may include administering adult oral dosage forms (e.g., tablets) of carteolol to treat a condition, e.g., hypoxia, hypercarbia, hypercapnia, acidosis, a condition resulting from such, a condition having a manifestation of such (e.g., sleep apnea), etc.). Adult oral dosage forms (e.g., tablets) of carteolol may include about 0.5 mgs. to about 10 mgs. administered once a day.

Embodiments may include administering esmolol to treat a condition, e.g., hypoxia, hypercarbia, acidosis, hypercapnia, a condition resulting from such, a condition having a manifestation of such (e.g., sleep apnea), etc.), via IV. esmolol may be administered via iv as follows: loading dose of about 20-30 mg ivp over 1 minute using a 10 mg/ml 10 ml vial and maintenance dose of about 2 To 12 mg/min as titrated to patient response and maintenance infisions may be increased by about 2 to 3 mg/min at 10 minute intervals until the desired response is achieved.

Embodiments may include administering adult oral dosage forms (e.g., tablets) of labetalol to treat a condition, e.g., hypoxia, hypercarbia, hypercapnia, acidosis, a condition resulting from such, a condition having a manifestation of such (e.g., sleep apnea), etc.). Adult oral dosage forms (e.g., tablets) of labetalol may include about 100 mgs. to about 400 mgs. two times a day. Adult injection dosage forms may include about 20 mgs., e.g., injected slowly over about two minutes with additional injections of about 40 mgs. and about 80 mgs. given about every ten minutes if needed, up to a total of about 300 mgs., instead as an infusion at a rate of about 2 mgs. per minute to a total dose of about 50 mgs. to about 300 mgs.

Embodiments may include administering adult oral dosage forms (e.g., tablets) of metaprolol to treat a condition, e.g., hypoxia, hypercarbia, acidosis, hypercapnia, a condition resulting from such, a condition having a manifestation of such (e.g., sleep apnea), etc.). Adult oral dosage forms (e.g., tablets) of metoprolol may include about 100 mgs. to 450 mgs. a day, taken as a single dose or in divided doses. For example, embodiments may include administering about 50 mgs. about every six hours for about 24 hours or more and then about 100 mgs. two times a day for about 1 to about 3 months or more, e.g., from about 1 to about 3 years or more. Embodiments may include administering long-acting adult oral dosage forms (extended-release tablets) that may include up to about 400 mgs. once a day. Adult injection dosage forms may include about 5 mgs. every two minutes for about three doses.

Embodiments may include administering adult oral dosage forms (e.g., tablets) of nadolol (e.g., available under the brand name CORGARD) to treat a condition, e.g., hypoxia, hypercarbia, acidosis, hypercapnia, a condition resulting from such, a condition having a manifestation of such (e.g., sleep apnea), etc.). Embodiments ay include administering adult oral dosage forms (e.g., tablets) of nadolol that may include about 40 mgs. to about 320 mgs. once a day.

Embodiments may include administering adult oral dosage forms (e.g., tablets) of oxprenolol to treat a condition, e.g., hypoxia, hypercarbia, acidosis, hypercapnia, a condition resulting from such, a condition having a manifestation of such (e.g., sleep apnea), etc.). Embodiments may include administering adult oral dosage forms (e.g., tablets) of oxprenolol (short-acting) that may include about 20 mgs. three times a day. Embodiments may include administering adult long-acting oral dosage forms (extended-release tablets) that may include about 120 mgs. to about 320 mgs. once a day.

Embodiments may include administering adult oral dosage forms (e.g., tablets) of pentbutolol to treat a condition, e.g., hypoxia, hypercarbia, acidosis, hypercapnia, a condition resulting from such, a condition having a manifestation of such (e.g., sleep apnea), etc.). Embodiments may include administering adult oral dosage forms (e.g., tablets) of penbutolol that may include about 20 mgs. once a day.

Embodiments may include administering adult oral dosage forms (e.g., tablets) of pindolol to treat a condition, e.g., hypoxia, hypercarbia, acidosis, hypercapnia, a condition resulting from such, a condition having a manifestation of such (e.g., sleep apnea), etc.). Embodiments may include administering adult oral dosage forms (e.g., tablets) of pindolol that may include about 5 mgs. two times a day—up to about 60 mgs. a day.

Embodiments may include administering adult oral dosage forms (e.g., tablets) of propranolol to treat a condition, e.g., hypoxia, hypercarbia, acidosis, hypercapnia, a condition resulting from such, a condition having a manifestation of such (e.g., sleep apnea), etc. Embodiments may include administering adult oral dosage forms (e.g., tablets) of propranolol that may include, for regular (short-acting) oral dosage forms (tablets and oral solution), about 80 mgs. to about 320 mgs. a day taken in two, three, or four divided doses up to about 640 mgs./day in certain embodiments.

Embodiments may also include about 10 mgs. to about 40 mgs. three or four times a day for an adult and about 500 micrograms (0.5 mgs.) to about 4 mgs. per kilogram of body weight a day taken in divided doses for children. Embodiments may include administering long-acting adult oral dosage forms (extended-release capsules) that may include about 80 mgs. to about 320 mgs. once a day up to about 640 mgs. once a day. Embodiments may include administering adult injection dosage forms that range from about 1 mg. to about 3 mgs. given at a rate not greater than about 1 mg per minute. The dose may be repeated after about two minutes and again after about four hours if needed. Children may be administered about 10 mgs. to about 100 micrograms (0.01 to 0.1 mg) per kilogram of body weight given intravenously about every six to eight hours.

Embodiments may include administering adult oral dosage forms (e.g., tablets) of sotalol to treat a condition, e.g., hypoxia, hypercarbia, acidosis, hypercapnia, a condition resulting from such, a condition having a manifestation of such (e.g., sleep apnea), etc. Embodiments may include administering adult oral dosage forms (e.g., tablets) of sotalol that may include about 80 mgs. two times a day up to about 320 mgs. per day taken in two or three divided doses.

Embodiments may include administering adult oral dosage forms (e.g., tablets) of timolol (e.g., available under the brand name BLOCADREN) to treat a condition, e.g., hypoxia, hypercarbia, acidosis, hypercapnia, a condition resulting from such, a condition having a manifestation of such (e.g., sleep apnea), etc. Embodiments may include administering adult oral dosage forms (e.g., tablets) of timolol that may include about 10 mgs. two times a day up to about 60 mgs. per day taken as a single dose or in divided doses. For example, up to 30 mgs. once a day or in divided doses.

Aldosterone Antagonists

Embodiments may include administering an aldosterone antagonist to treat a condition, e.g., hypoxia, hypercarbia, acidosis, hypercapnia, a condition resulting from such, a condition having a manifestation of such (e.g., sleep apnea), etc., in accordance with the subject invention. For example, embodiments may include administering adult oral dosage forms (e.g., tablets) of spironolactone that may range from about 50 mgs. to about 400 mgs. daily. Embodiments may include administering adult oral dosage forms (e.g., tablets) of eplerenone that may range from about 50 mgs. to about 100 mgs. daily.

Angiotensin II Receptor Blockades

Embodiments may include administering an angiotensin II receptor blockade to treat a condition, e.g., hypoxia, hypercarbia, acidosis, hypercapnia, a condition resulting from such, a condition having a manifestation of such (e.g., sleep apnea), etc., in accordance with the subject invention. Such embodiments may include administering an adult oral dosage form of candesartan (e.g., ATACAND) to a subject to treat a condition. Exemplary treatment protocols may include administering about 2 mgs. to about 32 mgs. of candesarten daily (i.e., for a 24 hour interval), e.g., about 16 mgs. daily. Embodiments may include administering adult oral dosage forms of irbersarten (e.g., AVAPRO) to a subject to treat a condition. Exemplary treatment protocols may include administering about 75 mgs. to about 100 mgs. or more, e.g., up to about 300 mgs., of irbersarten daily. Embodiments may include administering adult oral dosage forms of losartan (e.g., COZAAR) to a subject to treat a condition. Exemplary treatment protocols may include administering about 25 mgs. to about 50 mgs. or more, e.g., 100 milligrams, of losarten orally once daily or twice daily. Embodiments may include administering adult oral dosage forms of telmisartin (e.g., MICARDIS) to a subject to treat a condition. Exemplary treatment protocols may include administering about 20 mgs. to about 80 mgs. of telmisartin daily. Embodiments may include administering adult oral dosage forms of valsartan (e.g., DIOVAN) to a subject to treat a condition. Exemplary treatment protocols may include administering about 20 mgs. to about 80 mgs. of valsarten once daily. Embodiments may include administering adult oral dosage forms of eprosarten (e.g., TEVETAN) to a subject to treat a condition. Exemplary treatment protocols may include administering about 400 mgs. to about 800 mgs. of eprosarten once daily or twice daily.

Angiotensin Converting Enzyme Inhibitors (ACE Inhibitors)

Embodiments may include administering an ACE inhibitor to a subject to treat a condition, e.g., hypoxia, hypercarbia, acidosis, hypercapnia, a condition resulting from such, a condition having a manifestation of such (e.g., sleep apnea), etc., in accordance with the subject invention. Such may include administering adult oral dosage forms of captropil (e.g., CAPOTEN) to a subject to treat a condition. Exemplary treatment protocols may include administering about 12.5 mgs. to about 50 mgs. of captropil over about 8 to about 12 hours. Embodiments may include administering adult oral dosage forms of enalapril (e.g., VASOTEC) to a subject to treat a condition. Exemplary treatment protocols may include administering about 5 mgs. to about 20 mgs. of enalapril once daily. Embodiments may include administering adult oral dosage forms of fosinopril (e.g., MONOPRIL) to a subject to treat a condition. Exemplary treatment protocols may include administering about 10 mgs. to about 80 mgs., e.g., about 20 mgs. to about 40 mgs., of fosinopril daily. Embodiments may include administering adult oral dosage forms of lisinopril (e.g., PRINIVIL) to a subject to treat a condition. Exemplary treatment protocols may include administering about 10 mgs. to about 80 mgs., e.g., about 20 mgs. to about 40 mgs., of lisinopril daily. Embodiments may include administering adult oral dosage forms of moexipril (e.g., UNIVASC) to a subject to treat a condition. Exemplary treatment protocols may include administering about 3.75 mgs. to about 15 mgs., e.g., 7.5 mgs. of moexipril daily. Embodiments may include administering adult oral dosage forms of quinaapril (e.g., ACCUPRIL) to a subject to treat a condition. Exemplary treatment protocols may include administering about 10 mgs. to about 80 mgs, e.g., about 20 mgs., of quinapril once daily. Embodiments may include administering adult oral dosage forms of ramipril (e.g., ALTACE) to a subject to treat a condition. Exemplary treatment protocols may include administering about 2.5 mgs. to about 20 mgs. of ramipril daily. Embodiments may include administering adult oral dosage forms of trandolapril (e.g., MAVIK) to a subject to treat a condition. Exemplary treatment protocols may include administering about 1 mg. to about 4 mgs., e.g., about 2 mgs., of trandolapril daily.

Statins

Embodiments may include administering adult oral dosage forms (e.g., tablets) of a statin to treat a condition, e.g., hypoxia, hypercarbia, acidosis, hypercapnia, a condition resulting from such, a condition having a manifestation of such (e.g., sleep apnea), etc., in accordance with the subject invention. For example, embodiments may include administering adult oral dosage forms (e.g., tablets) of atorvastatin (e.g., available under the brand name Lipitor) that may range from about 0.5 mgs. to about 80 mgs. daily. Embodiments may include administering adult oral dosage forms (e.g., tablets) of cerivastatin (e.g., available under the brand name Baycol) that may range from about 0.2 mgs. to about 0.3 mgs. daily. Embodiments may include administering adult oral dosage forms (e.g., tablets) of fluvastatin (e.g., available under the brand name lescoL) that may range from about 20 mgs. to about 80 mgs. daily. Embodiments may include administering adult oral dosage forms (e.g., tablets) of lovastatin (e.g., available under the brand name Mevacor) that may range from about 10 mgs. to about 80 mgs. daily. Embodiments may include administering-adult oral dosage forms (e.g., tablets) of prevastatin (e.g., available under the brand name Pravachol) that may range from about 10 mgs. to about 40 mgs. daily. Embodiments may include administering adult oral dosage forms (e.g., tablets) of simvastatin (e.g., available under the brand name Zocor) that may range from about 5 mgs. to about 40 mgs. daily.

Triglycerides Lowering Drugs

Embodiments may include administering adult oral dosage forms (e.g., tablets) of a triglycerides lowering drug to treat a condition, e.g., hypoxia, hypercarbia, acidosis, hypercapnia, a condition resulting from such, a condition having a manifestation of such (e.g., sleep apnea), etc., in accordance with the subject invention. For example, embodiments may include administering adult oral dosage forms (e.g., tablets) of fenofibrate (e.g., available under the brand name TRICOR) that may range from about 65 mgs. to about 200 mgs. daily. Embodiments may include administering adult oral dosage forms (e.g., tablets) of genfibrozil (e.g., available under the brand name LOPID) that may range from about 1200 mgs. total given as about 600 mgs. two times per day (e.g., every 12 hours).

Niacin

Embodiments may include administering niacin to treat a condition, e.g., hypoxia, hypercarbia, acidosis, hypercapnia, a condition resulting from such, a condition having a manifestation of such (e.g., sleep apnea), etc., in accordance with the subject invention. For example, dosing may include administering by mouth about 2 mgs. to about 6 mgs. total, e.g., as given as about 1 mg. to about 2 mgs. twice per day or three times per day.

Diabetes Agents

Embodiments may include administering a diabetes drug to treat a condition, e.g., hypoxia, hypercarbia, acidosis, hypercapnia, a condition resulting from such, a condition having a manifestation of such (e.g., sleep apnea), etc., in accordance with the subject invention. For example, embodiments may include administering adult oral dosage forms (e.g., tablets) of acarbose (e.g., available under the brand name PRECOSE) that may range from about 25 mgs. to about 300 mgs. for an eight hour interval. Embodiments may include administering adult oral dosage forms (e.g., tablets) of glimepiride(e.g., available under the brand name AMARYL) that may range from about 1 mg. to about 2 mgs. daily. Embodiments may include administering adult oral dosage forms (e.g., tablets) of glyburide (e.g., available under the brand names MICRONASE, DIABETA) that may range from about 1.5 mgs. to about 5 mgs. daily. Embodiments may include administering adult oral dosage forms (e.g., tablets) of metformin (e.g., available under the brand name GLUCOPHASGE) that may range from about 500 mgs. to about 850 mgs. for an 8 to 24 hour interval. Embodiments may include administering adult oral dosage forms (e.g., tablets) of miglitol (e.g., available under the brand name GLYCET) that may range from about 25 mgs. to about 100 mgs. for an 8 hour interval. Embodiments may include administering adult oral dosage forms (e.g., tablets) of pioglitazone (e.g., available under the brand name ACTOS) that may range from about 15 mgs. to about 40 mgs. daily. Embodiments may include administering adult oral dosage forms (e.g., tablets) of repaglinide (e.g., available under the brand name PRANDIN) that may range from about 0.5 mgs. to about 4.0 mgs. 3 times per day. Embodiments may include administering adult oral dosage forms (e.g., tablets) of rosiglitazone (e.g., available under the brand name AVANDIA) that may range from about 4 mgs. to about 8 mgs. daily.

Immunomodulators

Embodiments may include administering an immunomodulator to treat a condition, e.g., hypoxia, hypercarbia, acidosis, hypercapnia, a condition resulting from such, a condition having a manifestation of such (e.g., sleep apnea), etc., in accordance with the subject invention. For example, embodiments may include administering interferon beta-1B (e.g., available under the brand name BETASERON), where dosing may include administering about 0.25 mg. subcutaneously every other day. Embodiments may also include administering interferon alfa-2A (e.g., available under the brand name ROFERON-A), where dosing may include administering about 3 million units to about 36 million units per day IM/SC to about 3 million units to about 36 million units 3 times per week (3 million units (1 ml); 6 million units/ml (3 ml); 0 million units/ml (0.9 ml), 3 ml); 36 million units/ml (1 ml)). Embodiments may also include administering interferon alfa-2B (e.g., available under the brand name INTRON-A), where dosing may include administering about 1 to about 30 million units/M2 IM/SC three times per week (3 million units (0.5 ml); 5 million units (0.5 ml); 10 million units (1 ml); 25 million units powder for injection: 18 million units and 50 million units). Embodiments may also include administering interferon alfa-2B and ribavirin combination pack (e.g., available under the brand name REBETRON), where dosing may include administering INTRON A at about 3 million units subcutaneously three times per week and about 500 mgs. to about 600 mgs. of ribavirin twice daily. Embodiments may also include administering interferon alfa-N3 (e.g., available under the brand name ALFERON N), where dosing may include administering about 250,000 units (0.05 ml) twice weekly (5 million units (1 ml)). Embodiments may also include administering interferon beta-1A (e.g., available under the brand name AVONEX), where dosing may include administering about 30 micrograms IM once weekly (reconstitute with 1.1 ml of diluent).

Nicotine

Embodiments may include administering nicotine to treat a condition, e.g., hypoxia, hypercarbia, acidosis, hypercapnia, a condition resulting from such, a condition having a manifestation of such (e.g., sleep apnea), etc., in accordance with the subject invention. For example, embodiments may include administering nicotine in the form of chewing gum, e.g., from about 2 mgs. to about 4 mgs. dosage strength). Embodiments may include administering nicotine as an inhalant (e.g., about 4 mgs. per cartridge), nasal spray (e.g., each actuation of nicotine nasal spray may deliver about 0.5 mgs. nicotine), or as a transdermal system. For example, dosing schedules (mg/day) of nicotine transdermal systems may include a patch duration of about 24 hours and dosing schedule of about 7 mgs. to about 22 mgs. for about 2 to about 6 weeks; a patch duration of about 16 hours and a dosing schedule of about 15 mgs. for about 4 to about 12 weeks. Each dosing schedule may be followed by a reduced dosing schedule.

Sympathomimetics

Embodiments may include administering a sympathomimetic to treat a condition, e.g., hypoxia, hypercarbia, acidosis, hypercapnia, a condition resulting from such, a condition having a manifestation of such (e.g., sleep apnea), etc., in accordance with the subject invention. For example, embodiments may include administering trimethaphan via an I.V., e.g., about 0.1 mgs. to about 1.0 mgs./minute, up to about 15 mgs. per minute. Embodiments may include administering by mouth clondine at about 0.1 mgs. to about 2.4 mgs. daily. Embodiments may include administering by mouth reserpine at about 10 mgs. to about 20 mgs. daily. Embodiments may include administering by mouth guanethidine at about 10 mgs. to about 50 mgs. daily.

Antihistamines

Embodiments may include administering adult oral dosage forms of an antihistamine to treat a condition, e.g., hypoxia, hypercarbia, acidosis, hypercapnia, a condition resulting from such, a: condition having a manifestation of such (e.g., sleep apnea), etc., in accordance with the subject invention. For example, embodiments may include administering adult oral dosage forms (e.g., tablets) of BENADRYL at about 25 mgs. to about 50 mgs. three to four times daily. Nighttime dosage may include about 50 mgs. at bedtime.

Cholinergics

Embodiments may include administering a cholinergic to treat a condition, e.g., hypoxia, hypercarbia, acidosis, hypercapnia, a condition resulting from such, a condition having a manifestation of such (e.g., sleep apnea), etc., in accordance with the subject invention. For example, embodiments may include administering bethanechol by mouth at about 10 mgs. to about 50 mgs. four times per day or three times per day. Embodiments may include administering methacoline as an inhaled aerosol at about 0.02 to about 25.0 mg/mL. Embodiments may include orally administering about 30 mgs. cevimeline three times per day.

Acetylcholinesterase Inhibitors

Embodiments may include administering an acetylcholinesterase inhibitor to treat a condition, e.g., hypoxia, hypercarbia, acidosis, hypercapnia, a condition resulting from such, a condition having a manifestation of such (e.g., sleep apnea), etc., in accordance with the subject invention. For example, embodiments may include administering about 0.1 ml. to about 0.8 ml via an I.V. edrophonium or about 1 ml. of a 1:20000 solution (0.5 mg.) of neostigmine intramuscularly (IM) or subcutaneously (SC). Embodiments may also include orally administering about 5 mg of donepezil to about 10 mgs./day. Embodiments may also include administering about 1 to about 2 g of pralidoxime, e.g., as an infusion in 100 mL of saline, over about a 15 to 30 minute period, via I.V. About 16 mgs to about 32 mgs. of galanthamine may be administered orally twice per day. Physostigmine may be administered intravenously or intramuscularly e.g., about 0.5 mgs. to about 2 mgs. Rivastigmine may be orally administered, e.g., about 3 mgs. to about 6 mgs. two times per day.

Magnesium and Magnesium Sulfates

Embodiments may include administering magnesium to treat a condition, e.g., hypoxia, hypercarbia, acidosis, hypercapnia, a condition resulting from such, a condition having a manifestation of such (e.g., sleep apnea), etc., in accordance with the subject invention. For example, a dose may include administering about 0.3 mEq/kg to about 1.0 meq mg/kg daily via an I.V.

Calcium Channel Blockers:

Embodiments may include administering a calcium channel blocker to treat a condition, e.g., hypoxia, hypercarbia, acidosis, hypercapnia, a condition resulting from such, a condition having a manifestation of such (e.g., sleep apnea), etc., in accordance with the subject invention. Embodiments may include orally administering amlodipine besylate (e.g., available under the brand name NORVASC), e.g., about 5 mgs. to about 20 mgs. daily; diltiazem hydrochloride (e.g., available under the brand names CARDIZEM CD, CARDIZEM SR, DILACOR XR, TIAZAC) at about 30 mgs. to about 360 mgs. four times per day (for example 180 mgs. to about 360 mgs. divided into four times per day); felodipine plendil at about 2.5 mgs. to about 10 mgs. daily; isradipine (e.g., available under the brand names DYNACIRC, DYNACIRC CR) at about 2.5 mgs. daily; nicardipine (e.g., available under the brand name CARDENE SR) at about 20 mgs. to about 40 mgs. three times per day; nifedipine (e.g., available under the brand names ADALAT CC, PROCARDIA XL) at about 10 mgs. three times per day; nisoldipine (e.g., available under the brand name SULAR) at about 10 mgs. to about 20 mgs. daily; and verapamil hydrochloride (e.g., available under the brand names CALAN SR, COVERA HS, ISOPTIN SR, VERELAN) at about 40 mgs. three times per day.

Muscarinics

Embodiments may include administering a muscarinic to treat a condition, e.g., hypoxia, hypercarbia, acidosis, hypercapnia, a condition resulting from such, a condition having a manifestation of such (e.g., sleep apnea), etc., in accordance with the subject invention. For example, embodiments may include administering about 5 mgs. of pilocarpine by mouth to a subject four times per day, up to about 30 mgs./day.

Sodium Channel Blockers

Embodiments may include administering a sodium channel blocker to treat a condition, e.g., hypoxia, hypercarbia, acidosis, hypercapnia, a condition resulting from such, a condition having a manifestation of such (e.g., sleep apnea), etc., in accordance with the subject invention. For example, embodiments may include administering about 150 mgs. of propafenone by mouth every 8 hours (450 mgs./day) up to about 300 mgs. every 8 hours (90 mgs./day). Embodiments may also include administering about 50 mgs. to about 100 mgs. of flecainide by mouth about every 12 hours up to about 400 mgs./day. Embodiments may also include administering about 400 mgs. to about 2400 mgs. of tocainide by mouth about every 8 hours. Embodiments may also include administering about 100 mgs. to about 200 mgs. of phenytoin by mouth three times per day. Embodiments may also include administering about 10-30 mgs of about 1% to about 2% lidocaine IM (the maximum individual dosage typically should not exceed about 4.5 mg/kg of body weight and generally the maximum total dose should not exceed about 300 mgs.). Embodiments may also include administering about 150 mgs. to about 300 mgs. of dispoyramide by mouth about every 6 hours to about every 12 hours, up to about 1600 mgs. per day. Embodiments may also include administering quinidine (e.g., available under the brand name QUINAGLUTE) at about two tablets (648 mgs.; 403 mgs. of quinidine base) of QUINAGLUTE by mouth about every 8 hours.

Glucocorticoid Receptor Blockers

Embodiments may include administering a glucocorticoid receptor blocker to treat a condition, e.g., hypoxia, hypercarbia, acidosis, hypercapnia, a condition resulting from such, a condition having a manifestation of such (e.g., sleep apnea), etc., in accordance with the subject invention. For example, embodiments may include administering mifepristone my mouth at about 400 micrograms to about 600 mgs.

Peripheral Andrenergic Inhibitors

Embodiments may include administering a peripheral andrenergic inhibitor to treat a condition, e.g., hypoxia, hypercarbia, acidosis, hypercapnia, a condition resulting from such, a condition having a manifestation of such (e.g., sleep apnea), etc., in accordance with the subject invention. For example, embodiments may include administering about 5 mgs. to about 75 mgs. of guanadrel (e.g., available under the brand name HYLOREL) by mouth e.g., about 5 mgs. two times per day, about 20 to about 75 mgs. per day in divided doses. Embodiments may also include administering about 10 mgs. to about 50 mgs. or more per day of guanethidine monosulfate (e.g., available under the brand name ISMELIN) by mouth. Embodiments may also include administering about 0.05 to about 1.5 mgs. once per day by mouth of reserpine (e.g., available under the brand names SERPASIL, MECAMYLAMINE, HEXEMETHONIUM). Embodiments may also include administering about 2.5 mgs. of mecamylamine two times per day by mouth.

Blood Vessel Dilators

Embodiments may include administering a blood vessel dilator to treat a condition, e.g., hypoxia, hypercarbia, acidosis, hypercapnia, a condition resulting from such, a condition having a manifestation of such (e.g., sleep apnea), etc., in accordance with the subject invention. For example, embodiments may include administering about 10 mgs. to about 50 mgs. of hydralazine hydrocholride (e.g., available under the brand name APRESOLINE) by mouth four times a day. Embodiments may also include administering about 5 mgs. to about 40 mgs. of minoxidil (e.g., e.g., available under the brand name LONITEN) by mouth once per day.

Central Agonists

Embodiments may include administering a central agonist to treat a condition, e.g., hypoxia, hypercarbia, acidosis, hypercapnia, a condition resulting from such, a condition having a manifestation of such (e.g., sleep apnea), etc., in accordance with the subject invention. For example, embodiments may include administering about 250 mgs. of alpha methyldopa (e.g., available under the brand name ALDOMET) by mouth three times per day or about 500 mgs. to about 2 grams per day divided into 2 to 4 doses. Embodiments may also include administering about 0.1 mgs. to about 0.6 mgs. of clonidine hydrochloride (e.g., available under the brand name CATAPRES) by mouth once per day. Embodiments may also include administering about 4 mgs. of guanabenz acetate (e.g., available under the brand name WYTENSIN) by mouth two times per day (up to about 32 mgs. per day). Embodiments may also include administering about 1 mg. to about 3 mgs. of guanfacine hydrochloride (e.g., available under the brand name TENEX) by mouth once per day.

Combined Alpha and Beta-blockers

Embodiments may include administering a combined alpha and beta-blocker to treat a condition, e.g., hypoxia, hypercarbia, acidosis, hypercapnia, a condition resulting from such, a condition having a manifestation of such (e.g., sleep apnea), etc., in accordance with the subject invention. For example, embodiments may include administering about 100 mgs. two times per day of labetolol hydrochloride (e.g., available under the brand names NORMODYNE, TRANDATE) by mouth up to about 400 mgs. per day. Embodiments may also include administering about 3.125 mgs. two times per day of carvedilol (e.g., available under the brand name COREG) by mouth up to about 50 mgs. per day.

Alpha Blockers

Embodiments may include administering an alpha and beta-blocker to treat a condition, e.g., hypoxia, hypercarbia, acidosis, hypercapnia, a condition resulting from such, a condition having a manifestation of such (e.g., sleep apnea), etc., in accordance with the subject invention. For example, embodiments may include administering about 1 mg once per day by mouth of doxazosin mesylate (e.g., available under the brand name CARDURA) up to about 16 mgs. per day. Embodiments may also include administering about 0.5 mgs. by mouth of prazosin hydrochloride (e.g., available under the brand name MINIPRESS) two or three times per day (and may include about 6 to about 15 mgs. per day divided into 2 or 3 doses. Embodiments may also include administering about 1 mg. of terazosin hydrochloride (e.g., available under the brand name HYTRIN) by mouth once per day, up to about 5 mgs. per day.

Combination Diuretics

Embodiments may include administering a combined diurentic to treat a condition, e.g., hypoxia, hypercarbia, acidosis, hypercapnia, a condition resulting from such, a condition having a manifestation of such (e.g., sleep apnea), etc., in accordance with the subject invention. For example, embodiments may include administering about 1-2 tablets of amiloride hydrochloride+hydrochlorothiazide (e.g., available under the brand name MODURETIC) once per day for tablets containing 5 mgs. of anhydrous amiloride HCI and 50 mgs. of hydrochlorothiazide). Embodiments may also include administering about 25 mgs. to about 50 mgs. once per day by mouth of spironolactone+hydrochlorothiazide (e.g., available under the brand name ALDACTAZIDE). Embodiments may also include administering about 1 to 2 tablets one per day of triamterene+hydrochlorothiazide (e.g., available under the brand names DYAZIDE, MAXZIDE) for tablets containing 25 mgs. hydrochlorothiazide and 37.5 mgs. triaterene.

Potassium Sparing Diuretics

Embodiments may include administering a potassium sparing diuretic to treat a condition, e.g., hypoxia, hypercarbia, acidosis, hypercapnia, a condition resulting from such, a condition having a manifestation of such (e.g., sleep apnea), etc., in accordance with the subject invention. For example, embodiments may include administering about 5 mgs. to about 20 mgs. by mouth once per day of amiloride hydrochloride (e.g., available under the brand name MIDAMAR). Embodiments may also include administering about 25 mgs. to about 200 mgs. once per day by mouth of spironolactone (e.g., available under the brand name ALDACTONE). Embodiments may also include administering about 1 to 2 tablets once per day of triamterene (e.g., available under the brand name DYRENIUM)) for tablets containing 25 mgs. hydrochlorothiazide and 37.5 mgs. triaterene.

Nitrates

Embodiments may include administering a nitrate to treat a condition, e.g., hypoxia, hypercarbia, acidosis, hypercapnia, a condition resulting from such, a condition having a manifestation of such (e.g., sleep apnea), etc., in accordance with the subject invention. For example, embodiments may include administering isosorbide dinitrate (e.g., available under the brand name ISODIL) at about 50 to about 40 mgs. orally four times per day or 40 mgs. sustained release orally every 8 to 12 hours. Embodiments may also include administering isosorbide mononitrate (e.g., available under the brand names ISMO, MONOKET) at about 20 mgs. orally two times per day and/or may include administering extended release initially about 30 mgs. to about 60 mgs.

orally once per day. Maximum of about 240 mgs./day. Embodiments may also include administering nitroglycerine ointment, e.g., about 0.5 inches q8h and/or about 0.5 to about 2 inches every 4 to 6 hours, maximum 4 inches every 4 to 6 hours (0.5 inches is about 7.5 mgs.). Embodiments may also include administering nitrobid, e.g., orally about 2.5 mgs. to about 9 mgs. 2 to 4 times per day. Embodiments may also include administering a nitroglycerin patch, e.g., one patch each day applied and removed at bedtime.

Cyclic Nucleotide Monophosphodiesterase ("PDE") Inhibitors

Embodiments may include administering a cyclic nucleotide monophodiesterase ("PDE") inhibitor to treat a condition, e.g., hypoxia, hypercarbia, acidosis, hypercapnia, a condition resulting from such, a condition having a manifestation of such (e.g., sleep apnea), etc., in accordance with the subject invention. For example, embodiments may include administering about 5 mgs. to about 20 mgs. once per day of vardenafil (e.g., available under the brand name LEVITRA) by mouth. Embodiments may also include administering about 10 mgs. to about 20 mgs. of tadalafil (e.g., available under the brand name CIALIS) orally once per day. Embodiments may also include administering about 25 mgs. to about 100 mgs. of sildenafil (e.g., available under the brand name VIAGRA) orally once per day.

Alcohols

Embodiments may include administering an alcohol to treat a condition, e.g., hypoxia, hypercarbia, acidosis, hypercapnia, a condition resulting from such, a condition having a manifestation of such (e.g., sleep apnea), etc., in accordance with the subject invention. For example, embodiments may include administering about 200 mgs. orally four times per day or 0.5 to about 1.0 ml per interspace for subarachnoid injections.

Vasopressin Inhibitors

Embodiments may include administering a vasopressin inhibitor to treat a condition, e.g., hypoxia, hypercarbia, acidosis, hypercapnia, a condition resulting from such, a condition having a manifestation of such (e.g., sleep apnea), etc., in accordance with the subject invention. For example, embodiments may include administering about up to about 6.75 mg administered via IV of atosiban, e.g., 300 micrograms/min to about 100 micrograms/min IV.

Oxytocin Inhibitors

Embodiments may include administering an oxytoxin inhibitor to treat a condition, e.g., hypoxia, hypercarbia, acidosis, hypercapnia, a condition resulting from such, a condition having a manifestation of such (e.g., sleep apnea), etc., in accordance with the subject invention. For example, embodiments may include administering about 0.25 to about IM of terbutaline, typically not more than about 0.5 mgs. within a four hour period. Embodiments may also include administering about 50 micrograms per minute IV of ritodrine, maximum dosage of about 300 micrograms per minute.

Glucagon Like Peptide 1

Embodiments may include administering glucagon like peptide 1 to treat a condition, e.g., hypoxia, hypercarbia, acidosis, hypercapnia, a condition resulting from such, a condition having a manifestation of such (e.g., sleep apnea), etc., in accordance with the subject invention. For example, embodiments may include administering by I.V. about 200 µg/kg two times per day. Embodiments may also include administering by SQ infusion about 1.25 to about 20 µg/kg.

Relaxin Hormone

Embodiments may include administering a relaxin hormone to treat a condition, e.g., hypoxia, hypercarbia, acidosis, hypercapnia, a condition resulting from such, a condition having a manifestation of such (e.g., sleep apnea), etc., in accordance with the subject invention. For example, embodiments may include administering 1 to 2 tablets of relaxin by mouth three times per day fro tablets pf valerian/ ayrvedic passion flower blend (550 mgs.)

Renin Inhibitors

Embodiments may include administering a rennin inhibitor to treat a condition, e.g., hypoxia, hypercarbia, acidosis, hypercapnia, a condition resulting from such, a condition having a manifestation of such (e.g., sleep apnea), etc., in accordance with the subject invention. For example, embodiments may include administering Aliskiren by mouth at about 2 mgs to about 10 mgs./day.

Estrogen and Analogues (e.g., Etradiols) and Metabolites

Embodiments may include administering estrogen and estrogen analogues and estrogen metabolites to treat a condition, e.g., hypoxia, hypercarbia, acidosis, hypercapnia, a condition resulting from such, a condition having a manifestation of such (e.g., sleep apnea), etc., in accordance with the subject invention. For example, embodiments may include administering about 10 mgs. three times per day.

Gonadotropin-releasing Hormone Inhibitors

Embodiments may include administering a gonadotropin-releasing hormone inhibitor to treat a condition, e.g., hypoxia, hypercarbia, acidosis, hypercapnia, a condition resulting from such, a condition having a manifestation of such (e.g., sleep apnea), etc., in accordance with the subject invention. For example, embodiments may include administering leuprolide acetate at about 65 mgs. SQ (subcutaneous) implant.

Vesicular Monoamine Transport (VMAT) Inhibitors

Embodiments may include administering a VMAT inhibitor to treat a condition, e.g., hypoxia, hypercarbia, acidosis, hypercapnia, a condition resulting from such, a condition having a manifestation of such (e.g., sleep apnea), etc., in accordance with the subject invention. For example, embodiments may include administering tetrabenazine by mouth at about 150 mgs. to about 200 mgs. once per day. Embodiments may also include administering reserpine at about 50 micrograms to about 500 micrograms one time per day.

Melatonin

Embodiments may include administering melatonin to treat a condition, e.g., hypoxia, hypercarbia, acidosis, hypercapnia, a condition resulting from such, a condition having a manifestation of such (e.g., sleep apnea), etc., etc., in accordance with the subject invention. For example, embodiments may include administering melatonin by mouth at about 0.5 mgs. to about 3.0 mgs. once per day.

Testosterone Inhibitors

Embodiments may include administering a testosterone inhibitor to treat a condition, e.g., hypoxia, hypercarbia, acidosis, hypercapnia, a condition resulting from such, a condition having a manifestation of such (e.g., sleep apnea), etc., in accordance with the subject invention. For example, embodiments may include administering spironolactone by mouth at about 100 mgs. to about 300 mgs. in divided doses two times per day. Embodiments may include administering cyproterone acetate by mouth at about 100 mgs. to about 150 mgs. once per day.

Dipeptidyl Peptidase (DP) IV Inhibitors (DP4 Inhibitors)

Embodiments may include administering a DP4 inhibitor to treat a condition, e.g., hypoxia, hypercarbia, acidosis, hypercapnia, a condition resulting from such, a condition having a manifestation of such (e.g., sleep apnea), etc., in accordance with the subject invention. For example, embodiments may include administering LAF237 by mouth at about 25 mgs. to about 200 mgs. per day.

Anti-coagulants

Embodiments may include administering an anti-coagulant to treat a condition, e.g., hypoxia, hypercarbia, acidosis, hypercapnia, a condition resulting from such, a condition having a manifestation of such (e.g., sleep apnea), etc., in accordance with the subject invention. For example, embodiments may include administering about 0.25 mg/kg intravensou bolus of abciximab and/or a continuous intravenous infusion of about 0.125 m g/kg/min (to a maximum of about 10 m g/min) for a period of time, e.g., 12 hours. Embodiments may include adminiserting dipridamole (e.g., AGGRENOX or the like) orally, e.g., one capsule twice daily. Embodiments may include administering anagrlide (e.g., AGRILYN or the like) orally, e.g., initially 0.5 mg orally four times daily or 1 mg orally twice daily or lowest effective dose—to a maximum 10 mg/day. Embodiments may include administering clopiogrel (e.g., PLAVIX or the like) at 75 mg orally once daily. Embodiments may include administering dipridamole (e.g., PERSANTINE or the like) at 75 to 100 mg orally four times daily. Embodiments may include administering eptifabatide (e.g., INTEGRILIN or the like) via IV at 0.5 mcg/kg/min to 180 mcg/kg or 135 mcg/kg and/or (e.g., followed by) 0.5 mcg/kg/min×20-24 hours. Fro example IV bolus of 180 mcg/kg over 1-2 minutes followed by 2 mcg/kg/min (maximum 15 mg/hr) up to 72 hours. Embodiments may include administering ticlopidine (e.g., TICLID or the like) at 250 mg orally twice daily. Embodiments may include administering tirofibam (e.g., AGGRASTAT or the like) at 0.4 mcg/kg/min to 0.1 mcg/kg/min. Embodiments may include administering ardeparin (e.g., NORMIFLO or the like) at 50 units SC every 12 hours. Embodiments may include administering dalteparin (e.g., FRAGMIN or the like) at 2500 units to 5000 units SC onc daily or 120 units/kg to about 10,000 SC every 12 hours. Embodiments may include administering enoxaparin (e.g., LOVENOX or the like) at 30-40 mg SC once daily. Embodiments may include administering lepiudin (e.g., REFLUDAN or the like) at 0.4 mg/kg (max weight of 110 kg) over al 5-20 seconds followed by does of 0.15 mg/kg/hr (max weight of 110 kg)×2-10 days as needed. Embodiments may include administering alteplase (e.g., ACTIVASE), t-PA or the like) at 15 mg to 35 mg via IV, e.g., 15 mg via IV bolus followed by 30-35 mg via IV over about 60 minutes. Embodiments may include administering reteplase (e.g., RETEVASE or the like) at 10.8 units IV over 2 minutes repeated in 30 minutes. Embodiments may include administering streptokinase at 1.5 million units IV over 60 minutes. Embodiments may include administering aminocaproic acid (e.g., AMICAR or the like) at 4 to 5 grams orally or IV over 1 hour, then 1 gram as needed. Embodiments may include administering cilostazol (e.g., PLETAL or the like) at 50 to 100 mg orally twice daily. Embodiments may include administering pentoxifylline (e.g., TRENTAL or the like) at 400 mg orally three times daily with meals.

Beta Agonists:

As described above, embodiments may include administering an effective amount of a beta agonist to a subject to treat a condition, e.g., hypoxia, hypercarbia, acidosis, hypercapnia, a condition resulting from such, a condition having a manifestation of such (e.g., sleep apnea), etc., in accordance with the subject invention. Embodiments may include administering dosages of about 0.5 to about 1.0 micrograms/kilogram/minute of dobutamine intravenously, e.g., dosages of about 500 micrograms/ml to about 2000 micrograms/ml may be administered. Embodiments may include administering dosages of terbutaline at about 0.25 mg to about 0.5 mg intramuscularly ("IM"), e.g., not more than about 0.5 mg within a four hour period. Embodiments may include administering dosages of ritodrine at about 50 to about 350 micrograms per minute intravenously. Embodiments may include administering dosages of albuterol via nebulizer at about 0.5 ml of 0.5% inhalation solution with about 2.5 ml sterile saline solution given over about 5 to about 15 minutes three to four times per day. Embodiments may include administering dosages of metaproterenol via nebulizer every four hours wherein a vial containing 0.4% metaproterenol sulfate is equivalent to 0.2 ml of metaproterenol sulfate inhalation solution 5% diluted to 2.5 ml with normal saline.

Alpha Agonists:

As described above, embodiments may include administering an effective amount of an alpha agonist to a subject to treat a condition, e.g., hypoxia, hypercarbia, acidosis, hypercapnia, a condition resulting from such, a condition having a manifestation of such (e.g., sleep apnea), etc., in accordance with the subject invention. Embodiments may include administering dosages of phenylephrine, e.g., subcutaneously or intramuscularly: from 1 mg to about 10 mg., wherein the initial dose generally should not exceed 5 mg.; intravenously: from about 0.1 mg to about 0.5 mg., wherein generally the initial dose should not exceed 0.5 mg. Injections are typically not repeated more often than about every 10 to 15 minutes. Embodiments may include administering dosages of metaraminol subcutaneously at about 2 to about 10 mg for an interval of about 10 minutes.

Prednisone and Steroids:

As described above, embodiments may include administering an effective amount of prednisone or a steroid to a subject to treat a condition, e.g., hypoxia, hypercarbia, acidosis, hypercapnia, a condition resulting from such, a condition having a manifestation of such (e.g., sleep apnea), etc., in accordance with the subject invention. Embodiments may include administering dosages of prednisone or a steroid by mouth at about 5 to about 60 mg/day, once per day. For example, prednisone may be in the form of a solution, syrup or tablet and doses may be given once daily or every other day and about 2.5-15 mg may be taken by a subject 2-4 times daily.

Indirect Agents that Include Norepinephrine:

As described above, embodiments may include administering an effective amount of an indirect agents that include norepinephrine to a subject to treat a condition, e.g., hypoxia, hypercarbia, acidosis, hypercapnia, a condition resulting from such, a condition having a manifestation of such (e.g., sleep apnea), etc., in accordance with the subject invention. Embodiments may include administering dosages of ephedrine IM or IV at about 25 to about 50 mg once per day. Embodiments may include administering dosages of phenylpropanolamine by mouth at about 25 mg every four hours, up to about 150 mg/day. Embodiments may include administering dosages of ampthetamine by mouth at about 2.5 mg to about 60 mg once per day.

Epinephrine:

As described above, embodiments may include administering an effective amount of epinephrine to a subject to treat a condition, e.g., hypoxia, hypercarbia, acidosis, hypercapnia, a condition resulting from such, a condition having a manifestation of such (e.g., sleep apnea), etc., in accordance with the subject invention. Embodiments may include intravenously administering epinephrine at about 0.1 to about 0.25 mg (about 1 to about 2.5 ml of 1:10,000 solution) once every 20 to 30 minutes.

Norepinephrine:

As described above, embodiments may include administering an effective amount of norepinephrine to a subject to treat a condition, e.g., hypoxia, hypercarbia, acidosis, hypercapnia, a condition resulting from such, a condition having a manifestation of such (e.g., sleep apnea), etc., in accordance with the subject invention. Embodiments may include intravenously administering norepinephrine at about 0.5 to about 1.0 mg (about 5 to about 10 ml of 1:10,000 solution) once every 5 minutes.

Potassium Channel Blockers and Magnesium Channel Blockers:

As described above, embodiments may include administering an effective amount of a potassium channel blocker or a magnesium channel blocker to a subject to treat a condition, e.g., hypoxia, hypercarbia, acidosis, hypercapnia, a condition resulting from such, a condition having a manifestation of such (e.g., sleep apnea), etc., in accordance with the subject invention. Embodiments may include administering lithium by mouth at about 10 to about 60 mg/kg once per day. Embodiments may include administering valproate by mouth at about 10 to about 60 mg/kg once per day.

Acetylcholine

As described above, embodiments may include administering an effective amount of acetylcholine to a subject to treat a condition, e.g., hypoxia, hypercarbia, acidosis, hypercapnia, a condition resulting from such, a condition having a manifestation of such (e.g., sleep apnea), etc., in accordance with the subject invention. Embodiments may include administering acetylcholine in the form of eye drops at about 0.75 to about 10 milligrams/ml acetylcholine.

Cocaine:

As described above, embodiments may include administering an effective amount of cocaine to a subject to treat a condition, e.g., hypoxia, hypercarbia, acidosis, hypercapnia, a condition resulting from such, a condition having a manifestation of such (e.g., sleep apnea), etc., in accordance with the subject invention. Embodiments may include administering cocaine topically on mucus membranes, e.g., about 10% cocaine hydrochloride.

Amphetamines:

As described above, embodiments may include administering an effective amount of an amphetamine to a subject to treat a condition, e.g., hypoxia, hypercarbia, acidosis, hypercapnia, a condition resulting from such, a condition having a manifestation of such (e.g., sleep apnea), etc., in accordance with the subject invention. Embodiments may include administering an amphetamine by mouth at about 5 to about 10 mg per day, e.g., 10 mg/day in divided doses.

Ephedrine:

As described above, embodiments may include administering an effective amount of ephedrine to a subject to treat a condition, e.g., hypoxia, hypercarbia, acidosis, hypercapnia, a condition resulting from such, a condition having a manifestation of such (e.g., sleep apnea), etc., Embodiments may include administering ephedrine sulfate injection at about 10 to about 50 mg injected subcutaneously or intramuscularly (equivalent to 0.2 to 1.0 ml of 5% solution).

Terbutaline:

As described above, embodiments may include administering an effective amount of terbutaline to a subject to treat a condition, e.g., hypoxia, hypercarbia, acidosis, hypercapnia, a condition resulting from such, a condition having a manifestation of such (e.g., sleep apnea), etc., in accordance with the subject invention. Embodiments may include administering terbutaline intramuscularly at about 0.25 mg, e.g., one time, and typically not more than about 0.5 mg within a 4 hour period.

Dopamine:

As described above, embodiments may include administering an effective amount of dopamine to a subject to treat a condition, e.g., hypoxia, hypercarbia, acidosis, hypercapnia, a condition resulting from such, a condition having a manifestation of such (e.g., sleep apnea), etc., in accordance with the subject invention. Embodiments may include administering dopamine intravenously at about 2 to about 50 microgram/kg/minute, wherein each milliliter of a 40 mg/ml preparation contains 40 mg of dopamine hydrochloride (equivalent to 32.31 mg of dopamine base). Embodiments may also include administering levodopa (L-dopa) in combination with carbidopa taken by mouth, e.g., about 25 mg carbidopa (up to about 2500 mg per day) and about 100 mg levodopa one half tablet, daily. Embodiments may also include administering bromocriptine (e.g., available under the brand name PARLODEL) by mouth at about 1.25 to about 100 mg per day.

Dobutamine:

As described above, embodiments may include administering an effective amount of dobutamine to a subject to treat a condition, e.g., hypoxia, hypercarbia, acidosis, hypercapnia, a condition resulting from such, a condition having a manifestation of such (e.g., sleep apnea), etc., in accordance with the subject invention. Embodiments may include intravenously administering dobutamine at about 0.5 to about 1.0 microgram/kg/min (up to about 500 microgram/ml).

Antidiuretic Hormone ("ADH") (Also Known as Vasopressin):

As described above, embodiments may include administering an effective amount of ADH to a subject to treat a condition, e.g., hypoxia, hypercarbia, acidosis, hypercapnia, a condition resulting from such, a condition having a manifestation of such (e.g., sleep apnea), etc., in accordance with the subject invention. Embodiments may include subcutaneously or intramuscularly administering about 5 to about 10 units of AHD two or three times per day.

Oxytocin:

As described above, embodiments may include administering an effective amount of oxytocin to a subject to treat a condition, e.g., hypoxia, hypercarbia, acidosis, hypercapnia, a condition resulting from such, a condition having a manifestation of such (e.g., sleep apnea), etc., in accordance with the subject invention. Embodiments may include intravenously administering oxytocin (e.g., available under the brand name PITOCIN) at about 1 to about 2 mU/mm (solution of 1 ml (10 units) combined with 1,000 ml of a non hydrating diluent).

THC Cannabinoids:

As described above, embodiments may include administering an effective amount of THC cannibinoid to a subject to treat a condition, e.g., hypoxia, hypercarbia, acidosis, hypercapnia, a condition resulting from such, a condition having a manifestation of such (e.g., sleep apnea), etc., in accordance with the subject invention. Embodiments may include administering THC cannibinoid by rectal suppository at about 2.5 mg two times per day; or about 10 to about 20 mg one, two or three times per day by mouth; or 1 mg intravenously, e.g., one time; or about 200 mg once per day by mouth.

Electrostimulatory Devices

A number of different devices may be employed in accordance with the subject invention to electrically modulate a subject's autonomic nervous system to increase and/or decrease parasympathetic activity relative to sympathetic activity, where such devices are herein referred to as electrostimulatory devices. Such devices may be positioned directly on a targeted area, e.g., positioned below the skin of a subject directly on or adjacent a portion of the autonomic nervous system (e.g., one or more nerve fibers) such as an implantable device, or may be an external device (i.e., some or all of the device may be external to the subject. In accordance with the subject invention, one or more electrodes or electrical contacts may be positioned directly on or adjacent a targeted area of the autonomic nervous system, i.e., directly on or adjacent a portion of the parasympathetic and/or sympathetic system, where the one or more electrodes may be surgically implanted directly on or adjacent a targeted nerve fiber of a subject. In certain embodiments, an immunomodulator such as a steroid or the like, may be incorporated into a surface contacting area of a device, e.g., to minimize inflammation of the targeted nerve(s). In further describing the subject invention, a single electrode is described however it is to be understood that multiple electrodes may be employed and features and characteristics of the single electrode described herein are applicable to any other electrodes that may be employed in the practice of the subject invention.

An electrostimulatory device typically includes a stimulator such as an electrode, a controller or programmer and one or more connectors for connecting the stimulating device to the controller. In certain embodiments more than one electrode may be employed. In further describing representative electrodes, such are described in the singular, but it will be apparent that more than one electrode may be used, where such may be the same or may be different in one or more aspects. Accordingly, the description of a representative electrode suitable for use in the subject methods is applicable to other electrodes that may be employed.

The electrode employed in the subject invention is controllable to provide output signals that may be varied in voltage, frequency, pulse width, current and intensity. The electrode is typically one that provides both positive and negative current flow from the electrode and/or is capable of stopping current flow from the electrode and/or changing the direction of current flow from the electrode. For example, embodiments include an electrode that is controllable in these respects, i.e., controllable in regards to producing positive and negative current flow from the electrode, stop current flow from the electrode, change direction of current flow from the electrode, and the like. In certain embodiments, the electrode has the capacity for variable output, linear output and short pulse width.

The energy source for the electrical output is provided by a battery or generator such as a pulse generator that is operatively connected to the electrode. The energy source may be positioned in any suitable location such as adjacent to the electrode (e.g., implanted adjacent the electrode), or a remote site in or on the subject's body or away from the subject's body in a remote location and the electrode may then be connected to the remotely positioned energy source using wires, e.g., may be implanted at a site remote from the electrode or positioned outside the subject's body in certain instances. Of interest are implantable generators analogous to a cardiac pacemaker.

The electrode may be mono-polar, bipolar or multi-polar. In order to minimize the risk of an immune response triggered by the subject against the device and minimize damage such as corrosion and the like to the device from other biological fluids, etc., the electrode and any wires and optional housing materials are made of inert materials such as for example silicon, metal, plastic and the like. For example, a multi-polar electrode having about four exposed contacts (e.g., cylindrical contacts may be employed.

A variety of methods may be used to endoscopically or surgically implant the electrode on or adjacent at least a portion of the autonomic nervous system such as on or adjacent one or more nerve fibers of the parasympathetic nervous system and/or sympathetic system. Because some nerve fibers may be in very close proximity to one another within a very small area, an analogous technique may generally be employed to provide operable placement of the electrode on or adjacent to any targeted area of the autonomic nervous system. Accordingly, for purposes of the following discussion, it shall be assumed that the inventive method of surgical implantation is being employed to implant the electrode on or adjacent to the vagus nerve, where such is for exemplary purposes only and is in no way intended to limit the scope of the invention. It should also be understood that, because the region in which the vagus nerve resides is very small, application of electrical impulses to the vagus nerve, even when the electrode is placed directly on the vagus nerve may also affect one or more other nerves.

A controller or programmer is also typically included in an electrostimulatory device. The programmer is typically one or more microprocessors under the control of a suitable software program. Other components of the programmer will be apparent to those of skill in the art, e.g., analog to digital converter, etc.

The electrostimulatory device is typically pre-programmed for desired parameters. In many embodiments the parameters are controllable such that the electrode signal may be remotely modulated to desired settings without removal of the electrode from its targeted position. Remote control may be performed, e.g., using conventional telemetry with an implanted electric signal generator and battery, an implanted radiofrequency receiver coupled to an external transmitter, and the like. In certain embodiments, some or all parameters of the electrode may be controllable by the subject, e.g., without supervision by a physician. For example, a magnetic signal may be employed. In such embodiments, one or more magnets may be employed such that upon bringing a magnet in proximity to or away from the power source such as a pulse generator, the magnet may be employed to interfere with the electronic circuitry thus modulating the power—either increasing or decreasing the power supplied depending on whether the magnet is brought in proximity or moved away from the power source.

FIG. 1 shows an exemplary embodiment of a subject electrostimulatory device 100. Device 100 may be implanted as shown in the abdomen or any other suitable portion of a subject's body 10. One or more leads 23 are shown positioned to electrically stimulate and/or inhibit activity in one or more area of the autonomic nervous system. Device 100 include energy source 14 which may take the form of a modified signal generator Model 7424 manufactured by Medtronic, Inc. under the trademark Intrel II. Lead 23 may take the form of any suitable lead, such as any of the leads that are sold with the Model 7427 and is coupled to energy source 14 by one or more conventional conductors 16 and 18. Lead 23 may include a paddle lead, a lead having one or more electrodes and/or catheters, or a combination catheter/lead capable of providing electrical impulses and pharmacological delivery. In certain embodiments, a lead may be composed of concentric tubes such as made of platinum or other like material. The tubes may be coated with a polymer except for the distal portions that may serve as the electrodes. Conductive wires carrying energy to the electrodes may be in the interior of the concentric tubes. Optionally, a distal electrode end may include a small recording microelectrode to help assist in the actual placement of the lead.

As noted above, the present invention may be operated as an open-loop controlled system. In an open-loop system, the physician or patient may at any time manually or by the use of pumps or motorized elements adjust treatment parameters such as pulse amplitude, pulse width, pulse frequency, or duty cycle. Optionally, the present invention may incorporate a closed-loop control system which may automatically adjust the electrical parameters in response to a sensed symptom or an important related symptom indicative of the extent of the condition being treated. Under a closed-loop feedback system to provide automatic adjustment of parameters of the electrodes, a sensor that senses a condition of the body is utilized. More detailed descriptions of sensors that may be employed in the practice of the subject invention, and other examples of sensors and feedback control techniques that may be employed are disclosed in U.S. Pat. No. 5,716,377, which is incorporated herein by reference.

As shown in FIG. 1, the distal end of lead 23 terminates in one or more therapy delivery elements such as stimulation electrodes which may be implanted on or about a portion of the autonomic nervous system using conventional surgical techniques. The type of treatment that is desired determines the location of the electrodes. Any number of electrodes may be used for various applications. Each of the electrodes is usually individually connected to energy source 14 through lead 23 and conductors 16 and 18. Lead 23 may be surgically implanted either by a laminotomy or by a needle.

Energy source or signal generator 14 may programmed to provide a predetermined stimulation dosage in terms of pulse amplitude, pulse width, pulse frequency, or duty cycle. As shown, a programmer 20 may be utilized to provide stimulation parameters to the therapy delivery device via any suitable technology, e.g., using telemetry and the like. For example, in using telemetry, programmer 20 may be coupled to an antenna 24 via conductor 22. In certain embodiments, the programmer may be positioned, e.g., implanted, inside body 10 . For example, in certain embodiments the programmer may be integrated with the energy source, electrode, etc., for example as a single unit.

Device 100 may optionally include one or more sensors to provide closed-loop feedback control of the treatment therapy and/or electrode positioning. One or more sensors (not shown) may be attached to or implanted into a portion of a subject's body suitable for detecting a physical and/or chemical symptom or an important related symptom of the body. For example, sensing feedback may be accomplished, e.g., by a mechanical measure within a lead or an ultrasound or other sensor to provide information about the treatment parameters, lead positioning, autonomic nervous system activity, etc. Suitable sensors that may be employed in the practice of the subject invention are described above.

Operative placement of a suitable electrostimulatory device may be accomplished using any suitable technique. In further describing exemplary techniques, the vagus nerve is used as an exemplary nerve and is in no way intended to limit the scope of the invention. In general, such placement includes localization of an area of the autonomic nervous system, e.g., the vagus nerve, positioning the electrode on or adjacent the area, e.g., the vagus nerve, and attaching the electrode to a power source. However, with regard to attaching the electrode to a power source, it should be understood that electrodes may be employed which make the implantation and/or attachment of a separate power source unnecessary. For example, an electrode may be employed which includes its own power source, e.g., which is capable of obtaining sufficient power for operation from surrounding tissues in the patient's body or which may be powered by bringing a power source external to the patient's body into contact with the patient's skin, or may include an integral power source, and the like. In such instances, the surgical procedure may be completed upon implantation of the electrode on or adjacent to the vagus nerve.

An electrode introducer needle may be employed to implant the electrode on or proximate to the area of interest, e.g., the vagus nerve. The size of the introducer needle may vary depending on the diameter of the electrode, etc., where in certain embodiments the electrode introducer needle may be a 12-gauge, 14-gauge, 16-gauge, 18-gauge, 20-gauge needle or 22-gauge needle, e.g., an electrode introducer needle available from Radionics in the Sluyter-Mehta kit as SMK 100 mm 2 mm active tip cannula. However, it should be understood that other electrode introducer needles may be used as appropriate to the needs and skill level of the practitioner performing the surgical procedure.

At least one imaging apparatus such as a CT scan, MRI apparatus, ultrasound apparatus, fluoroscope, or the like, may be employed to monitor the surgical procedure during the localization of the vagus nerve. For exemplary purposes only, the subject method will be described using a fluoroscope, where such is in no way intended to limit the scope of the invention. The subject is placed in a suitable position for access to the vagus nerve, e.g., supine, on a fluoroscopy table, with the patient's nose pointing vertically. The fluoroscope is then adjusted to a straight lateral position. And the entry point for the insertion of the electrode is determined.

Once the entry point is determined, the skin overlying the entry point is shaved and prepared with antiseptic solution. A 25-gauge needle may be used to inject a subcutaneous local anesthetic (such as, for example, 2 cc of 2% lidocaine) into the skin and subcutaneous tissues overlying the entry point. In addition to the local anesthetic, the patient may be given intravenous sedation and prophylactic antibiotics prior to commencement of the implantation procedure if desired.

The electrode introducer needle is inserted at the entry point and advanced. The fluoroscope may be adjusted as the needle is advanced. For example, if it is desired to place the electrode on or adjacent to the vagus nerve, the needle may be directed slightly posteriorly to the opening of the pterygoid or Vidian canal. Although the resolution of the fluoroscopy may be limited, it may be used to verify the positioning of the needle on or proximate to the vagus nerve.

Once the needle is positioned according to whether implantation is desired on or adjacent the vagus nerve for example, the stylet is withdrawn from the electrode introducer needle. A "test" electrode, if employed, used to test the placement of the electrode introducer needle may then be positioned within the central channel of the needle. If a "test" electrode is not employed, the electrode that is to be employed to modulate the autonomic nervous system may then be positioned within the central channel of the needle. The electrode may then be advanced to the distal tip of the needle to place the electrode on or proximate to the vagus nerve.

In certain embodiments, the "test" electrode may be a radiofrequency stimulating electrode suitable to electrically stimulate the tissue at the end of the tip of the electrode and verify its position physiologically within the patient, which may be a different electrode than that ultimately implanted within the patient. A suitable radiofrequency stimulating electrode may be 10 cm with a 2-mm non-insulated active tip. The electrode should fit the full length of the central channel of the needle with its non-insulated active tip protruding through the tip of the needle to expose the electrical contacts. An exemplary electrode that may be employed for this purpose electrode is produced by Radionics as the 100 mm thermocouple electrode in the SMK kit. Once the "est" electrode is inserted through the electrode introducer needle with its electrical contacts exposed, it may then be connected to an electrical stimulus/lesion generator for electrical stimulation.

The frequency of stimulation may be set at any suitable frequency, e.g., at about 50 Hz, and the voltage may be gradually increased until the subject reports tingling commensurate with stimulation of or about the area of interest of the autonomic nervous system, e.g., the vagus nerve. For example, in those embodiments targeting the vagus nerve, the vagus nerve is located in the posterior aspects of the sphenopalatine fossa and as such the electrode introducer needle may be placed in the sphenopalatine fossa as posteriorly as possible so that it may be positioned adjacent to the vagus nerve as it emerges from the pterygoid canal. Repositioning of the electrode may be performed as necessary.

If a "test" electrode is employed to test the placement of the electrode introducer needle and as such is different from the electrode to be employed to modulate the autonomic nervous system (i.e., the electrode to be implanted if it is desired to implant the electrode that will be employed to modulate the autonomic nervous system), the "test" electrode may then be removed from the electrode introducer needle while the needle is held firmly in place to prevent displacement. The electrode to be implanted may then be inserted through the central channel of the needle while the needle is held in place at the hub. Once the electrode to be implanted is in position, fluoroscopic imaging and electrical stimulation may be employed to verify the correct positioning of the needle and the electrode. Alternatively, if the electrode used to test the placement of the electrode introducer needle is the electrode to be implanted, the electrode should be left in the final test position.

Once the implanted electrode is in place, the end of the electrode that is outside the skin is carefully held in place against the skin. The electrode introducer needle may then be slowly removed, leaving the implanted electrode in place. At this point, if desired, a few small subcutaneous sutures may be placed around the electrode to hold it in the desired position.

Once the needle has been completely removed and the implanted electrode is in the final position, then the proximal part of the electrode that is coming out of the skin may be secured to the skin of the subject, e.g., by adhesive tape. Additionally, a small incision may be made on the skin at the area the electrode exits the face. Then several subcutaneous sutures may be placed around the electrode to hold it in place. The distal end of the electrode may then be connected to an extension wire or catheter, which is tunneled to the subclavicular area, or another region which will house the device used as an energy source for the implanted electrode. The device or devices used to control or stimulate the electrode may be surgically implanted in the desired region by procedures known in the art, such as have been applied in surgical neuromodulation therapies used to treat Parkinson's disease.

In certain embodiments of the subject invention, an electrode may be utilized which, instead of or in addition to delivering electric impulses to at least a portion of the autonomic nervous system, delivers a pharmacological agent to at least a portion of the autonomic nervous system. For example, an electrode may be used that has a small port at its tip which is connected to a reservoir or pump containing a pharmacological agent. The pharmacological agent delivery electrode may be implanted using an analogous procedure as that described above for the autonomic system modulating-electrode. In certain embodiments the reservoir or pump may also be implanted in the subject's body, analogous to that described above for the electrical impulse generator. The pharmacological agent delivery electrode may be controllable such that the amount of pharmacological agent delivered, the rate at which the pharmacological agent may be delivered, and the time period over which the pharmacological agent is delivered may be adjusted.

The above-described methods find use in a variety of different applications, representative types of which are described in greater detail below.

Utility

The subject methods find use in a variety of applications in which it is desired to treat a subject for a condition caused by an abnormality in the subject's autonomic nervous system. In such methods, at least a portion of a subject's autonomic nervous system is electrically and/or pharmacologically modulated to increase and/or decrease the parasympathetic activity/sympathetic activity ratio. As indicated above, in many embodiments of this type of application, the subject methods are employed to treat a condition in the subject in order to achieve a desired therapeutic outcome.

The subject methods find use in the treatment of a variety of different conditions in which an abnormality in a subject's autonomic nervous system exists. By treatment is meant that at least an amelioration of the symptoms associated with the condition afflicting the subject is achieved, where amelioration is used in a broad sense to refer to at least a reduction in the magnitude of a parameter, e.g. symptom, associated with the condition being treated. As such, treatment also includes situations where the condition, or at least symptoms associated therewith, are completely inhibited, e.g. prevented from happening, or stopped, e.g. terminated, such that the subject no longer suffers from the condition, or at least the symptoms that characterize the condition. In certain embodiments, the condition being treated is a disease condition.

A variety of subjects are treatable according to the subject methods. In many embodiments the subjects are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the subjects are humans.

As noted above, abnormalities in a subject's autonomic nervous system include those characterized by an abnormally high parasympathetic activity or abnormally low parasympathetic activity and/or an abnormally high sympathetic activity or abnormally low sympathetic activity. There are numerous conditions that the inventors of the subject invention have, unexpectedly, discovered are at least partially manifested by abnormal balance of the sympathetic and parasympathetic functions of the autonomic nervous system, particularly those that manifest higher than normal (as defined by those seen in healthy individuals between the ages of about 20 to about 25 years old) ratio of sympathetic function to parasympathetic function, which may be treated in accordance with the subject invention. Examples of conditions that may be treated with the methods of the subject invention include, but are not limited to, cardiovascular diseases, e.g., atherosclerosis, coronary artery disease, hypertension, hyperlipidemia, cardiomyopathy, volume retention; neurodegenerative diseases, e.g., Alzheimer's disease, Pick's disease, dementia, delirium, Parkinson's disease, amyotrophic lateral sclerosis; neuroinflammatory diseases, e.g., viral meningitis, viral encephalitis, fungal meningitis, fungal encephalitis, multiple sclerosis, charcot joint; myasthenia gravis; orthopedic diseases, e.g., osteoarthritis, inflammatory arthritis, reflex sympathetic dystrophy, Paget's disease, osteoporosis; lymphoproliferative diseases, e.g., lymphoma, lymphoproliferative disease, Hodgkin's disease; autoimmune diseases, e.g., Graves disease, hashimoto's, takayasu's disease, kawasaki's diseases, arthritis, scleroderma, CREST syndrome, allergies, dermatitis, Henoch-schlonlein purpura, goodpasture syndrome, autoimmune thyroiditis, myasthenia gravis, Reiter's disease, lupus, rheumatoid arthritis; inflammatory and infectious diseases, e.g., sepsis, viral and fungal infections, wound healing, tuberculosis, infection, human immunodeficiency virus; pulmonary diseases, e.g., tachypnea, fibrotic diseases such as cystic fibrosis, interstitial lung disease, desquamative interstitial pneumonitis, non-specific interstitial pneumonitis, lymphocytic interstitial pneumonitis, usual interstitial pneumonitis, idiopathic pulmonary fibrosis; transplant-related side effects such as rejection, transplant-related tachycardia, renal failure, typhlitis; transplant related bowel dysmotility, transplant-related hyperreninemia; sleep disorders, e.g., insomnia, obstructive sleep apnea, central sleep apnea; gastrointestinal disorders, e.g., hepatitis, xerostomia, bowel dysmotility, peptic ulcer disease, constipation, post-operative bowel dysmotility; inflammatory bowel disease; endocrine disorders, e.g., hypothyroidism, hyperglycemia, diabetes, obesity, syndrome X; cardiac rhythm disorders, e.g., sick sinus syndrome, bradycardia, tachycardia, QT interval prolongation arrhythmias, atrial arrhythmias, ventricular arrhythmias; genitourinary disorders, e.g., bladder dysfunction, renal failure, hyperreninemia, hepatorenal syndrome, renal tubular acidosis, erectile dysfunction; cancer; fibrosis; skin disorders, e.g., wrinkles, cutaneous vasculitis, psoriasis; aging associated diseases and conditions, e.g., shy dragers, multi-system atrophy, osteoporosis, age related inflammation conditions, degenerative disorders; autonomic dysregulation diseases; e.g., headaches, concussions, post-concussive syndrome, coronary syndromes, coronary vasospasm; neurocardiogenic syncope; neurologic diseases such as epilepsy, seizures, stress, bipolar disorder, migraines and chronic headaches; conditions. related to pregnancy such as amniotic fluid embolism, pregnancy-related arrhythmias, fetal stress, fetal hypoxia, eclampsia, preeclampsia; conditions that cause hypoxia, hypercarbia, hypercapnia, acidosis, acidemia, such as chronic obstructive lung disease, emphysema, cardiogenic pulmonary edema, non-cardiogenic pulmonary edema, neurogenic edema, pleural effuision, adult respiratory distress syndrome, pulmonary-renal syndromes, interstitial lung diseases, pulmonary fibrosis, and any other chronic lung disease; sudden death syndromes, e.g., sudden infant death syndrome, sudden adult death syndrome; vascular disorders, e.g., acute pulmonary embolism, chronic pulmonary embolism, deep venous thrombosis, venous thrombosis, arterial thrombosis, coagulopathy, aortic dissection, aortic aneurysm, arterial aneurysm, myocardial infarction, coronary vasospasm, cerebral vasospasm, mesenteric ischemia, arterial vasospasm, malignant hypertension; primary and secondary pulmonary hypertension, reperfusion syndrome, ischemia, cerebral vascular accident, cerebral vascular accident and transient ischemic attacks; pediatric diseases such as respiratory distress syndrome; bronchopulmonary dysplasia; Hirschprung disease; congenital megacolon, aganglionosis; ocular diseases such as glaucoma; and the like.

For example, conditions that promote maladaptive sympathetic bias may be treated with the subject invention. The inventors of the subject invention have realized that, unexpectedly, maladaptive sympathetic bias is a distinct syndrome that may be implicated in a number of fatal or potentially fatal conditions. Normally, the sympathetic drive is an adaptive response to dynamic physiological demands of the body. Under certain conditions, the response may become maladaptive. The inventors of the subject invention have realized that dramatic impacts on the health and well-being of an individual, in certain instances, may be related to acute sympathetic challenge in the context of background chronic sympathetic bias.

Chronic sympathetic bias may occur in various situations. For example, it may occur when the normal sympathetic bias fails to correct a precipitating respiratory or metabolic abnormality. The inventors of the subject invention have realized that conditions such as sudden infant death syndrome ("SIDS"), sudden adult death syndrome ("SADS") including sudden death among pregnant women, obstructive sleep apnea ("OSA") and congestive heart failure ("CHF") may fall in this category and thus are conditions that may be treated, or rather prevented by the subject invention and/or conditions associated with these conditions may be treated according to the subject invention, e.g., hypercapnia and/or hypoxia and/or hypercarbia and/or acidosis resulting from these conditions and/or other associated conditions resulting from the conditions or from the hypercapnia and/or hypoxia and/or hypercarbia and/or acidosis such as for example associated inflammatory conditions. Furthermore, sustained sympathetic bias is also noted during pregnancy, presumably as an adaptive response. Some diseases, such as pheochromocytoma, are intrinsically adrenergic. Sympathetic bias may also be a maladaptive component of the aging process attributable to an inexorable functional decline in autonomic regulatory systems. In the context of sympathetic bias, the inventors have realized that an acute sympathetic episode, as a centrally or peripherally mediated response to acute behavioral, metabolic, or physiologic stressors such as fear, injury, hypoxia, hypercarpnia, hypercarbia, acidosis, sleep arousal, and physical activity, may increase the likelihood of fatal arrhythmias, QT-related and otherwise.

For example, conditions having a manifestation of chronic or acute hypoxia and/or hypercapnia and/or hypercarbia and/or acidosis, such as for example obstructive sleep apnea ("OSA") and other chronic conditions described herein which include, but are not limited to, conditions that disturb or alter circulating blood concentrations of $pO_2$, $pCO_2$ and pH, such as chronic obstructive pulmonary disease ("COPD"), primary pulmonary hypertension ("PPHTN"), secondary pulmonary hypertension ("SPHTN") and the like, may be treated in accordance with the subject invention, as well as the manifested circulating blood concentrations of $pO_2$, $pCO_2$ and pH. As noted above, treatment according to the subject invention may be continuous, intermittent or cyclical. Certain embodiments include performing a treatment protocol according to the subject invention at night time, e.g., while a subject is sleeping. For example, a pharmacological agent may be administered prior to a subject's bedtime and/or electrical modulation may be actuated during the time a subject is sleeping. Embodiments are further described primarily with reference to OSA as a condition having a manifestation of chronic or acute hypoxia and/or hypercapnia and/or hypercarbia and/or acidosis for exemplary purposes only and is in no way intended to limit the scope of the invention. It is to be understood that any condition having a manifestation of chronic or acute hypoxia and/or hypercapnia and/or hypercarbia and/or acidosis also contemplated.

Figure 2:
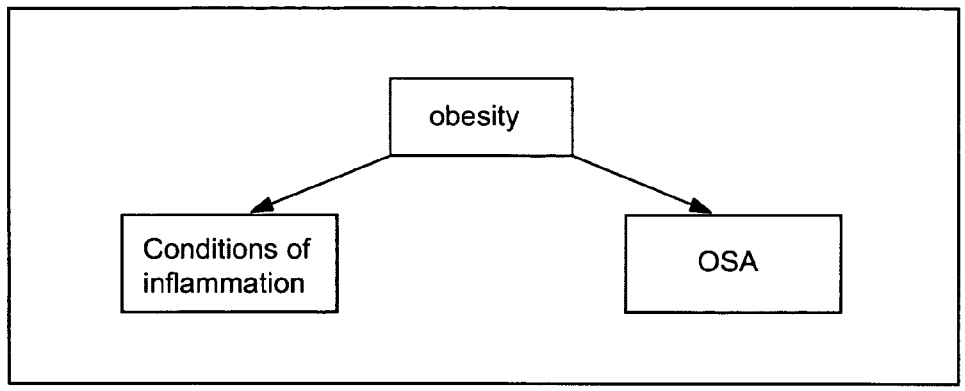
FIG. 2 shows a traditional view of the relationship between obstructive sleep disorder and conditions of inflammation.
Figure 3:
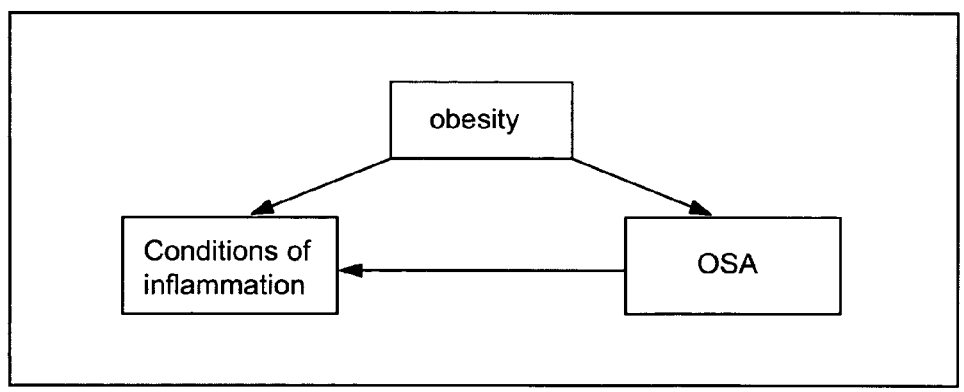
FIG. 3 shows a view of the relationship between obstructive sleep disorder and conditions of inflammation in accordance with the subject invention.

While not wanting to be tied to any particular theory or in any way limited by a particular theory, the inventors of the subject invention have discovered that excess sympathetic activity, relative to parasympathetic activity, elicited through, or rather a centrally or peripherally mediated response to, various changes in $pO_2$ and/or pH and/or $pCO_2$ brought about by a condition such as OSA (e.g., decreased $pCO_2$ and/or increased $pO_2$ and/or decreased pH), may account for many of the physiological consequences of OSA (and other chronic conditions that disturb or alter $pO_2$ and/or $pCO_2$ and/or pH levels in the body). FIG. 2 shows a traditional view of the relationship between OSA and conditions of inflammation and FIG. 3 shows a view of the relationship between OSA and conditions of inflammation (such as coronary artery disease (CAD), hypertension (HTN), diabetes mellitus (DM)) in accordance with the subject invention.

Embodiments also include treating an inflammatory consequences of a condition having a manifestation of chronic or acute hypoxia and/or hypercapnia and/or hypercarbia and/or acidosis, such as, but not limited to those described herein including, aging, cardiovascular conditions, neurodegenerative conditions, neuroinflammatory conditions, orthopedic inflammatory conditions, lymphoproliferative conditions, autoimmune conditions, infections diseases, pulmonary conditions, transplant-related side-effects, gastrointestinal conditions, endocrine conditions, cardiac rhythm conditions, genitourinary conditions, cancer, skin conditions, autonomic instability conditions, sudden death syndromes, atherosclerosis, hypertension, insulin resistance, diabetes, glaucoma, and the like.

Accordingly, embodiments the subject methods may be employed to treat a condition having a manifestation of chronic or acute hypoxia and/or hypercapnia and/or hypercarbia and/or acidosis such as OSA; an associated or resultant condition, such as OSA associated inflammatory conditions, that manifest from condition having a manifestation of chronic or acute hypoxia and/or hypercapnia and/or hypercarbia and/or acidosis, and well as chronic or acute hypoxia and/or hypercapnia and/or hypercarbia and/or acidosis.

Figure 4:
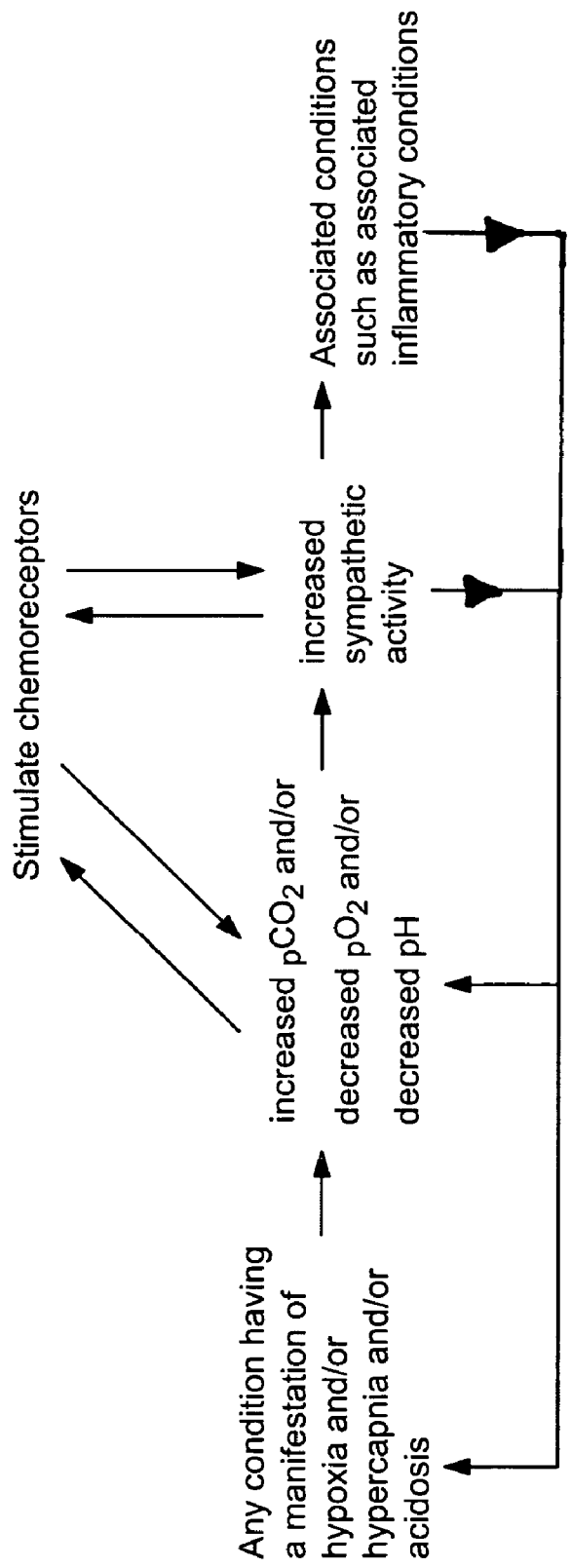
FIG. 4 shows aspects of conditions that cause hypoxia and/or hypercarbia and/or acidosis.

The subject invention realizes a link between the structural abnormalities of OSA (or other such conditions) to its physiological consequences, as shown schematically in the figures. FIG. 4 illustrates a condition such as OSA having a manifestation of chronic or acute hypoxia and/or hypercapnia and/or hypercarbia and/or acidosis.

In employing pharmacological agents in the practice of the subject invention, a variety of chemoreceptors may be targeted. For example, central chemoreceptors for hypercapnia are situated in the ventrolateral surface of the medulla. Peripheral chemoreceptors for are situated in the carotid and aortic bodies. Carotid bodies are more sensitive than aortic bodies to carotid decreased arterial pH, hypercarbia and hypoxia. The chemoreceptors are sensitive to hypoxia, but carotid bodies are sensitive to hypercapnia, particularly if hypoxia is also present. Chemoreceptors exist in other area of the body as well. Metalolo-receptors in skeletal muscles are activated in response to local metabolic acidosis, which then activate the sympathetic nervous system. Facial chemoreceptors respond to cold water on the face by increasing sympathetic vasoconstrictions and decreasing heart rate. This is a variant in the "cold-shower" effect that counters the parasympathetic-induced erectile function. Ventricular chemoreceptors react to myocardial ischemia by deceasing heart rate.

For example, embodiments may include targeting peripheral and/or central chemoreceptors as described above, e.g., chemoreceptors of one or more of the following: medulla, carotid bulb and aortic arch. For example, embodiments may include targeting a chemoreceptor using electrical energy applying devices and/or pharmacologically to decrease sensitivity of the chemoreceptor to increased concentrations of carbon dioxide, decreased concentrations of oxygen and decreased pH, e.g., by blocking completely or partially the chemoreceptor. Certain embodiments may target an afferent nerve carrying signal from a chemoreceptor, e.g., carrying signal to sympathetic nerves of the ANS. For example, conduction in an afferent nerve may be decreased. Efferent nerves may also be targeted. Such may be achieved using electrical energy (e.g., applied to an afferent nerve) and/or one or more pharmacological agents.

The inventors of the subject invention have also realized that OSA may have manifestation of endocrine disorders. Accordingly, embodiments of the subject invention employed to treat OSA may be employed to treat various endocrine abnormalities and embodiments of the subject invention employed to treat endocrine disorders may be employed to treat OSA. For example, embodiments may include modulating at least a portion of a subject's autonomic nervous system using electrical modulation (electrical energy applying device) and/or pharmacological modulation in a manner effective to increase sympathetic tone to treat a subject for OSA including the hypoxia, hypercapnia and pH resulting therefrom, and one or more endocrine conditions related to the OSA simultaneously, i.e., using the same treatment protocol, and vice versa.

As noted above, embodiments of the subject invention also include treating a subject for other chronic conditions having a manifestation of hypoxia and/or and/or hypercarbiaand/or hypercapnia and/or acidosis (i.e., a condition that disturbs body concentrations of circulating $pO_2$ and/or $CO_2$, and/or pH), such as, but not limited to, sleep apnea as noted above, acidemia, hypercapnia, hypoxia ventilation/perfusion (V/Q mismatch), emphysema, chronic obstructive pulmonary disease, primary pulmonary hypertension, secondary pulmonary hypertension, cyctic fibrosis, obesity, obesity hypoventilation syndrome, chronic pulmonary embolism, chronic infection, asthma, inhalational disorders, sarcoid, tuberculosis, pneumoconiosis, coal worker ling, asbestos, left-to-right-shunts, right-to-left shunts, cyanotic lung disease, vascular malformations, atrial septal defects, ventricular septal defects, patent ductus arteriosus, bronchopulmonary dysplasia, granulatomous lung diseases, heart failure, pulmonary edema, usual interstitial pneumonia (UIP), disquamative interstitial pneumonia (DIP), nonspecific interstitial pneumonia (NSIP), lymphocyctic interstitial pneumonia (LIP) acute interstitial pneumonia (AIP), rheumatoid arthritis, wegener's granulomatosis, unilateral pneumonectomy, ARDS, histocytosis, bronchiolitis obliterans organizing pneumonia (BOOP), pleural effusion, cancer, sudden death syndromes, congestive heart failure, pulmonary edema, cardiogenic pulmonary edema, non-cardiogenic pulmonary edema, neurogenic edema, emphysema, pulmonary fibrosis, obesity hypoventilation syndrome, HIV, scleroderma, other chronic lung diseases, and the like.

Embodiments of the subject methods may also be employed to treat acute conditions that disturb $pO_2$ and/or pH and/or $pCO_2$, such as, but not limited to, acute lung injury, acute pulmonary embolism, acute respiratory distress syndrome, asphyxiation, drowning, and the like.

Embodiments of the subject methods may also be employed to treat various other systemic conditions that disturb $pO_2$ and/or $pCO_2$ and/or pH such as, but not limited to, anemia, sickle cell disease, thalassemia, anion gap, non-anion gap, metabolic acidosis, renal tubular acidosis, drug induced acidosis, renal failure, uremia, and the like.

Certain embodiments may employ insulin-increasing or insulin-sensitizing agents to decrease inflammation and correct endocrine maladaptions that may occur as a consequence of changes in $pO_2$ and/or $pCO_2$ and/or pH. Such agents may include, but are not limited to, insulin, sulfonylureas, meglitinides (e.g., starlix), biguanides (e.g., metformin), thiazolidinedione-rosiglitiazone, exenatide, synthetic exendin-4, GLP, 1; and the like.

As noted above, embodiments of the subject invention may include monitoring or determining at least one of: (1) the state of the ANS prior to and/or during and/or after modulation of the ANS according to the subject invention; (2) monitoring or determining a condition having a manifestation of hypoxia and/or hypercapnia and/or hypercarbia and/or acidosis; (3) monitoring or determining hypoxia and/or hypercapnia and/or hypercarbia and/or acidosis; and (4) observing, monitoring or determining an effect or manifestation of any of the above or of any physiological or biologic aspect of a subject. Accordingly, embodiments may include, prior to and/or during and/or after modulation of the ANS to treat a subject for hypoxia and/or hypercapnia and/or hypercarbia and/or acidosis, and/or a condition that causes hypoxia and/or hypercapnia and/or hypercarbia and/or acidosis, and/or a condition resulting from hypoxia and/or hypercapnia and/or hypercarbia and/or acidosis and/or resulting from the condition causing hypoxia and/or hypercapnia and/or hypercarbia and/or acidosis, determining and/or monitoring-continuously or periodically, any of such conditions, including determining the state of the ANS, e.g., the parasympathetic activity/sympathetic activity ratio. For example, embodiments may include determining whether hypoxia and/or hypercapnia and/or hypercarbia and/or acidosis is present and in certain embodiments determining the pH and/or concentrations of oxygen and carbon dioxide. As described above, monitoring of one or more physiological or biologic functions of a subject may be employed in a feedback system whereby modulation of at least a portion of the ANS may be performed according to (i.e., tailored or based upon) an observed aspect of the subject. For example, in the case where erthythrocyte sedimentation rates (ERS) are monitored before and/or during and/or after ANS modulation, the particulars of a pharmacological modulation and/or electrical modulation may be based on the determined ERS such that the amount of agent or electrical stimulation may be continually or periodically adjusted until a predetermined, e.g., normal, ESR is obtained, at which time ANS modulation is terminated. For example, the dosage of a given agent may be based on a determined ESR. This monitoring and modulation of ANS may be performed automatically, e.g., by way of suitable componentry such that a physiological aspect of a subject may be repeatedly monitored a given ANS modulation protocol may be adjusted one or more times based on the results of the monitoring. In many embodiments, an ANS modulation protocol may be continued until a particular level or quality of one or more physiological or biologic aspects are obtained, i.e., a predetermined parameter may be targeted and the NS may be modulated until that predetermined parameter is achieved. In many embodiments, a targeted level or quality of a physiological and/or biologic aspect is analogous to the level or quality of a normal subject, as described above. In the below-described exemplary physiological aspects that may be described, reference values are indicated in parenthesis such that in certain embodiment a reference value may be a target value and once achieved, modulation of the ANS may be terminated. Accordingly, in certain embodiments a given ANS modulation protocol may be performed until a time at which a predetermined level or quality of a physiological aspect or biologic aspect of a subject is observed, such as a reference value.

Any suitable method may be employed for such observing, determining and monitoring where such methods are known in the art and include methods described herein.

In certain embodiments aspects measured during an overnight sleep study may be employed. Sleep study parameters include, but are not limited to the following: sleep state (EEG leads); electrooculogram; EMG; airflow at nose and mouth (via thernistor, capnography, mask and pneumotachygraph, or other methods); chest and abdominal wall motion (impedance or inductance plethysmography or other); electrocardiogram; pulse oximetry including pulse waveform; end tidal carbon dioxide; video camera monitoring with sound montage; transcutaneous oxygen and carbon dioxide tensions; nasal pressure flow measurements; esophageal manometry; continuous noninvasive blood pressure monitoring; autonomic nervous system tone using finger tonometry.

In certain embodiments, the determination of pulmonary gases may be employed (reference: alveolar oxygen 600-713 mm Hg).

In certain embodiments, the determination of serum blood gases may be employed (reference: ph range 7.1 to 7.7, $pCO_2$ range 10 mm Hg to 80 mm Hg, arterial $pO_2$ range from 50 mmHg to 110 mmHg, arterial bicarbonate range 10 meq to 40 meq/L, alveolar/oxygen ratio of 1.0 to 0.6, alveolar to arterial gradient of 5 to 120 mHg, venous oxygen saturation 30% to 80%).

In certain embodiments, the determination of cardiopulmonary physiological parameters may be employed that such as, but not limited to: cardiac output (reference: 1 to 6 L/min); cardiac index (reference: 0.5 to 6 L/min/m2); central venous pressure (reference: 3 to 30 cm H20); right atrial pressure (reference: 1-30 mm Hg); right ventricular systolic pressure (reference: 5 to 50 mm Hg); right ventricular diastolic pressure (reference: 1 to 50 mm Hg); pulmonary arterial systolic pressure (reference: 5 to 50 mm Hg,); pulmonary arterial diastolic pressure (reference: 1 to 30 mm Hg); mean pulmonary arterial pressure (reference: 5 to 50 mm Hg); pulmonary capillary wedge pressure (reference: 1 to 20 mm Hg);

In certain embodiments, the determination of pulmonary function and spirometry parameters may be employed that such as, but not limited to: tidal volume (reference: 2 mL/kg to 20 ml/kg or 20-80% of predicted); total lung capacity or TLC (reference: 3 to 10 liters or 20-120% of predicted); residual volume (reference: 0.5 to 5 L or 20-120% of predicted); forced expiratory volume in 1 second or FEV1 (reference: 0.5 to 6 liters or 20-120% of predicted); functional vital capacity or FVC (reference: 0.5 to 6 liters or 20-120% of predicted); FEV1/FVC ratio (reference: 20-120%); forced expiratory flow or FEF 25-75 (reference: 50 to 150%); peak expiratory flow rate (reference: 60-120%); forced expiratory time (reference: 0-20 seconds); corrected diffusion capacity or DLCO (reference: 60-140%)

Sleep study parameters that may be employed include, but are not limited to: sleep latency (reference: 0-1 hour); total sleep time (reference: 0-12 hours); percent REM sleep (reference 0-40% total sleep time); percent stage 3-4 non-REM sleep reference 0-50% of total sleep time); respiratory arousal index (reference 0-40/hour total sleep time); periodic leg movements (reference 0-40/hour total sleep time); apnea index (reference 0-20/hour of total sleep time); hypopnea index (reference 0-40/hour of total sleep time) nadir oxygen saturation (reference 40-100%); mean oxygen saturation (reference 40-100%); desaturation index (reference 0-40 defined as >4% for 5 seconds/hour of total sleep time); highest carbon dioxide (reference 10 to 80 mmHg); carbon dioxide >45 mm Hg (reference 0-60% of total sleep time);

Other serum measurements include, but are not limited to: determining acetylcholine levels (reference 300-2000 IU/L); determining aldosterone levels (reference 5-150 nmol/day); determining renin levels (reference 3-200 uU/mL); determining vasopressin levels (reference 1-20 pg/ml); determining angiotensin converting enzyme levels (reference 5-200 U/L); modulating interleukins 1-3 and 5-13 and interleukin 18); lowering interleukin-4; modulating interferon alpha and beta; increasinginterferon gamma; modulating tumor necrosis factor alpha modulating transforming growth factor levels; determining hemoglobin A1C levels (reference 2.0-12%); determining glucose levels (reference fasting 1.0-10.0 mmol/L); determining lipid levels (HDL and/or LDL) (reference high density lipoprotein cholesterol (reference range: 10-90), low density lipoprotein cholesterol (reference range: 60-200); determining triglyceride levels (reference 0.5 to 4.0 mmol/L); determining beta natriuretic peptide levels (reference 0-100 pg/mL); determining alpha natriuretic peptide levels (reference 0-50 pg/mL); determining erythrocyte sedimentation rate (ESR) (reference 1-200 mm/Hour); determining C-reactive protein (CRP) levels (reference 1-80 mg/L); determining transferrin levels (reference 0.5 to 6 g/L); determining hemoglobin levels (reference normal hemoglobin is 25 to 300 gm/L); determining hematocrit levels (reference 25-60%); determining serum ferritin levels (reference 5 to 600 µg/L); determining serum iron (reference 5 to 100 µmol/L); determining serum cholinesterase (reference—200-2500 IU/L); determining urine catecholamines (reference adrenaline 0-200 nmol/day; noradrenaline 0-1600 nmol/day; dopamine 0-7000 nmol/day); determining adrenocorticotrophic hormone (ACTH) (0 to 40 pmol/L); determining antidiuretic hormone (reference 1-20 pg/mL); determining thrombin clotting time (reference—5-30 seconds); determining serum total cholesterol (reference 100-300); and the like.

Other physiologic measurements include but are not limited to: determining body mass index (reference <40); determining systolic blood pressure (reference 90-180 mmHg); determining diastolic blood pressure (30-100 mmHg); determining pulse pressure (reference 20-40 mmHg); determining heart rate (reference 30-150 beats/min in adults, 30-200 beats/min in children); corrected QT interval (reference <600); increasing heart rate variability; increasing respiratory sinus arrhythmia.

In certain embodiments, based the outcomes of the one or more of the above, ANS modulation may be initiated, altered or terminated. In this manner, continual adjustments may be made to tailor a treatment protocol to a particular state of a subject.

As noted above, the subject methods may be employed to treat or rather prevent sudden infant death syndrome ("SIDS") and sudden adult death syndrome ("SADS"), including sudden death amongst pregnant women. In this regard, the inventors of the subject invention have discovered that in certain instances sympathetic bias may be implicated in SIDS and SADS.

More specifically, the inventors of the subject invention have unexpectedly realized that a maladaptive shift to sympathetic bias may be a key determinant of SIDS. Heart rate variability (HRV) is often used as a measure of autonomic balance. Decreased HRV, indicating sympathetic bias, has been observed in patients with central hypoventilation and in infants who have later succumbed to SIDS (see for example Edner A, Katz-Salamon M, Lagercrantz H, Ericson M, Milerad J. Heart rate variability in infants with apparent life-threatening events. Acta Paediatr. 2000 November;89 (11):1326-9).

This finding is consistent with other conditions of hypoxia such as respiratory distress syndrome and prenatal hypoxia which decrease HRV and induce tachycardia (see for example Aarimaa T, Oja R. Transcutaneous PO2, $PCO_2$ and heart rate patterns during normal postnatal adaptation and respiratory distress. Early Hum Dev. 1988 January; 16(1): 3-11), both indicators of sympathetic bias. Infants who experience near-miss SIDS demonstrate tachycardia and decreased HRV (see for example Reid GM. Sudden infant death syndrome: neonatal hypodynamia (reduced exercise level). Med Hypotheses. 2001 March;56(3):280-5). Food regurgitation and diaphoresis associated with SIDS may reflect excess sympathetic activity (see for example Kahn A, Groswasser J, Rebuffat E, Sottiaux M, Blum D, Foerster M, Franco P, Bochner A, Alexander M, Bachy A, Richard P, Verghote M, Le Polain D, Wayenberg L 1992 Sleep and cardiorespiratory characteristics of infants victims of sudden death: a prospective case-control study. Sleep 15: 287-292; Guntheroth W G, Spiers P S. Thermal stress in sudden infant death: Is there an ambiguity with the rebreathing hypothesis? Pediatrics. 2001 April;107(4):693-8; Uchino M, Ishii K, Kuwahara M, Ebukuro S, Tsubone H. Role of the autonomic nervous system in emetic and cardiovascular responses in Suncus murinus. Auton Neurosci. 2002 Sep. 30;100(1-2):32-40).

Inciting causes of sympathetic bias may be manifold. Hyperthermnia and fever, both of which have known associations with SIDS (see for example Kahn A, Groswasser J, Rebuffat E, Sottiaux M, Blum D, Foerster M, Franco P, Bochner A, Alexander M, Bachy A, Richard P, Verghote M, Le Polain D, Wayenberg L 1992 Sleep and cardiorespiratory characteristics of infants victims of sudden death: a prospective case-control study. Sleep 15: 287-292; Guntheroth W G, Spiers P S. Thermal stress in sudden infant death: Is there an ambiguity with the rebreathing hypothesis? Pediatrics. 2001 April;107(4):693-8) are hyperadregnergic states (see for example Rowell L B. Hyperthermia: a hyperadrenergic state. Hypertension. 1990 May;15(5):505-7). Infection and inflammation, which are associated with SIDS (see for example Krous H F, Nadeau J M, Silva P D, Blackboume B D. A comparison of respiratory symptoms and inflammation in sudden infant death syndrome and in accidental or inflicted infant death. Am J Forensic Med Pathol. 2003 March;24(1):1-8.), are also potential causes of sympathetic bias. In certain situations, the adaptive chemoreceptor-mediated sympathetic response of arousal and increased respiration may fail to correct the underlying hypoxia, hypercapnia, hypercarbia and acidosis, leading to a maladaptive sympathetic bias. The association of prone sleeping position, obstructive sleep apnea, and other respiratory conditions with SIDS (see for example Kahn A, Groswasser J, Rebuffat E, Sottiaux M, Blum D, Foerster M, Franco P, Bochner A, Alexander M, Bachy A, Richard P, Verghote M, Le Polain D, Wayenberg L 1992 Sleep and cardiorespiratory characteristics of infants victims of sudden death: a prospective case-control study. Sleep 15 :287-292; American Academy of Pediatrics, Task Force on Infant Sleep Position and Sudden Infant Death Syndrome. Changing concepts of sudden infant death syndrome: implications for infant sleeping environment and sleep position. Pediatrics.2000; 105 :650-656; Hoffman H J, Damus K, Hillman L, Krongrad E. Risk factors for SIDS: results of the National Institute of Child Health and Human Development SIDS Cooperative Epidemiological Study. Ann N Y Acad Sci 1988; 533: 13-30) may exemplify this phenomenon. In infants with OSA, as with their adult counterparts, the sympathetic bias can exacerbate sleep disturbance and can trigger insomnia (see for example Harrison G A. Stress, catecholamines, and sleep. Aviat Space Environ Med 1985; 56:651-653;.Montagna P, Gambetti P, Cortelli P, Lugaresi E. Familial and sporadic fatal insomnia. Lancet Neuro 2003 March; 2(3):167-176.), leading to a pernicious cycle.

Sympathetic bias has an association with QT interval prolongation, a risk factor for sudden cardiac death in adults (see for example Esposito K, Marfella R, Gualdiero P, Carusone C, Pontillo A, Giugliano G, Nicoletti G, Giugliano D. Sympathovagal Balance, Nighttime Blood Pressure, and QT Intervals in Normotensive Obese Women. Obes Res. 2003 May;11(5):653-9). Sympathetic bias may predispose infants to similar risks. A significant association between prolonged QT interval and SIDS victims or those who experienced apparent life-threatening event (ALTE) has been noted (see for example Goldhammer E I, Zaid G, Tal V, Jaffe M, Abinader E G. QT dispersion in infants with apparent life-threatening events syndrome. Pediatr Cardiol. 2002 November-December;23(6):605-7; Schwartz P J, Stramba-Badiale M, Segantini A, et al. Prolongation of the QT interval and the sudden infant death syndrome. N Engl J Med. 1998; 338 :1709-1714). Various theories for this association have been proposed, including development-related abnormalities in cardiac sympathetic innervation and genetic predisposition (see for example Stramba-Badiale M, Lazzarotti M, Schwartz P J. Development of cardiac innervation, ventricular fibrillation, and sudden infant death syndrome. Am J Physiol 1992;263:H1514-H1522; Ackerman, M. J., Siu, B. L., Sturner, W. Q., Tester, D. J., Valdivia, C. R., Makielski, J. C., Towbin, J. A. (2001). Postmortem Molecular Analysis of SCN5A Defects in Sudden Infant Death Syndrome. JAMA 286: 2264-2269; Schwartz P J. Cardiac sympathetic innervation and the sudden infant death syndrome: a possible pathogenetic link. Am J Med 1976; 60:167-172). The inventors of the subject methods have realized that maladaptive sympathetic response is the key determinant of SIDS, a broader view than that which had been held prior to the inventor's view.

The inventors of the subject invention have also realized that, unexpectedly, sudden death precipitated by maladaptive sympathetic bias, similar to those seen in infants, may account for a proportion of SADS cases.

For example, while obviously multifactorial in mechanism, conditions such as constipation, insomnia, erectile dysfunction, hypertension are endemic among the aged and are consistent with a broad physiologic bias towards sympathetic function. HRV and baroreflex sensitivity decreases with aging (see for example Stratton J R, Levy W C, Caldwell J H, Jacobson A, May J, Matsuoka D, Madden K. Effects of aging on cardiovascular responses to parasympathetic withdrawal. J Am Coll Cardiol. 2003 Jun. 4;41(11): 2077-83), consistent with a shift to sympathetic bias. The inventors have realized that, as in SIDS, some cases of SADS may reflect maladaptive chemoreceptor response to hypoxia, hypercapnia, hypercarbia and acidosis, all of which are common conditions seen in the elderly due to myriad of diseases. Examples of chronic diseases that exemplify this phenomenon include renal failure, congestive heart failure, chronic obstructive lung disease ("COPD") and chronic pain (see for example Wiggers H, Botker H E, Egeblad H, Christiansen E H, Nielsen T T, Molgaard H. Coronary artery bypass surgery in heart failure patients with chronic reversible and irreversible myocardial dysfunction: effect on heart rate variability. Cardiology. 2002;98(4):181-5). Heightened sympathetic function is seen in many other conditions including pheochromocytoma, autoimmune conditions, and collagen vascular diseases (see for example Lagana B, Gentile R, Vella C, Giovani A, Tubani L, Mastrocola C, Baratta L, Bonomo L. Heart and autonomic nervous system in connective tissue disorders. Recenti Prog Med. 1997 December;88(12)579-84; P. K. Stein, P. Nelson, J. N. Rottman et al., Heart rate variability reflects severity of COPD in PiZ alpha-1-antitrypsin deficiency. Chest 113 (1998), pp. 327-333). More broadly, the inventors have realized that attrition of parasympathetic function with aging may be an important but until now, unrecognized, culprit in generalized sympathetic bias of aging. For example, it has been observed that QT interval lengthens with aging and other chronic conditions that promote sympathetic bias such as COPD (see for example Wei, J. Y., Spurgeon, H. A. and Lakatta, E. G. (1984) Excitation-contraction in rat myocardium: alteration with adult aging. Am. J. Physiol. 246, H784-H791; Tukek T, Yildiz P, Atilgan D; Tuzcu V, Eren M, Erk O, Demirel S, Akkaya V, Dilmener M, Korkut F. Effect of diurnal variability of heart rate on development of arrhythmia in patients with chronic obstructive pulmonary disease. Int J Cardiol. 2003 April;88(2-3):199-206), putting the patient at increased risk of fatal arrhythmias.

Still further, pregnant women may exhibit various signs of sympathetic bias such as hyperemesis, hypertension, and increased cardiac output, and as such may be treated in accordance with the subject invention. More specifically, the inventors of the subject invention have realized that sympathetic bias in pregnant women may be responsible for sudden death in pregnant women. The shift to sympathetic bias may represent adaptations to the physiologic and immunologic demands of gestation (see for example Minagawa M, Narita J, Tada T, Maruyama S, Shimizu T, Bannai M, Oya H, Hatakeyama K, Abo T. Mechanisms underlying immunologic states during pregnancy: possible association of the sympathetic nervous system. Cell Immunol. Aug. 25, 1999;196(1):1-13). Pregnancy is associated with QT prolongation, increased plasma catecholamine levels, and decreased HRV, similar to the other augmented sympathetic states that increase risk for sudden death (see for example Gowda R M, Khan I A, Mehta N J, Vasavada B C, Sacchi T J. Cardiac arrhythmias in pregnancy: clinical and therapeutic considerations. Int J Cardiol. 2003 April;88(2-3):129-33; N. D. Averyl, L. A. Wolfe, C. E. Amara, G. A. L. Davies, and M. J. McGrath. Effects of human pregnancy on cardiac autonomic function above and below the ventilatory threshold J Appl Physiol 90: 321-328, 2001; Vol. 90, Issue 1, 321-328, January 2001). While an increase rate of sudden deaths from arrhythmias has been noted in pregnant women and has been attributed to hormonal influences (see for example Wolbrette D. Treatment of arrhythmias during pregnancy. Curr Womens Health Rep. 2003 April;3(2):135-9; Wolbrette D, Naccarelli G, Curtis A, Lehmann M, Kadish A. Gender differences in arrhythmias. Clin Cardiol. 2002 Febuary;25(2):49-56), the subject inventors have realized that sympathetic excess of pregnancy may be a potential cause. The most common manifestation of exaggeration of the normal sympathetic shift in pregnant women may be pre-eclampsia, which accounts for 80% of maternal mortality in developing countries (see for example Conz P A, Catalano C. Pathogenesis of pre-eclampsia. G Ital Nefrol. 2003 January-Febuary;20(1):15-22). Measurement of postganglionic action potentials reveal mean sympathetic activity to be three times higher in pre-eclamptic women compared with healthy pregnant women, and two times higher compared with the hypertensive non-pregnant women (see for example Schobel H P, Fischer T, Heuszer K, Geiger H, Schmieder R E. Preeclampsia—a state of sympathetic overactivity. N Engl J Med 1996; 335:1480-1485). HRV is reduced in pre-eclamptic women (see for example Yang C C, Chao T C, Kuo T B, Yin C S, Chen H I. Preeclamptic pregnancy is associated with increased sympathetic and decreased parasympathetic control of HR. Am J Physiol Heart Circ Physiol. 2000 April;278(4):H1269-73). Autonomic imbalance appears to particularly affect the central nervous system. Seizures, a common morbidity of pre-eclampsia, and acute cerebral vasoconstriction, the most common cause of mortality, may both be viewed as acute adrenergic phenomenon (see for example Novak V V, Reeves L A, Novak P, Low A P, Sharbrough W F. Time-frequency mapping of R-R interval during complex partial seizures of temporal lobe origin. J Auton Nerv Syst. Sep. 24, 1999;77(2-3):195-202). Seizure is also a common presentation among the aged, with 25% of new cases of epilepsy diagnosed in the elderly (see for example Stephen L J, Brodie M J. Epilepsy in elderly people. Lancet. 2000 Apr. 22;355(9213):1441-6).

Furthermore, as noted above, the subject invention may be employed to treat or prevent congestive heart failure ("CHF"), another situation in which chronic sympathetic bias may be implicated as an underlying cause.

The inventors of the subject invention have also discovered that, unexpectedly, many conditions of aging are manifestations of sympathetic bias that is unmasked by withdrawal of autonomic function, particularly the parasympathetic system. For example, in regards to employing the subject methods in the treatment of aging associated conditions, the inventors of the subject invention have realized that many clinical consequences of aging are pleiotropic manifestations of the loss of parasympathetic function that occurs during post-reproductive senescence. The inventors realized that the loss of parasympathetic function unmasks the baseline sympathetic bias inherent in the end-organs, resulting in the familiar signs of aging including tachycardia, constipation, insomnia, erectile dysfunction, fluid retention, and systemic inflammation. These consequences in turn may contribute to many of the common diseases associated with aging including type-2 diabetes, Alzheimer's, atherosclerosis, and cancer. Maintenance and restoration of parasympathetic function may enable upstream control over the deleterious aspects of inherent end-organ adrenergic bias.

More specifically, aging is marked by a compendium of physiologic and biologic dysfunctions. The inventors of the subject invention have realized that many seemingly unrelated consequences of aging are, at least in part, manifestations of a single upstream phenomenon: an emergent sympathetic bias that is unmasked by loss of parasympathetic function during post-reproductive senescence and may be treated using the subject methods. Common symptomatic presentations among the elderly include dysphagia, constipation, insomnia, anorexia, bladder dysfunction, hypertension, erectile dysfunction, and heart arrhythmias. These symptoms are the final common pathways of many different complex physiologic disturbances and iatrogenic circumstances. These symptoms also represent the classic organ-specific manifestations of excess adrenergic tone.

The inventors of the subject invention realized that if sympathetic excess is the dominant biologic theme during senescence, the mechanisms may be a loss of parasympathetic function. It is known that the vagus nerve shows decreased activity with age (see for example Tulppo M. P., Makikallio T. H., Seppanen T., et al. Vagal modulation of heart rate during exercise: effects of age and physical fitness. Am J Physiol 1998 February; 274(2 Pt 2): H424-9). In the gastrointestinal system, the attrition of vagal and myenteric innervation has been noted with advancing age (see for example Phillips R. J., Powley T. L. As the gut ages: timetables for aging of innervation vary by organ in the Fischer 344 rat. J Comp Neurol Jun. 4, 2001; 434(3):358-77). In the bladder, waning parasympathetic function has been noted and is one of the targets for treating dysfunctional bladder (see for example Anderson K. E., Hedlund P. Pharmacologic perspective on the physiology of the lower urinary tract. Urology 2002 November; 60(5 Suppl 1):13-20).

The inventors of the present invention have also realized that loss of parasympathetic tone may also explain the somewhat paradoxical emergence of bradycardia during aging. The cardiac conduction system displays decreased intrinsic function with age, often termed the "sick sinus syndrome". As aging and senescence occurs, the heart loses parasympathetic innervation without concomitant decrease in sympathetic function (see for example Brodde O. E., Konschak U., Becker K. et al. Cardiac muscarinic receptors decrease with age. In vitro and in vivo studies. J Clin Invest 1998 Jan. 15; 101(2):471-8; Ebert T. J., Morgan B. J., Barney J. A., et al. Effects of aging on baroreflex regulation of sympathetic activity in humans. Am J Physiol 1992 September; 263(3 Pt 2):H798-803). The adrenergic excess eventually induces focal inflammation and fibrosis of the conduction system irrespective of ischemic changes (see for example Fujino M., Okada R., Arakwa K. The relationship of aging to histological changes in the conduction system of the normal human heart. Jpn Heart J 1983 January; 24(1): 13-20). Thus, despite the local sympathetic bias, bradycardia ensues.

Accordingly, the inventors of the subject invention realized that the end-organs of autonomic innervation are intrinsically sympathetic, thus resulting in the failure of the autonomic system to rebalance through the reduction of sympathetic tone-thereby offsetting the lost parasympathetic function-as vagal innervation generally wanes with aging. Accordingly, the inventors of the subject invention have realized that the end-organs of autonomic innervation are instrinsically sympathetic, and in the absence of regulation, they exhibit tonically adrenergic activity that cannot be mitigated by a decrease in extrinsic sympathetic signal. As such, the inventors of the subject invention realized that the excess sympathetic tone is not likely to be attributable to generalized elevation in circulating catecholamines. Thus, the loss of parasympathetic function with aging may be viewed as the unmasking the intrinsic sympathetic activity of end-organs, yielding clinical consequences similar to those associated with aging.

One of the most profound iterations of this theme may be the link between the autonomic and immune systems, in particularly the link between autonomic balance and Th-1/Th-2 balance. The superimposition of lifespan data on autonomic balance and Th-1/Th-2 balance (graph 1) demonstrates simultaneous peaking of relative parasympathetic and Th-1 functions during reproductive adulthood, followed by a gradual loss of these functions during the ensuing senescence. Co-migration of these functions over the lifespan suggests some link between the two functions and the autonomic system may in part be responsible for governing Th-1/Th-2 balance both regionally and systemically through innervations of various targets including the adrenal glands and lymphoid tissues.

The inventors of the subject invention have realized the dysregulation of inflammation resulting from the waning parasympathetic tone may be implicated in the susceptibility of the elderly to many other conditions such as atherosclerotic disease, cancer, osteoporosis, viral infections, allergic conditions, and sepsis. As such, the subject methods may be employed to electrically modulating a subject's autonomic nervous to treat aging-related conditions, including age-related disease conditions.

Accordingly, as described above, the subject methods may be employed in the treatment of a wide variety of conditions. For example, as noted above cardiovascular conditions, including diseases, such as atherosclerosis, coronary artery disease, hypertension, hyperlipidemia, eclampsia, pre-eclampsia, cardiomyopathy, volume retention, and the like, may be treated in accordance with the subject invention. Accordingly, branches of the autonomic nervous system that may be modulated to provide an increase in parasympathetic bias relative to sympathetic bias include but are not limited to, parasympathetic nerve and ganglia such as one or more of the vagus nerve, cardiac and pulmonary plexuses, celiac plexus, hypogastric plexus and pelvic nerves may be modulate to provide the desired increase in parasympathetic bias relative to sympathetic bias. In addition to or instead of modulating parasympathetic activity, cardiovascular diseases may be treated by modulating branches of the sympathetic nerve and ganglia such as one or more of the cervical sympathetic ganglia, dorsal and ventral rami of spinal nerves, coccygeal ganglia, postganglionic fibers to spinal nerves (innervating skin, blood vessels, sweat glands, erector pili muscle, adipose tissue), sympathetic chain ganglia, coccygeal ganglia, sympathetic nerves to cardiac and pulmonary plexuses, greater splanchnic nerve, lesser splanchnic nerve, inferior mesenteric ganglion, lumber splanchnic nerves, celiac ganglion, superior mesenteric ganglion, lumbar splanchnic nerves, may be modulate to provide the desired increase in parasympathetic bias relative to sympathetic bias.

As described above, the subject methods may also be employed to treat neurodegenerative conditions, including diseases, such as Alzheimer's disease, Pick's disease, Parkinson's disease, dementia, delerium, amyotrophic lateral sclerosis; neuroinflammatory diseases, e.g., viral meningitis, viral encephalitis, flngal meningitis, fungal encephalitis, multiple sclerosis, charcot joint, and the like. Branches of the autonomic nervous system that may be modulated in accordance with the subject invention to treat neurodegenerative diseases include parasympathetic nerve and ganglia such as, but not limited to one or more of the vagus nerve, cranial nerve III, cranial nerve VII, cranial nerve IX, sphenopalatine ganglion, ciliary ganglion, submandibular ganglion, otic ganglion and/or sympathetic nerve and ganglia such as, but not limited to one or more of cervical sympathetic ganglia.

Branches of the autonomic nervous system that may be modulated in accordance with the subject invention to treat orthopedic inflammatory diseases, e.g., osteoarthritis, reflex sympathetic dystrophy, osteoporosis, regional idiopathic, and the like, include parasympathetic nerve and ganglia such as, but not limited to one or more of the vagus nerve and/or sympathetic nerve and ganglia such, but not limited to one or more of the spinal nerves (dorsal and ventral rami), postganglionic fibers to spinal nerves (innervating skin, blood vessels, muscle, adipose tissue) and sympathetic chain ganglia.

Branches of the autonomic nervous system that may be modulated in accordance with the subject invention to treat inflammatory conditions, including diseases, such as multiple sclerosis and rheumatoid arthritis, migraines and chronic headaches, and the like, include parasympathetic nerve and ganglia such as, but not limited to one or more of the cranial nerve III, cranial nerve VII, cranial nerve IX, sphenopalatine ganglion, ciliary ganglion, submandibular ganglion, otic ganglion, vagus nerve, cardiac and pulmonary plexus, celiac plexus, hypogastric plexus and pelvic nerves and/or sympathetic nerve and ganglia such as, but not limited to one or more of the cervical sympathetic ganglia, spinal nerves (dorsal and ventral rami), postganglionic fibers to spinal nerves (innervating skin, blood vessels, sweat glands, erector pili muscle, adipose tissue), sympathetic chain ganglia, coccygeal ganglia, cardiac and pulmonary plexus, greater splanchnic nerve, lesser splanclnic nerve, inferior mesenteric ganglion, celiac ganglion, superior mesenteric ganglion and lumber splanchnic nerves.

Branches of the autonomic nervous system that may be modulated in accordance with the subject invention to treat lymphoproliferative conditions, including diseases, e.g., lymphoma, lymphoproliferative disease, Hodgkin's disease; autoimmune diseases, e.g., Graves disease, hashimoto's, takayasu's disease, kawasaki's diseases, arteritis, scleroderma, CREST syndrome, allergies, dermatitis, Henoch-schlonlein purpura, goodpasture syndrome, autoimmune thyroiditis, myasthenia gravis, lupus, and the like, include parasympathetic nerve and ganglia such as, but not limited to one or more of the cranial nerve III, cranial nerve VII, cranial nerve IX, sphenopalatine ganglion, ciliary ganglion, submandibular ganglion, otic ganglion, vagus nerve, cardiac and pulmonary plexus, celiac plexus, hypogastric plexus and pelvic nerves and/or sympathetic nerve and ganglia such as, but not limited to one or more of the cervical sympathetic ganglia, spinal nerves (dorsal and ventral rami), postganglionic fibers to spinal nerves (innervating skin, blood vessels, sweat glands, erector pili muscle, adipose tissue), sympathetic chain ganglia, coccygeal ganglia, cardiac and pulmonary plexus, greater splanchnic nerve, lesser splanchnic nerve, inferior mesenteric ganglion, celiac ganglion, superior mesenteric ganglion and lumber splanchnic nerves.

Branches of the autonomic nervous system that may be modulated in accordance with the subject invention to treat inflammatory conditions, including disease, and infectious diseases, e.g., sepsis, diseases of wound healing, viral and fungal infections, wound healing, tuberculosis, infection, and the like, include parasympathetic nerve and ganglia such as, but not limited to one or more of the cranial nerve III, cranial nerve VII, cranial nerve IX, sphenopalatine ganglion, ciliary ganglion, submandibular ganglion, otic ganglion, vagus nerve, cardiac and pulmonary plexus, celiac plexus, hypogastric plexus, pelvic nerves and/or sympathetic nerve and ganglia such as, but not limited to one or more of the cervical sympathetic ganglia, spinal nerves (dorsal and ventral rami), postganglionic fibers to spinal nerves (innervating skin, blood vessels, sweat glands, erector pili muscle, adipose tissue), sympathetic chain ganglia, coccygeal ganglia, cardiac and pulmonary plexus, greater splanchnic nerve, lesser splanchnic nerve, inferior mesenteric ganglion, celiac ganglion, superior mesenteric ganglion and lumber splanchnic nerves.

Branches of the autonomic nervous system that may be modulated in accordance with the subject invention to treat pulmonary conditions, including diseases, e.g., tachypnea, fibrotic diseases such as cystic fibrosis, interstitial lung disease, desquamative interstitial pneumonitis, non-specific interstitial pneumonitis, lymphocytic interstitial pneumonitis, usual interstitial pneumonitis, idiopathic pulmonary fibrosis; transplant-related side effects, and the like, include parasympathetic nerve and ganglia such as, but not limited to one or more of the vagus nerve, cardiac and pulmonary plexus, celiac plexus, hypogastric plexus, pelvic nerves and/or sympathetic nerve and ganglia such as, but not limited to one or more of the cervical sympathetic ganglia, spinal nerves (dorsal and ventral rami), postganglionic fibers to spinal nerves (innervating skin, blood vessels, sweat glands, erector pili muscle, adipose tissue), sympathetic chain ganglia, coccygeal ganglia, cardiac and pulmonary plexus, greater splanchnic nerve, lesser splanchnic nerve, inferior mesenteric ganglion, celiac ganglion, superior mesenteric ganglion and lumber splanchnic nerves.

Branches of the autonomic nervous system that may be modulated in accordance with the subject invention to treat gastrointestinal disorders, including diseases, e.g., hepatitis, xerostomia, bowel mobility, peptic ulcer disease, constipation, and the like, include parasympathetic nerve and ganglia such as, but not limited to one or more of the vagus nerve, celiac plexus, hypogastric plexus, pelvic nerves and/or sympathetic nerve and ganglia such as, but not limited to one or more of the sympathetic chain ganglia, coccygeal ganglia, cardiac and pulmonary plexus, greater splanchnic nerve, lesser splanchnic nerve, inferior mesenteric ganglion, celiac ganglion, superior mesenteric ganglion and lumber splanchnic nerves.

Branches of the autonomic nervous system that may be modulated in accordance with the subject invention to treat endocrine disorders, including diseases, e.g., hypothyroidism, diabetes, obesity, syndrome X, and the like, include parasympathetic nerve and ganglia such as, but not limited to one or more of the cranial nerve III, cranial nerve VII, cranial nerve IX, sphenopalatine ganglion, ciliary ganglion, submandibular ganglion, otic ganglion, vagus nerve, cardiac and pulmonary plexus, celiac plexus, hypogastric plexus, pelvic nerves and/or sympathetic nerve and ganglia such as, but not limited to one or more of the cervical sympathetic ganglia, spinal nerves (dorsal and ventral rami), postganglionic fibers to spinal nerves (innervating skin, blood vessels, sweat glands, erector pili muscle, adipose tissue), sympathetic chain ganglia, coccygeal ganglia, cardiac and pulmonary plexus, greater splanchnic nerve, lesser splanchnic nerve, inferior mesenteric ganglion, celiac ganglion, superior mesenteric ganglion and lumber splanchnic nerves.

Branches of the autonomic nervous system that may be modulated in accordance with the subject invention to treat cardiac rhythm disorders, e.g., sick sinus syndrome, bradycardia, tachycardia, arrhythmias, and the like, include parasympathetic nerve and ganglia such as, but not limited to one or more of the vagus nerve, cardiac and pulmonary plexus and/or sympathetic nerve and ganglia such as, but not limited to one or more of the cervical sympathetic ganglia, spinal nerves (dorsal and ventral rami), cardiac and pulmonary plexus.

Branches of the autonomic nervous system that may be modulated in accordance with the subject invention to treat genitourinary conditions, including diseases, e.g., bladder dysfunction, renal failure, erectile dysfunction; cancer, and the like, include parasympathetic nerve and ganglia such as, but not limited to one or more of the vagus nerve, cardiac and pulmonary plexus, celiac plexus, hypogastric plexus, pelvic nerves and/or sympathetic nerve and ganglia such as, but not limited to one or more of the cervical sympathetic ganglia, spinal nerves (dorsal and ventral rami), postganglionic fibers to spinal nerves (innervating skin, blood vessels, sweat glands, erector pili muscle, adipose tissue), sympathetic chain ganglia, coccygeal ganglia, cardiac and pulmonary plexus, greater splanchnic nerve, lesser splanchnic nerve, inferior mesenteric ganglion, celiac ganglion, superior mesenteric ganglion and lumber splanchnic nerves.

Branches of the autonomic nervous system that may be modulated in accordance with the subject invention to treat skin conditions, including diseases, e.g., wrinkles, cutaneous vasculitis, and the like, include parasympathetic nerve and ganglia such as, but not limited to one or more of the vagus nerve and/or sympathetic nerve and ganglia such as, but not limited to one or more of the cervical sympathetic ganglia such as, but not limited to one or more of the spinal nerves (dorsal and ventral rami), postganglionic fibers to spinal nerves (innervating skin, blood vessels, sweat glands, erector pili muscle, adipose tissue), sympathetic chain ganglia and coccygeal ganglia.

Branches of the autonomic nervous system that may be modulated in accordance with the subject invention to treat aging associated conditions, including diseases, e.g., shy dragers, multi-symptom atrophy, age related inflammation conditions, and the like, include parasympathetic nerve and ganglia such as, but not limited to one or more of the cranial nerve III, cranial nerve VII, cranial nerve IX, sphenopalatine ganglion, ciliary ganglion, submandibular ganglion, otic ganglion, vagus nerve, cardiac and pulmonary plexus, celiac plexus, hypogastric plexus, pelvic nerves and/or sympathetic nerve and ganglia such as, but not limited to one or more of the cervical sympathetic ganglia, spinal nerves (dorsal and ventral rami), postganglionic fibers to spinal nerves (innervating skin, blood vessels, sweat glands, erector pili muscle, adipose tissue), sympathetic chain ganglia, coccygeal ganglia, cardiac and pulmonary plexus, greater splanchnic nerve, lesser splanchnic nerve, inferior mesenteric ganglion, celiac ganglion, superior mesenteric ganglion and lumber splanchnic nerves.

Branches of the autonomic nervous system that may be modulated in accordance with the subject invention to treat Th-2 dominant conditions, including diseases, e.g., typhlitis, osteoporosis, lymphoma, myasthenia gravis, lupus, and the like, include parasympathetic nerve and ganglia such as, but not limited to one or more of the cranial nerve III, cranial nerve VII, cranial nerve IX, sphenopalatine ganglion, ciliary ganglion, submandibular ganglion, otic ganglion, vagus nerve, cardiac and pulmonary plexus, celiac plexus, hypogastric plexus, pelvic nerves and/or sympathetic nerve and ganglia such as, but not limited to one or more of the cervical sympathetic ganglia, spinal nerves (dorsal and ventral rami), postganglionic fibers to spinal nerves (innervating skin, blood vessels, sweat glands, erector pili muscle, adipose tissue), sympathetic chain ganglia, coccygeal ganglia, cardiac and pulmonary plexus, greater splanchnic nerve, lesser splanchnic nerve, inferior mesenteric ganglion, celiac ganglion, superior mesenteric ganglion and lumber splanchnic nerves.

Branches of the autonomic nervous system that may be modulated in accordance with the subject invention to treat autonomic dysregulation conditions, including diseases; e.g., headaches, concussions, post-concussive syndrome, coronary syndromes, coronary vasospasm; chronic pain and congestive heart failure, and the like, including parasympathetic nerve and ganglia such as, but not limited to one or more of the cranial nerve III, cranial nerve VII, cranial nerve IX, sphenopalatine ganglion, ciliary ganglion, submandibular ganglion, otic ganglion, vagus nerve, cardiac and pulmonary plexus, celiac plexus, hypogastric plexus, pelvic nerves and/or sympathetic nerve and ganglia such as, but not limited to one or more of the cervical sympathetic ganglia, spinal nerves (dorsal and ventral rami), postganglionic fibers to spinal nerves (innervating skin, blood vessels, sweat glands, erector pili muscle, adipose tissue), sympathetic chain ganglia, coccygeal ganglia, cardiac and pulmonary plexus, greater splanchnic nerve, lesser splanchnic nerve, inferior mesenteric ganglion, celiac ganglion, superior mesenteric ganglion and lumber splanchnic nerves.

Branches of the autonomic nervous system that may be modulated in accordance with the subject invention to treat conditions, including diseases, that cause hypoxia, hypercarbia, and/or hypercarbia and/or acidosis, such as chronic obstructive pulmonary disease ("COPD"), emphysema, any chronic lung disease that causes acidosis; sudden death syndromes, e.g., sudden infant death syndrome, sudden adult death syndrome, and the like, including parasympathetic nerve and ganglia such as, but not limited to one or more of the cranial nerve III, cranial nerve VII, cranial nerve IX, sphenopalatine ganglion, ciliary ganglion, submandibular ganglion, otic ganglion, vagus nerve, cardiac and pulmonary plexus, celiac plexus, hypogastric plexus, pelvic nerves and/or sympathetic nerve and ganglia such as, but not limited to one or more of the cervical sympathetic ganglia, spinal nerves (dorsal and ventral rami), postganglionic fibers to spinal nerves (innervating skin, blood vessels, sweat glands, erector pili muscle, adipose tissue), sympathetic chain ganglia, coccygeal ganglia, cardiac and pulmonary plexus, greater splanchnic nerve, lesser splanchnic nerve, inferior mesenteric ganglion, celiac ganglion, superior mesenteric ganglion and lumber splanchnic nerves.

Branches of the autonomic nervous system that may be modulated in accordance with the subject invention to treat conditions, including diseases, such as QT interval prolongation, acute pulmonary embolism, chronic pulmonary embolism, deep venous thrombosis, venous thrombosis, arterial thrombosis, coagulopathy, amniotic fluid embolism, pregnancy-related arrhythmias, fetal stress, fetal hypoxia, respiratory distress syndrome, amniotic fluid embolism, myocardial infarction, reperfusion syndrome, ischemia, epilepsy, seizures, stroke, pleural effuision, cardiogenic pulmonary edema, non-cardiogenic pulmonary edema, acute respiratory distress syndrome ("ARDS"), neurogenic edema, hyperreninemia, hepatorenal syndrome, pulmonary renal syndrome, aging, constipation, acidosis of any cause, hypercapnia, acidemia, renal tubular acidosis, aortic dissection, aortic aneurysm, insomnia, sleep disorders, cerebral vascular accident and transient ischemic attacks, and the like, include parasympathetic nerve and ganglia such as, but not limited to one or more of the cranial nerve III, cranial nerve VII, cranial nerve IX, sphenopalatine ganglion, ciliary ganglion, submandibular ganglion, otic ganglion, vagus nerve, cardiac and pulmonary plexus, celiac plexus, hypogastric plexus, pelvic nerves and/or sympathetic nerve and ganglia such as, but not limited to one or more of the cervical sympathetic ganglia, spinal nerves (dorsal and ventral rami), postganglionic fibers to spinal nerves (innervating skin, blood vessels, sweat glands, erector pili muscle, adipose tissue), sympathetic chain ganglia, coccygeal ganglia, cardiac and pulmonary plexus, greater splanchnic nerve, lesser splanchnic nerve, inferior mesenteric ganglion, celiac ganglion, superior mesenteric ganglion and lumber splanchnic nerves.

Branches of the autonomic nervous system that may be modulated in accordance with the subject invention to treat sleep apnea include cardiac branches of the sympathetic and parasympathetic systems and baroreceptors and chemoreceptors in the carotid arch and aortic bulb.

Devices and Systems

The subject invention also includes devices and systems that may be employed in the practice of the subject methods. The subject systems at least include an electrostimulatory device such that they include at least include one electrode for electrically modifying at least a portion of a subject's autonomic nervous system in accordance with the subject invention, as described above. In many embodiments, the electrostimulatory device is an implantable device, or at least certain components such as one or more electrodes, are implantable. Certain embodiments may include a plurality of electrodes, where some or all may be the same or some or all may be different. For example, at least a first electrode may be provide for electrically stimulating at least a portion of the parasympathetic system and at least a second electrode may be provided for inhibiting activity in at least a portion of the sympathetic system. In certain embodiments, a "test" electrode, as described above, may be included in a system. As noted above, such "test" electrodes may be a radiofrequency stimulating electrode. Still further, one or more electrodes may be included in a system which, instead of or in addition to delivering electric impulses to at least a portion of the autonomic nervous system, delivers an autonomic nervous system pharmacological agent to at least a portion of the autonomic nervous system. A system according to the subject invention typically also includes an energy source such as a battery or generator, where in certain embodiments the energy source may be implantable, and may also include one or more leads or wires for coupling the one or more electrodes to an energy source. In certain embodiments, the subject systems may include one or more autonomic nervous system pharmacological agents. In such embodiments, suitable delivery means may be included in the subject systems, dictated by the particular pharmacological agent as describe above, e.g., the particular form of the agent such as whether the pharmacological agent is formulated into preparations in solid, semi-solid, liquid or gaseous forms, such as tablets, capsules, powders, granules, ointments, solutions, suppositories, injections, inhalants and aerosols, and the like, and the particular mode of administration of the agent, e.g., whether oral, buccal, rectal, parenteral, intraperiactivityal, intradermal, transdermal, intracheal, etc. Accordingly, certain systems may include a suppository applicator, syringe, I.V. bag and tubing, electrode, etc. Systems may also include one or more devices for delivering, e.g., implanting, an electrosurgical device to a target site of a subject such as into the body cavity of a subject. For example, an endoscope, introducer needle, and the like, may be provided. Systems may also include one or more imaging or scanning apparatuses such as a fluoroscope, CT scan, and the like.

As described above, a system for use in practicing the subject methods may also include a suitable detector (not shown) for detecting one or more physical and/or chemical aspects related to the autonomic nervous system. The detector at least includes data gathering means. Also provided may be data analysis means where such may be a separate component from or integral with data gathering means, but in many embodiments is operatively coupled to data gathering means, e.g., integral with. In use, data related to one or more aspects of the autonomic nervous system may be collected by data gathering means and forwarded to data analysis means which executes steps necessary to process and evaluate the collected data and determine whether the autonomic nervous system is in need of electrical modulation. Such evaluation may include comparing data to reference values, etc. When present, a detector (or data evaluation means if separate) may be operatively coupled to one or more other elements of a given electrostimulatory device such that results of the determinations of autonomic modulation may automatically trigger (or cease) activation of electrical energy to the autonomic nervous system. For example, the detector may detect heart rate variability and determine that activity in the parasympathetic system needs to be increased and/or activity in the sympathetic system needs to be decreased. Accordingly, the electrostimulatory device may then be activated to provide the appropriate electrical energy. Suitable detectors include any detector capable of gathering information about the autonomic nervous system and includes both invasive, minimally invasive and non-invasive detectors where in certain embodiments a detector may be an implantable detector. Suitable detectors include, but are not limited to, those capable of collecting data regarding nerve conduction, circulating catecholamine levels, heart rate variability ("HRV"), post-ganglionic action potentials, QT interval, and the like and include, but are not limited to, MRI apparatuses, CT apparatus, neurography apparatuses, cardiovascular monitors, sensors including electrodes, etc.

Computer Readable Mediums and Programing Stored Thereon

Any part of the subject methods, e.g., detection, analysis and activation/termination of electrical energy including selecting suitable electrical parameters, may be performed manually or automatically. For example, the subject invention may include suitable computing means such as suitable hardware/software for performing one or more aspects of the subject methods. For example, one or more aspects of the subject invention may be in the form of computer readable media having programming stored thereon for implementing the subject methods. Accordingly, programming according to the subject invention may be recorded on computer-readable media, e.g., any medium that can be read and accessed directly or indirectly by a computer. Such media include, but are not limited to, computer disk or CD, a floppy disc, a magnetic "hard card", a server, magnetic tape, optical storage such as CD-ROM and DVD, electrical storage media such as RAM and ROM, and the hybrids of these categories such as magnetic/optical storage media. One of skill in the art can readily appreciate how any of the presently known computer readable mediums may be used to provide a manufacture that includes a recording of the present programming/algorithm for carrying out the above-described methodology. Thus, the computer readable media may be, for example, in the form of any of the above-described media or any other computer readable media capable of containing programming, stored electronically, magnetically, optically or by other means. As such, stored programming embodying steps for carrying-out some or all of the subject methods may be transferred to a computer-operated apparatus such as a personal computer (PC) or the like, by physical transfer of a CD, floppy disk, or like medium, or may be transferred using a computer network, server, or other interface connection, e.g., the Internet.

For example, the subject invention may include a computer readable medium that includes stored programming embodying an algorithm for carrying out some or all of the subject methods, where such an algorithm is used to direct a processor or series of processors to execute the steps necessary to perform the task(s) required of it and as such in certain embodiments the subject invention includes a computer-based system for carrying-out some or all of the subject methods. For example, such a stored algorithm may be configured to, or otherwise be capable of, directing a microprocessor to receive information directly or indirectly from data gathering means (i.e., information collected by data gathering means about the autonomic nervous system) and process that information to determine the state of the autonomic nervous system, e.g., the activity level of the parasympathetic system and/or the sympathetic system and even whether the autonomic nervous system requires modulation, e.g., if the parasympathetic activity is normal or abnormal and/or if sympathetic activity is normal or abnormal, and, if so, the specifics of the modulation that is required. The result of that processing may be communicated to a user, e.g., via audio and/or visual means, e.g., the algorithm may also include steps or functions for generating a variety of autonomic nervous system profile graphs, plots, etc.

The algorithm may be configured to, or otherwise be capable of, directing a microprocessor to activate, i.e., turn "on" and "off" an electrostimulatory device for applying energy to at least a part of the autonomic nervous system, e.g., in response to the above-described determination of the state of the autonomic nervous system. For example, if it is determined that parasympathetic activity needs to be increased and/or sympathetic activity needs to be decreased, the processor may direct the electrostimulatory device to provide the appropriate energy to result in the desired action. Accordingly, a processor may select the appropriate parameters (e.g., frequency, amplitude, etc.) depending on what is required and direct an electrostimulatory device to implement the parameters.

The subject invention may also include a data set of known or reference information stored on a computer readable medium to which autonomic nervous system data collected may be compared for use in determining the state of the autonomic nervous system. The data may be stored or configured in a variety of arrangements known to those of skill in the art.

Kits

Also provided are kits for practicing the subject methods. While the subject kits may vary greatly in regards to the components included, typically, the kits at least include an electrostimulatory device, as described above. Accordingly, subject kits typically at least include an electrostimulatory device such that they include at least include one electrode for electrically modifying at least a portion of a subject's autonomic nervous system in accordance with the subject invention, as described above. In many embodiments, the electrostimulatory device provided in a kit is an implantable device, or at least certain components such as one or more electrodes, are implantable. Certain kits may include a plurality of electrodes, where some or all may be the same or some or all may be different. For example, certain kits may include at least a first electrode for electrically stimulating at least apportion of the parasympathetic system and at least a second electrode for inhibiting activity in at least a portion of the sympathetic system. In certain embodiments, a subject kit may include a "test" electrode, as described above such as a radiofrequency stimulating electrode. Still further, one or more electrodes may be included in a kit which, instead of or in addition to delivering electric impulses to at least a portion of the autonomic nervous system, delivers an autonomic nervous system pharmacological agent to at least a portion of the autonomic nervous system. Kits according to the subject invention typically also include an energy source such as a battery or generator, where in certain embodiments the energy source may be implantable, and may also include one or more leads or wires for coupling the one or more electrodes to an energy source.

Devices for delivering, e.g., implanting, an electrosurgical device to a target site of a subject such as into the body cavity of a subject may also be included in the subject kits. For example, an endoscope, introducer needle, and the like may be provided.

The subject kits also generally include instructions for how to practice the subject methods and in particular how to use the electrostimulatory device provided in the kit to treat a subject for a condition caused by an abnormality in the subject's autonomic nervous system by electrically modulating at least a portion of the subject's autonomic nervous system to increase parasympathetic activity relative to sympathetic activity. The instructions are generally recorded on a suitable recording medium or substrate. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The subject kits may also include one or more autonomic nervous system pharmacological agents. The dosage amount of the one or more pharmacological agents provided in a kit may be sufficient for a single application or for multiple applications. Accordingly, in certain embodiments of the subject kits a single dosage amount of a pharmacological agent is present.

In certain other embodiments, multiple dosage amounts of a pharmacological agent may be present in a kit. In those embodiments having multiple dosage amounts of pharmacological agent, such may be packaged in a single container, e.g., a single tube, bottle, vial, and the like, or one or more dosage amounts may be individually packaged such that certain kits may have more than one container of a pharmacological agent.

Suitable means for delivering one or more pharmacological agents to a subject may also be provided in a subject kit. The particular delivery means provided in a kit is dictated by the particular pharmacological agent employed, as describe above, e.g., the particular form of the agent such as whether the pharmacological agent is formulated into preparations in solid, semi-solid, liquid or gaseous forms, such as tablets, capsules, powders, granules, ointments, solutions, suppositories, injections, inhalants and aerosols, and the like, and the particular mode of administration of the agent, e.g., whether oral, buccal, rectal, parenteral, intraperiactivityal, intradermal, transdermal, intracheal, etc. Accordingly, certain systems may include a suppository applicator, syringe, I.V. bag and tubing, electrode, etc.

Some or all components of the subject kits may be packaged in suitable packaging to maintain sterility. In many embodiments of the subject kits, the components of the kit are packaged in a kit containment element to make a single, easily handled unit, where the kit containment element, e.g., box or analogous structure, may or may not be an airtight container, e.g., to further preserve the sterility of some or all of the components of the kit.

It is evident from the above discussion that the above described invention provides methods, system and kits for treating a subject for a condition caused by an abnormality in said subject's autonomic nervous system which are simple to use, effective, and can be used to treat variety of different conditions. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of treating a subject for at least one of: hypoxia, hypercapnia, hypercarbia and acidosis, said method comprising:
    modulating at least a portion of said subject's autonomic nervous system to increase the parasympathetic activity/sympathetic activity ratio in a manner effective to treat said condition, wherein said parasympathetic activity is increased by increasing activity in at least one parasympathetic nerve fiber; and
    decreasing the sensitivity of a chemoreceptor to said at least one of: hypoxia, hypercapnia, hypercarbia and acidosis.

2. The method of claim 1, wherein said method is a method of treating hypoxia, hypercapnia, hypercarbia and acidosis.

3. The method of claim 1, further comprising determining the presence of at least one of hypoxia, hypercapnia, hypercarbia and acidosis prior to said modulation.

4. The method of claim 3, further comprising determining the cause of at least one of hypoxia, hypercapnia, hypercarbia and acidosis.

5. The method of claim 3, further comprising determining the state of said autonomic nervous system prior to said modulation.

6. The method of claim 5, wherein said method comprises determining the parasympathetic activity/sympathetic activity ratio.

7. The method of claim 6, wherein said method comprises determining the parasympathetic activity/sympathetic activity ratio following said modulation.

8. The method of claim 6, wherein said method further comprises repeating said modulation following said determination.

9. The method of claim 1, wherein said modulation comprises pharmacological modulation.

10. The method of claim 9, wherein said pharmacological modulation comprises administering an effective amount of at least one pharmacological agent to said subject chosen from: beta-blockers; aldosterone antagonists; angiotensin II receptor blockades; angiotensin converting enzyme inhibitors; statins; triglycerides lowering agents; niacin; diabetes agents; immunomodulators; nicotine; sympathomimetics; antihistamines; cholinergics; acetylcholinesterase inhibitors; magnesium and magnesium sulfates; calcium channel blockers; muscarinics; sodium channel blockers; glucocorticoid receptor blockers; peripheral andrenergic inhibitors; blood vessel dilators; central agonists; combined alpha and beta-blockers; alpha blockers; combination diuretics; cyclic nucleotide monophosphodiesterase ("PDE") inhibitors; alcohols; vasopressin inhibitors; oxytocin inhibitors; glucagons like peptide 1; relaxin hormone; renin inhibitors; estrogen compounds; progesterone inhibitors; testosterone inhibitors; gonadotropin-releasing hormone analogues (GnRH-As); gonadotropin-releasing hormone inhibitors; vesicular monoamine transport (VMAT) inhibitors; dipeptidyl peptidase (DP) IV inhibitors; melatonin; potassium sparing diuretics, adiponectin; phenserine; phospohodiesterase 4 inhibitor; valproate; dehydroepiandrostonedione, and anti-coagulants.

11. The method of claim 1, wherein said modulation comprises electrical modulation.

12. The method of claim 1, wherein said chemoreceptor is a central chemoreceptor.

13. The method of claim 12, wherein said central chemoreceptor is a medulla chemoreceptor.

14. The method of claim 1, wherein said chemoreceptor is a peripheral chemoreceptor.

15. The method of claim 14, wherein said peripheral chemoreceptor is a carotid chemoreceptor.

16. The method of claim 14, wherein said peripheral chemoreceptor is an aortic arch chemoreceptor.

17. The method of claim 1, wherein said method comprises decreasing conduction in an afferent nerve that carries signal from said chemoreceptor.

18. The method of claim 17, wherein said afferent nerve is a nerve that carries signal to sympathetic nerves of said autonomic nervous system.

19. The method of claim 18, wherein said sympathetic nerves participate in stimulating inflammation.

20. The method of claim 1, wherein said method comprises decreasing conduction in an efferent nerve that carries signal from said chemoreceptor.

21. The method of claim 20, wherein said efferent nerve is a nerve that carries signal from sympathetic nerves of said autonomic nervous system.

22. The method of claim 21, wherein said sympathetic nerves participate in stimulating inflammation.

23. The method of claim 1, wherein said method comprises increasing conduction in an afferent nerve that carries signal from said chemoreceptor.

24. The method of claim 23, wherein said afferent nerve is a nerve that carries signal to parasympathetic nerves of said autonomic nervous system.

25. The method of claim 24, wherein said parasympathetic nerves participate in decreasing inflammation.

26. The method of claim 1, wherein said method comprises increasing conduction in an efferent nerve that carries signal from said chemoreceptor.

27. The method of claim 26, wherein said efferent nerve is a nerve that carries signal from parasympathetic nerves of said autonomic nervous system.

28. The method of claim 27, wherein said parasympathetic nerves participate in decreasing inflammation.

29. The method of claim 1, wherein said modulation comprises electrical and pharmacological modulation.

30. The method of claim 1, wherein said modulation treats a condition associated with said at least one of hypoxia, hypercapnia, hypercarbia and acidosis.

31. The method of claim 30, wherein said associated condition is caused by at least one of: hypoxia, hypercapnia, hypercarbia acidosis, and a condition having a manifestation of at least one of hypoxia, hypercapnia, hypercarbia and acidosis at least one of hypoxia, hypercapnia, hypercarbia and acidosis.

32. The method of claim 31, wherein said associated condition is chosen from: aging, cardiovascular conditions, neurodegenerative conditions, neuroinflammatory conditions, orthopedic inflammatory conditions, lymphoproliferative conditions, autoimmune conditions, infections diseases, pulmonary conditions, transplant-related side-effects, gastrointestinal conditions, endocrine conditions, cardiac rhythm conditions, genitourinary conditions, cancer, skin conditions, autonomic instability conditions, sudden death syndromes, atherosclerosis, hypertension, insulin resistance, diabetes, and glaucoma.

33. The method of claim 31, wherein said associated condition is a condition having a manifestation of at least one of hypoxia, hypercapnia, hypercarbia and acidosis.

34. The method of claim 33, wherein said condition is chosen from: sleep apnea, acidemia, hypercapnia, hypoxia ventilation/perfusion, emphysema, chronic obstructive pulmonary disease, primary pulmonary hypertension, secondary pulmonary hypertension, cyctic fibrosis, obesity, obesity hypoventilation syndrome, chronic pulmonary embolism, chronic infection, asthma, inhalational disorders, sarcoid, tuberculosis, pneumoconiosis, coal worker ling, asbestos, left-to-right-shunts, right-to-left shunts, cyanotic lung disease, vascular malformations, atrial septal defects, ventricular septal defects, patent ductus arteriosus, bronchopulmonary dysplasia, granulatomous lung diseases, heart failure, pulmonary edema, usual interstitial pneumonia (UIP), disquamative interstitial pneumonia (DIP), nonspecific interstitial pneumonia (NSIP), lymphocyctic interstitial pneumonia (LIP) acute interstitial pneumonia (AIP), rheumatoid arthritis, wegener's granulomatosis, unilateral pneumonectomy, ARDS, histocytosis, bronchiolitis obliterans organizing pneumonia (BOOP), pleural effusion, cancer, sudden death syndromes, congestive heart failure, pulmonary edema, cardiogenic pulmonary edema, non-cardiogenic pulmonary edema, neurogenic edema, emphysema, pulmonary fibrosis, obesity hypoventilation syndrome, HIV, scleroderma, chronic lung diseases, acute lung injury, acute pulmonary embolism, acute respiratory distress syndrome, asphyxiation, drowning, anemia, sickle cell disease, thalassemia, anion gap, non-anion gap, metabolic acidosis, renal tubular acidosis, drug induced acidosis, renal failure, and uremia.

35. The method of claim 33, wherein said condition is obstructive sleep apnea.

36. The method of claim 1, further comprising observing a physiological aspect or biologic aspect of said subject and adjusting said modulation based on said aspect.

37. The method of claim 36, wherein said adjusting comprises changing a pharmacological modulation protocol.

38. The method of claim 37, wherein the dose of a pharmacological agent is changed.

39. The method of claim 37, wherein the type of pharmacological agent is changed.

40. The method of claim 36, wherein said adjusting comprises changing an electrical energy applying protocol.

41. The method of claim 40, wherein at least one of amplitude, frequency and waveform of applied current.

42. The method of claim 36, wherein said modulation is terminated when a predetermined aspect of said physiological aspect or biologic aspect is observed.

43. A method comprising treating a subject for a condition associated with of least one of hypoxia, hypercapnia, hypercarbia and acidosis, said method comprising:
  modulating at least a portion of said subject's autonomic nervous system to increase the parasympathetic activity/sympathetic activity ratio in a manner effective to treat said condition, wherein said parasympathetic activity is increased by increasing activity in at least one parasympathetic nerve fiber; and
  decreasing the sensitivity of a chemoreceptor to said at least one of: hypoxia, hypercapnia, hypercarbia and acidosis.

44. The method of claim 43, wherein said associated condition is a condition having a manifestation of least one of hypoxia, hypercapnia, hypercarbia and acidosis.

45. The method of claim 44, wherein said condition is chosen from: sleep apnea, acidemia, hypercapnia, hypoxia ventilation/perfusion, emphysema, chronic obstructive pulmonary disease, primary pulmonary hypertension, secondary pulmonary hypertension, cyctic fibrosis, obesity, obesity hypoventilation syndrome, chronic pulmonary embolism, chronic infection, asthma, inhalational disorders, sarcoid, tuberculosis, pneumoconiosis, coal worker ling, asbestos, left-to-right-shunts, right-to-left shunts, cyanotic lung disease, vascular malformations, atrial septal defects, ventricular septal defects, patent ductus arteriosus, bronchopulmonary dysplasia, granulatomous lung diseases, heart failure, pulmonary edema, usual interstitial pneumonia (UIP), disquamative interstitial pneumonia (DIP), nonspecific interstitial pneumonia (NSIP), lymphocyctic interstitial pneumonia (LIP) acute interstitial pneumonia (AIP), rheumatoid arthritis, wegener's granulomatosis, unilateral pneumonectomy, ARDS, histocytosis, bronchiolitis obliterans organizing pneumonia (BOOP), pleural effusion, cancer, sudden death syndromes, congestive heart failure, pulmonary edema, cardiogenic pulmonary edema, non-cardiogenic pulmonary edema, neurogenic edema, emphysema, pulmonary fibrosis, obesity hypoventilation syndrome, HIV, scleroderma, chronic lung diseases, acute lung injury, acute pulmonary embolism, acute respiratory distress syndrome, asphyxiation, drowning, anemia, sickle cell disease, thalassemia, anion gap, non-anion gap, metabolic acidosis, renal tubular acidosis, drug induced acidosis, renal failure, and uremia.

46. The method of claim 45, wherein said condition is obstructive sleep apnea.

47. The method of claim 43, wherein said associated condition is caused by at least one of: hypoxia, hypercapnia, hypercarbia, and acidosis, and a condition having a manifestation of at least one of hypoxia, hypercapnia, hypercarbia and acidosis at least one of hypoxia, hypercapnia, hypercarbia and acidosis.

48. The method of claim 47, wherein said associated condition is chosen from: aging, cardiovascular conditions, neurodegenerative conditions, neuroinflammatory conditions, orthopedic inflammatory conditions, lymphoproliferative conditions, autoimmune conditions, infections diseases, pulmonary conditions, transplant-related side-effects, gastrointestinal conditions, endocrine conditions, cardiac rhythm conditions, genitourinary conditions, cancer, skin conditions, autonomic instability conditions, sudden death syndromes, atherosclerosis, hypertension, insulin resistance, diabetes, and glaucoma.

49. The method of claim 43, further comprising determining the presence of at least one of hypoxia, hypercapnia and acidosis prior to said modulation.

50. The method of claim 49, comprising determining at least one of pH, the concentration of oxygen and the concentration of carbon dioxide in bodily fluid of said subject.

51. The method of claim 43, further comprising determining the state of said autonomic nervous system prior to said modulation.

52. The method of claim 43, wherein said method comprises determining the state of at least one of parasympathetic activity and sympathetic activity.

53. The method of claim 52, wherein said method comprises determining the parasympathetic activity/sympathetic activity ratio.

54. The method of claim 53, wherein said method comprises determining the parasympathetic activity/sympathetic activity ratio following said modulation.

55. The method of claim 53, wherein method comprises decreasing conduction in an afferent nerve that carries signal from said chemoreceptor.

56. The method of claim 55, wherein said afferent nerve is one that carries signal to sympathetic nerves of said autonomic nervous system.

57. The method of claim 56, wherein said sympathetic nerves participate in stimulating inflammation.

58. The method of claim 43, wherein said modulation comprises pharmacological modulation.

59. The method of claim 58, wherein said pharmacological modulation comprises administering an effective amount of at least one pharmacological agent to said subject chosen from: beta-blockers; aldosterone antagonists; angiotensin II receptor blockades; angiotensin converting enzyme inhibitors; statins; triglycerides lowering agents; niacin; diabetes agents; immunomodulators; nicotine; sympathomimetics; antihistamines; cholinergics; acetylcholinesterase inhibitors; magnesium and magnesium sulfates; calcium channel blockers; muscarinics; sodium channel blockers; glucocorticoid receptor blockers; peripheral andrenergic inhibitors; blood vessel dilators; central agonists; combined alpha and beta-blockers; alpha blockers; combination diuretics; potassium sparing diuretics, cyclic nucleotide monophosphodiesterase ("PDE") inhibitors; alcohols; vasopressin inhibitors; oxytocin inhibitors; glucagons like peptide 1; relaxin hormone; renin inhibitors; estrogen compounds; progesterone inhibitors; testosterone inhibitors; gonadotropin-releasing hormone analogues (GnRH-As); gonadotropin-releasing hormone inhibitors; vesicular monoamine transport (VMAT) inhibitors; dipeptidyl peptidase (DP) IV inhibitors; melatonin; adiponectin; phenserine; phospohodiesterase 4inhibitor; valproate; dehydroepiandrostonedione; and anticoagulants.

60. The method of claim 43, wherein said modulation comprises electrical modulation.

61. The method of claim 43, wherein said chemoreceptor is a central chemoreceptor.

62. The method of claim 61, wherein said central chemoreceptor is a medulla chemoreceptor.

63. The method of claim 62, wherein said chemoreceptor is a peripheral chemoreceptor.

64. The method of claim 63, wherein said peripheral chemoreceptor is a carotid chemoreceptor.

65. The method of claim 63, wherein said peripheral chemoreceptor is an aortic arch chemoreceptor.

66. The method of claim 43, wherein said method comprises decreasing conduction in an efferent nerve that carries signal from said chemoreceptor.

67. The method of claim 66, wherein said efferent nerve is a nerve that carries signal from sympathetic nerves of said autonomic nervous system.

68. The method of claim 67, wherein said sympathetic nerves participate in stimulating inflammation.

69. The method of claim 43, wherein said method comprises increasing conduction in an afferent nerve that carries signal from said chemoreceptor.

70. The method of claim 69, wherein said afferent nerve is a nerve that carries signal
to parasympathetic nerves of said autonomic nervous system.

71. The method of claim 70, wherein said parasympathetic nerves participate in decreasing inflammation.

72. The method of claim 43, wherein said method comprises increasing conduction in an efferent nerve that carries signal from said chemoreceptor.

73. The method of claim 72, wherein said efferent nerve is a nerve that carries signal from parasympathetic nerves of said autonomic nervous system.

74. The method of claim 73, wherein said parasympathetic nerves participate in decreasing inflammation.

75. The method of claim 43, wherein said modulation comprises electrical and pharmacological modulation.

76. The method of claim 43, further comprising observing a physiological aspect or biologic aspect of said subject and adjusting said modulation based on said aspect.

77. The method of claim 76, wherein said adjusting comprises changing a pharmacological modulation protocol.

78. The method of claim 77, wherein the dose of a pharmacological agent is changed.

79. The method of claim 77, wherein the type of pharmacological agent is changed.

80. The method of claim 76, wherein said adjusting comprises changing an electrical energy applying protocol.

81. The method of claim 80, wherein at least one of amplitude, frequency and waveform of applied current.

82. The method of claim 76, wherein said modulation is terminated when a predetermined aspect of said physiological aspect or biologic aspect is observed.

* * * * *